United States Patent [19]
Stormann et al.

[11] Patent Number: 6,051,688
[45] Date of Patent: Apr. 18, 2000

[54] ISOLATED HUMAN METABOTROPIC GLUTAMATE RECEPTOR MGLUR-8

[75] Inventors: Thomas M. Stormann; Rachel T. Simin, both of Salt Lake City; Lance G. Hammerland, Bountiful; Forrest H. Fuller, Salt Lake City, all of Utah

[73] Assignee: NPS Pharmaceuticals, Inc., Salt Lake City, Utah

[21] Appl. No.: 08/823,437

[22] Filed: Mar. 24, 1997

Related U.S. Application Data

[62] Division of application No. 08/604,298, Feb. 21, 1996.

[51] Int. Cl.$^7$ .......................... C07K 14/705; C12N 15/12
[52] U.S. Cl. .......................... 530/350; 435/69.1; 536/23.5
[58] Field of Search .......................... 435/69.1; 530/350; 576/23.5; 514/74

[56] References Cited

FOREIGN PATENT DOCUMENTS

| 93303520 | 5/1993 | European Pat. Off. . |
| 9203736 | of 0000 | WIPO . |
| 9210583 | 6/1992 | WIPO . |
| 9304373 | 3/1993 | WIPO . |
| 9323569 | 11/1993 | WIPO . |
| 9511221 | 4/1995 | WIPO . |
| 95/18154 | 7/1995 | WIPO . |
| 97/05252 | 2/1997 | WIPO . |

OTHER PUBLICATIONS

Ohishi et al., "Immunohistochemical Localization of Metabotropic Glutamate Receptors, mGluR2 and mGluR3, in Rat Cerebellar Cortex," *Neuron* 13:55–66 (19940).

Ohishi et al., "Distribution of the Messenger RNA for a Metabotropic Glutamate Receptor, mGluR2, in the Central Nervous System of the Rat," *Neuroscience* 53:1009–1018 (1993).

Okamoto et al., *J. Biol. Chem.* 269: 1231 (1994).

Pin and Duvoisin, "Review: Neurotransmitter receptors I," *Neuropharmacology* 34:1–26 (1995).

Pin et al., "Alternative splicing generates metabotropic glutamate receptors inducing different patterns of calcium release in Xenopus oocytes," *Proc. Natl. Acad. Sci. USA* 89:10331–10335 (1992).

Pin et al., *Curr. Drugs: Neurodegenerative Disorders* 1:111 (1993).

Pursel et al., "Genetic Engineering of Livestock," *Science* 244:1281–1288 (1989).

Pizzi et al., *J. Neurochem.* 61:683 (1993).

Riccardi et al., "Cloning and functional expression of a rat kidney extracellular calcium/polyvalent cation–sensing receptor," *Proc. Natl. Acad. Sci. USA* 92:131–135 (1995).

Ruat et al., *Proc. Natl. Acad. Sci. USA* 92:3161 (1995).

Sacaan and Schoepp, *Neurosci. Lett.* 139:77 (1992).

Saugstad et al., *Mol. Pharmacol.* 45:367 (1994).

Schoepp, "Novel Functions for Subtypes of Metabotropic Glutamate Receptors," *Neurochem. Int.* 24:439–449 (1994).

Schoepp and Conn, *Trends Pharmacol. Sci.* 14:13 (1993).

Sheardown, *Neuroreport* 3:916 (1992).

Shigemoto et al., "Antibodies Inactivating mGluR1 Metabotropic Glutamate Receptor Block Long–Term Depression in Cultured Purkinje Cells," *Neuron* 12:1245–1255 (1994).

Siliprandi et al., *Eur. J. Pharmacol.* 219:173 (1992).

Tanabe et al., "Signal Transduction, Pharmacological Properties, and Expression Patterns of Two Rat Metabotropic Glutamate Receptors, mGluR3 and mGluR4," *J. Neuroscience* 13:1372–1378 (1993).

Tanabe et al., *Neuron* 8:169 (1992).

Taschenberger et al., *Neuroreport* 3:629 (1992).

Thomsen et al., "(S)–4–Carboxy–3–Hydroxyphenylglycine, an Antagonist of Metabotropic Glutamate Receptor (mGluR)1a and an Agonist of mGlurR2, Protects Against Audiogenic Seizures in DBA/2 Mice," *J. Neurochem.* 62:2492–2495 (1994).

Trombley and Westbrook, "L–AP4 Inhibits Calcium Currents and Synaptic Transmission via a G–Protein–coupled Glutamate Receptor," *J. Neuroscience* 12:2043–2050 (1992).

Uhlmann and Peyman, "Antisense Oligonucleotides: A New Therapeutic Principle," *Chemical Reviews* 90:544–584 (1990).

Watkins and Collingridge, "Phenylglycine derivatives as antagonists of metabotropic glutamate receptors," *Trends Pharmacol Sci.* 15:333–342 (1994).

Witkop, "Nonenzymatic Methods for the Preferential and Selective Cleavage and Modification of Proteins," *Advances in Protein Chemistry* eds. C.B. Anfinsen, K. Bailey, M.L. Anson, J.T. Edsall (New York:Academic Press) 16:221–321 (1961).

Jane et al., "Stereospecific Antagonism By (+)α–Methyl–4–Carboxyphenylglycine (MCPG) of (1S, 3R)–ACPD–Induced Effects in Neonatal Rat Motoneurones and Rat Thalamic Neurones," *Br. J. Pharmacol.* 32:725–727 (1993).

Jansen et al, "Immunotoxins: Hybrid Molecules Combining High Specificity and Potent Cytotoxicity," *Immunological Rev.* 62:185–216 (1982).

Joly et al., "Molecular, Functional, and Pharmacological Characterization of the Metabotropic Glutamate Receptor Type 5 Splice Variants: Comparison with mGluR1," *J. Neuroscience* 15:3970–3981 (1995).

Joyner et al., "Production of a mutation in mouse En–2 gene by homologous recombination in embryonic stem cells," *Nature* 338:153–156 (1989).

(List continued on next page.)

*Primary Examiner*—John Ulm
*Attorney, Agent, or Firm*—Lyon & Lyon LLP

[57] ABSTRACT

A human metabotropic glutamate receptor (mGluR) protein is identified, sequenced, and cloned. The receptor may be used to screen for compounds that modulate the activity of the mGluR. The recombinant mGluR as well as compounds that modulate mGluR activity may be used in the diagnosis and treatment of neurological disorders and diseases.

10 Claims, 15 Drawing Sheets

OTHER PUBLICATIONS

Killen and Lindstrom, "Specific Killing of Lymphocytes that Cause Experimental Autoimmune Myasthenia Gravis by Ricin Toxin–Acetylcholine Receptor Conjugates," *J. of Immunology* 133:2549–2553 (1984).

Knopfel et al., "Metabotropic Glutamate Receptors: Novel Targets for Drug Development," *J. Med. Chem.* 38:1417–1428 (1995).

Koerner and Johnson, "Ch. 14—L–AP4 receptor ligands," *Excitatory Amino Acid Receptors; Design of Agonists and Antagonists* pp. 308–330 (1992).

Koh et al., *Proc. Natl. Acad. Sci. USA* 88:9431 (1991).

Krapvinsky et al., Nature 374: 135, 1995.

Kubo et al., *Nature* 364:802, 1993.

Lin et al., *Soc. Neurosci. Abstr.* 20:468 (1994) (p. 28).

Lindley, "A New Synthetic Substrate for Trypsin and its Application to the Determination of the Amino–acid Sequence of Proteins," *Nature* 178:647–658 (1956).

Lipparti et al., "In Rats, the Metabotropic Glutamate Receptor–Triggered Hippocampal Neuronal Damage is Strain–Dependent," *Life Science* 52:85–90 (1993).

Lombardi et al., "Pharmacological characterization of the metabotropic glutamate receptor inhibiting D–[$^3$H]–aspartate output in rat striatum," *Br. J. Pharmacol.* 110:1407–1412 (1993).

Martin et al., "Cellular Localization of a Metabotropic Glutamate Receptor in Rat Brain," *Neuron* 9:259–270 (1992).

Masu et al., *Nature* 349:760 (1991).

Meller et al., *Neuroreport* 4:879 (1993).

Miller, "Human gene therapy comes of age," *Nature* 357:455–460 (1992).

Minakami et al., "Molecular Cloning and the Functional Expression of Two Isoforms of Human Metabotropic Glutamate Receptor Subtype 5," *Biochem. Biophys. Res. Commun.* 199:1136–1143 (1994).

Nakajima et al., "Molecular Characterization of a Novel Retinal Metabotropic Glutamate Receptor mGluR6 with a High Agonist Selectively for L–2–Amino–4–phosphonobutyrate," *J. Biol. Chem.* 268:11868–11873 (1993).

Nakajima et al., *J. Biol. Chem.* 267:2437 (1992).

Nakanishi, "Metabotropic Glutamate Receptors: Synaptic Transmission, Modulation, and Plasticity," *Neuron* 13:1031–1037 (1994).

O'Hara et al., *Neuron* 11:41 (1993).

Calabresi et al., "Activation of quisqualate metabotropic receptors reduces glutamate and GABA–mediated synaptic potentials in the rat striatum," *Neurosci. Lett.* 139:41–44 (1992).

Capecchi, "Altering the Gonome by Homologous Recombination," *Science* 244:1288–1292 (1989).

Chiamulera et al., *Eur. J. Pharmacol.* 216:335 (1992).

Cockcroft et al., *Neurochem. Int.* 23:583–594 (1993).

Cunningham et al., *Life Sci.* 54:135 (1994).

Duvoisin et al., "A Novel Metabotropic Glutamate Receptor Expressed in the Retina and Olfactory Bulb," *J. Neuroscience* 15:3075–3083 (1995).

Eaton et al., *Eur. J. Pharm.—Mol. Pharm. Sect.* 244:195–197 (1993).

Ferguson and Williams, "Cell–Surface Anchoring of Proteins Via Glycosylphosphatidylinositol Structures," *Ann. Rev. Biochem.* 57:285–320 (1988).

Flor et al., *Neuropharmacol.* 34:149 (1994).

Flor et al., *Soc. Neurosci. Abstr.* 20:468 (1994).

Garrett et al., *J. Biol. Chem.* 270:12919 (1995).

Goldberger and Anfinsen, "The Reversible Masking of Amino Groups in Ribonuclease and Its Possible Usefulness in the Synthesis of the Protein," *Biochemistry* ed. H. Neurath (Easton, PA:Mack Printing Company) 1:401–405 (1962).

Greene et al., "Metabotropic receptor mediated afterdepolarization in neocortical neurons," *Eur. J. Pharmacol.* 226:279–280 (1992).

Gross and Witkop, "Selective Cleavage of the Methionyl Peptide Bonds in Ribonuclease with Cyanogen Bromide," *J. Amer. Chem. Soc.* 83:1510–1511 (1961).

Hammer et al., "Spontaneous Inflammatory Disease in Transgenic Rats Expressing HLA–B27 and Human $\beta_2$m: An Animal Model of HLA–B27–Associated Human Disorders," *Cell* 63:1099–1112 (1990).

Hayashi et al., "Role of a metabotropic glutamate receptor in synaptic modulation in the accessory olfactory bulb," *Nature* 366:687–690 (1993).

Hélène and Toulmé, "Specific regulation of gene expression by antisense, scene and antigene nucleic acids," *Chemica et Biophysica Acta* 1049:99–125 (1990).

Hollman and Heinemann, *Ann. Rev. Neurosci.* 17:31 (1994).

Houamed et al., *Science* 252:1318 (1991).

Houdebine and Chourrout, "Transgenesis in Fish," *Experientia* 47:891–897 (1991).

Hu and Storm, "Excitatory amino acids acting on metabotropic glutamate receptors broaden the action potential in hippocampal neurons," *Brain Res.* 568:339–344 (1991).

Hutchinson et al., "Mutagenesis at a Specific Position in a DNA Sequence," *J. Biol. Chem.* 253:6551–6560 (1978).

Ikeda et al., "Heterologous Expression of Metabotropic Glutamate Receptors in Adult Rat Sympathetic Neurons: Subtype–Specific Coupling to Ion Channels," *Neuron* 14:1029–1038 (1995).

Ishida et al., *Br. J. Pharmacol.* 109:1169 (1993).

Abe et al., "Molecular Characterization of a Novel Metabotropic Glutamate Receptor mGluR5 Coupled to Inositol Phosphate/$Ca^{2+}$ Signal Transduction," *J. Biol. Chem.* 267:13361–13368 (1992).

Aiba et al., "Deficient Cerebellar Long–Term Depression and Impaired Motor Learning in mGluR1 Mutant Mice," *Cell* 79:377–388 (1994).

Aiba et al., "Reduced Hippocampal Long–Term Potentiation and Context–Specific Deficit in Associative Learning in mGluR1 Mutant Mice," *Cell* 79:365–375 (1994).

Ambrosini et al., "Metabotropic Glutamate Receptors Negatively Coupled to Adenylate Cyclase Inhibit N–Methyl–D–aspartate Receptor Activity and Prevent Neurotoxicity in Mesencephalic Neurons In Vitro," *Mol. Pharmacol.* 47:1057–1064 (1995).

Aramori and Nakanishi, *Neuron* 8:757 (1992).

Ashford et al., *Nature* 370:456 (1994).

Bashir et al., *Nature* 363:347 (1993).

Baskys, "Metabotropic receptors and 'slow' excitatory actions of glutamate agonists in the hippocampus," *Trends in Neurosciences* 15:92–96 (1992).

Bortolotto et al., *Nature* 368:740 (1994).

Brinster et al., "Factors affecting the efficiency of introducing foreign DNA into mice by microinjecting eggs," *Proc. Natl. Acad. Sci. USA* 82:4438–4442 (1985).

Brown, "Cloning and characterization of an extracellular $Ca^{2+}$ –sensing receptor from bovine parathyroid," *Nature* 366:575–580 (1993).

Bruno et al., "Protective effect of the metabotropic glutamate receptor agonist, DCG–IV, against excitotoxic neuronal death," *Euro. J. Pharmacol.* 256:109–112 (1994).

Buck and Axel, "A Novel Multigene Family May Encode Odorant Receptors: A Molecular Basis for Odor Recognition," *Cell* 65:175–187 (1991).

Flor et al., "Molecular Cloning, Functional Expression and Pharmacological Characterization of the Human Metabotropic Glutamate Receptor Type 2" *Journal of Neuroscience* 7:622–629 (1995).

SEQUENCE ID No. 1
SEQUENCE RANGE: 1 TO 908

```
         10         20         30         40         50         60         70
          *          *          *          *          *          *          *
MVCEGKRSAS CPCFFLLTAK FYWILTMMQR THSQEYAHSI RVDGDIILGG LFPVHAKGER GVPCGELKKE 80         90        100        110        120        130        140
          *          *          *          *          *          *          *
KGIHRLEAML YAIDQINKDP DLLSNITLGV RILDTCSRDT YALEQSLTFV QALIEKDASD VKCANGDPPI 150        160        170        180        190        200        210
          *          *          *          *          *          *          *
FTKPDKISGV IGAAASSVSI MVANILRLFK IPQISYASTA PELSDNTRYD FFSRVVPPDS YQAQAMVDIV 220        230        240        250        260        270        280
          *          *          *          *          *          *          *
TALGWNYVST LASEGNYGES GVEAFTQISR EIGGVCIAQS QKIPREPRPG EFEKIIKRLL ETPNARAVIM 290        300        310        320        330        340        350
          *          *          *          *          *          *          *
FANEDDIRRI LEAAKKLNQS GHFLWIGSDS WGSKIAPVYQ QEEIAEGAVT ILPKRASIDG FDRYFRSRTL 360        370        380        390        400        410        420
          *          *          *          *          *          *          *
ANNRRNVWFA EFWEENFGCK LGSHGKRNSH IKKCTGLERI ARDSSYEQEG KVQFVIDAVY SMAYALHNMH 430        440        450        460        470        480        490
          *          *          *          *          *          *          *
KDLCPGYIGL CPRMSTIDGK ELLGYIRAVN FNGSAGTPVT FNENGDAPGR YDIFQYQITN KSTEYKVIGH 500        510        520        530        530        550        560
          *          *          *          *          *          *          *
WTNQLHLKVE DMQWAHREHT HPASVCSLPC KPGERKKTVK GVPCCWHCER CEGYNYQVDE LSCELCPLDQ 570        580        590        600        610        620        630
          *          *          *          *          *          *          *
RPNMNRTGCQ LIPIIKLEWH SPWAVVPVFV AILGIIATTF VIVTFVRYND TPIVRASGRE LSYVLLTGIF 640        650        660        670        680        690        700
          *          *          *          *          *          *          *
LCYSITFLMI AAPDTIICSF RRVFLGLGMC FSYAALLTKT NRIHRIFEQG KKSVTAPKFI SPASQLVITF 710        720        730        740        750        760        770
          *          *          *          *          *          *          *
SLISVQLLGV FVWFVVDPPH IIIDYGEQRT LDPEKARGVL KCDISDLSLI CSLGYSILLM VTCTVYAIKT 780        790        800        810        820        830        840
          *          *          *          *          *          *          *
RGVPETFNEA KPIGFTMYTT CIIWLAFIPI FFGTAQSAEK MYIQTTTLTV SMSLSASVSL GMLYMPKVYI 850        860        870        880        890        900
          *          *          *          *          *          *
IIFHPEQNVQ KRKRSFKAVV TAATMQSKLI QKGNDRPNGE VKSELCESLE TNSKSSVEFP MVKSGSTS
```

Fig. 1

SEQUENCE ID No.2
SEQUENCE RANGE:-515 TO 3318

```
          -506       -496       -486       -476       -466       -456
            *          *          *          *          *          *
      GCGGCCGCCG GTGGGAGTAT TTGTTATTCA CATGGAAGAG ACTTGGCGCC TGCTAGGCCA

-446       -436       -426       -416       -406       -396
            *          *          *          *          *          *
      GCTCAGCCCC CTCAGCCCAG AGATCAGCCA CAAGTGCGGC CGCTGTGCTC GCCTCACGCG

-386       -376       -366       -356       -346       -336
            *          *          *          *          *          *
      GCGGCGGCGG CGGCGGCGGC GGCCGTGACA TGGAGCTGCG GGCCCCGGC GGGCTTCCTC

-326       -316       -306       -296       -286       -276
            *          *          *          *          *          *
      ACCGCGCCCT CTGCGGGGAG CAGGGAATAA TTCTGCTACA AGGCTGATTT CAAGGACATG

-266       -256       -246       -236       -226       -216
            *          *          *          *          *          *
      AATTGTTGAC CTCATCCCAA CATCAGAACC TCAGATGTTC TAATTTTTGC ACCATTCCAG

-206       -196       -186       -176       -166       -156
            *          *          *          *          *          *
      GCAAGTTGAT CTTATAAGGA AATAAAATTG AACCTTAGGG GTCTGATGGA AATTCACTGT

-146       -136       -126       -116       -106        -96
            *          *          *          *          *          *
      GACATTCAAA TCAAGAAAAC TTGCTAATGC CCACAGAGCC TTTTCCCCAT GGGCCCTGAT

-86        -76        -66        -56        -46        -36
            *          *          *          *          *          *
      GGTAGCCTCC AGAAGGTGCA GCCTCAGGTG GTGCCCTTTC TTCTGTGGCA AGAATAAACT

-26        -16         -6          5         15         25
            *          *          *          *          *          *
      TTGGGTCTTG GATTGCAATA CCACCTGTGG AGAAAATGGT ATGCGAGGGA AAGCGATCAG 35         45         55         65         75         85
            *          *          *          *          *          *
      CCTCTTGCCC TTGTTTCTTC CTCTTGACCG CCAAGTTCTA CTGGATCCTC ACAATGATGC 95        105        115        125        135        145
            *          *          *          *          *          *
      AAAGAACTCA CAGCCAGGAG TATGCCCATT CCATACGGGT GGATGGGGAC ATTATTTTGG 155        165        175        185        195        205
            *          *          *          *          *          *
      GGGGTCTCTT CCCTGTCCAC GCAAAGGGAG AGAGAGGGGT GCCTTGTGGG GAGCTGAAGA 215        225        235        245        255        265
            *          *          *          *          *          *
      AGGAAAAGGG GATTCACAGA CTGGAGGCCA TGCTTTATGC AATTGACCAG ATTAACAAGG
```

Fig. 2A

SEQUENCE ID No.2
(CONTINUED)

```
          275        285        295        305        315        325
           *          *          *          *          *          *
     ACCCTGATCT CCTTTCCAAC ATCACTCTGG GTGTCCGCAT CCTCGACACG TGCTCTAGGG 335        345        355        365        375        385
           *          *          *          *          *          *
     ACACCTATGC TTTGGAGCAG TCTCTAACAT TCGTGCAGGC ATTAATAGAG AAAGATGCTT 395        405        415        425        435        445
           *          *          *          *          *          *
     CGGATGTGAA GTGTGCTAAT GGAGATCCAC CCATTTTCAC CAAGCCCGAC AAGATTTCTG 455        465        475        485        495        505
           *          *          *          *          *          *
     GCGTCATAGG TGCTGCAGCA AGCTCCGTGT CCATCATGGT TGCTAACATT TTAAGACTTT 515        525        535        545        555        565
           *          *          *          *          *          *
     TTAAGATACC TCAAATCAGC TATGCATCCA CAGCCCCAGA GCTAAGTGAT AACACCAGGT 575        585        595        605        615        625
           *          *          *          *          *          *
     ATGACTTTTT CTCTCGAGTG GTTCCGCCTG ACTCCTACCA AGCCCAAGCC ATGGTGGACA 635        645        655        665        675        685
           *          *          *          *          *          *
     TCGTGACAGC ACTGGGATGG AATTATGTTT CGACACTGGC TTCTGAGGGG AACTATGGTG 695        705        715        725        735        745
           *          *          *          *          *          *
     AGAGCGGTGT GGAGGCCTTC ACCCAGATCT CGAGGGAGAT TGGTGGTGTT TGCATTGCTC 755        765        775        785        795        805
           *          *          *          *          *          *
     AGTCACAGAA AATCCCACGT GAACCAAGAC CTGGAGAATT TGAAAAAATT ATCAAACGCC 815        825        835   -    845        855        865
           *          *          *          *          *          *
     TGCTAGAAAC ACCTAATGCT CGAGCAGTGA TTATGTTTGC CAATGAGGAT GACATCAGGA 875        885        895        905        915        925
           *          *          *          *          *          *
     GGATATTGGA AGCAGCAAAA AAACTAAACC AAAGTGGGCA TTTTCTCTGG ATTGGCTCAG 935        945        955        965        975        985
           *          *          *          *          *          *
     ATAGTTGGGG ATCCAAAATA GCACCTGTCT ATCAGCAAGA GGAGATTGCA GAAGGGGCTG 995       1005       1015       1025       1035       1045
           *          *          *          *          *          *
     TGACAATTTT GCCCAAACGA GCATCAATTG ATGGATTTGA TCGATACTTT AGAAGCCGAA
```

Fig. 2B

SEQUENCE ID No.2
(CONTINUED)

```
             1055       1065       1075       1085       1095       1105
               *          *          *          *          *          *
           CTCTTGCCAA TAATCGAAGA AATGTGTGGT TTGCAGAATT CTGGGAGGAG AATTTTGGCT 1115       1125       1135       1145       1155       1165
               *          *          *          *          *          *
           GCAAGTTAGG ATCACATGGG AAAAGGAACA GTCATATAAA GAAATGCACA GGGCTGGAGC 1175       1185       1195       1205       1215       1225
               *          *          *          *          *          *
           GAATTGCTCG GGATTCATCT TATGAACAGG AAGGAAAGGT CCAATTTGTA ATTGATGCTG 1235       1245       1255       1265       1275       1285
               *          *          *          *          *          *
           TATATTCCAT GGCTTACGCC CTGCACAATA TGCACAAAGA TCTCTGCCCT GGATACATTG 1295       1305       1315       1325       1335       1345
               *          *          *          *          *          *
           GCCTTTGTCC ACGAATGAGT ACCATTGATG GGAAAGAGCT ACTTGGTTAT ATTCGGGCTG 1355       1365       1375       1385       1395       1405
               *          *          *          *          *          *
           TAAATTTTAA TGGCAGTGCT GGCACTCCTG TCACTTTTAA TGAAAACGGA GATGCTCCTG 1415       1425       1435       1445       1455       1465
               *          *          *          *          *          *
           GACGTTATGA TATCTTCCAG TATCAAATAA CCAACAAAAG CACAGAGTAC AAAGTCATCG 1475       1485       1495       1505       1515       1525
               *          *          *          *          *          *
           GCCACTGGAC CAATCAGCTT CATCTAAAAG TGGAAGACAT GCAGTGGGCT CATAGAGAAC 1535       1545       1555       1565       1575       1585
               *          *          *          *          *          *
           ATACTCACCC GGCGTCTGTC TGCAGCCTGC CGTGTAAGCC AGGGGAGAGG AAGAAAACGG 1595       1605       1615       1625       1635       1645
               *          *          *          *          *          *
           TGAAAGGGGT CCCTTGCTGC TGGCACTGTG AACGCTGTGA AGGTTACAAC TACCAGGTGG 1655       1665       1675       1685       1695       1705
               *          *          *          *          *          *
           ATGAGCTGTC CTGTGAACTT TGCCCTCTGG ATCAGAGACC CAACATGAAC CGCACAGGCT 1715       1725       1735       1745       1755       1765
               *          *          *          *          *          *
           GCCAGCTTAT CCCCATCATC AAATTGGAGT GGCATTCTCC CTGGGCTGTG GTGCCTGTGT 1775       1785       1795       1805       1815       1825
               *          *          *          *          *          *
           TTGTTGCAAT ATTGGGAATC ATCGCCACCA CCTTTGTGAT CGTGACCTTT GTCCGCTATA 1835       1845       1855       1865       1875       1885
               *          *          *          *          *          *
           ATGACACACC TATCGTGAGG GCTTCAGGAC GCGAACTTAG TTACGTGCTC CTAACGGGGA
```

Fig.2C

SEQUENCE ID No.2
(CONTINUED)

```
           1895       1905       1915       1925       1935       1945
            *          *          *          *          *          *
        TTTTTCTCTG TTATTCAATC ACGTTTTTAA TGATTGCAGC ACCAGATACA ATCATATGCT 1955       1965       1975       1985       1995       2005
            *          *          *          *          *          *
        CCTTCCGACG GGTCTTCCTA GGACTTGGCA TGTGTTTCAG CTATGCAGCC CTTCTGACCA 2015       2025       2035       2045       2055       2065
            *          *          *          *          *          *
        AAACAAACCG TATCCACCGA ATATTTGAGC AGGGGAAGAA ATCTGTCACA GCGCCCAAGT 2075       2085       2095       2105       2115       2125
            *          *          *          *          *          *
        TCATTAGTCC AGCATCTCAG CTGGTGATCA CCTTCAGCCT CATCTCCGTC CAGCTCCTTG 2135       2145       2155       2165       2175       2185
            *          *          *          *          *          *
        GAGTGTTTGT CTGGTTTGTT GTGGATCCCC CCCACATCAT CATTGACTAT GGAGAGCAGC 2195       2205       2215       2225       2235       2245
            *          *          *          *          *          *
        GGACACTAGA TCCAGAGAAG GCCAGGGGAG TGCTCAAGTG TGACATTTCT GATCTCTCAC 2255       2265       2275       2285       2295       2305
            *          *          *          *          *          *
        TCATTTGTTC ACTTGGATAC AGTATCCTCT TGATGGTCAC TTGTACTGTT TATGCCATTA 2315       2325       2335       2345       2355       2365
            *          *          *          *          *          *
        AAACGAGAGG TGTCCCAGAG ACTTTCAATG AAGCCAAACC TATTGGATTT ACCATGTATA 2375       2385       2395       2405       2415       2425
            *          *          *          *          *          *
        CCACCTGCAT CATTTGGTTA GCTTTCATCC CCATCTTTTT TGGTACAGCC CAGTCAGCAG 2435       2445       2455       2465       2475       2485
            *          *          *          *          *          *
        AAAAGATGTA CATCCAGACA ACAACACTTA CTGTCTCCAT GAGTTTAAGT GCTTCAGTAT 2495       2505       2515       2525       2535       2545
            *          *          *          *          *          *
        CTCTGGGCAT GCTCTATATG CCCAAGGTTT ATATTATAAT TTTTCATCCA GAACAGAATG 2555       2565       2575       2585       2595       2605
            *          *          *          *          *          *
        TTCAAAAACG CAAGAGGAGC TTCAAGGCTG TGGTGACAGC TGCCACCATG CAAAGCAAAC 2615       2625       2635       2645       2655       2665
            *          *          *          *          *          *
        TGATCCAAAA AGGAAATGAC AGACCAAATG GCGAGGTGAA AAGTGAACTC TGTGAGAGTC 2675       2685       2695       2705       2715       2725
            *          *          *          *          *          *
        TTGAAACCAA CAGTAAGTCA TCTGTAGAGT TTCCGATGGT CAAGAGCGGG AGCACTTCCT
```

Fig. 2D

SEQUENCE ID No.2
(CONTINUED)

```
        2735       2745       2755       2765       2775       2785
          *          *          *          *          *          *
    AATAGATCTT CCTCTACCAA GACAACATAT ATCAGTTACA GCAATCATTC AATCTGAAAC 2795       2805       2815       2825       2835       2845
          *          *          *          *          *          *
    AGGGAAATGG CACAATCTGA AGAGACGTGG TATATGATCT TAAATGATGA ACATGAGACC 2855       2865       2875       2885       2895       2905
          *          *          *          *          *          *
    GCAAAAATTC ACTCCTGGAG ATCTCCGTAG ACTACAATCA ATCAAATCAA TAGTCAGTCT 2915       2925       2935       2945       2955       2965
          *          *          *          *          *          *
    TGTAAGGAAC AAAAATTAGC CATGAGCCAA AAGTATCAAT AAACGGGGAG TGAAGAAACC 2975       2985       2995       3005       3015       3025
          *          *          *          *          *          *
    CGTTTTATAC AATAAAACCA ATGAGTGTCA AGCTAAAGTA TTGCTTATTC ATGAGCAGTT 3035       3045       3055       3065       3075       3085
          *          *          *          *          *          *
    AAAACAAATC ACAAAAGGAA AACTAATGTT AGCTCGTGAA AAAAATGCTG TTGAAATAAA 3095       3105       3115       3125       3135       3145
          *          *          *          *          *          *
    TAATGTCTGA TGTTATTCTT GTATTTTTCT GTGATTGTGA GAACTCCCGT TCCTGTCCCA 3155       3165       3175       3185       3195       3205
          *          *          *          *          *          *
    CATTGTTTAA CTTGTATAAG ACAATGAGTC TGTTTCTTGT AATGGCTGAC CAGATTGAAG 3215       3225       3235       3245       3255       3265
          *          *          *          *          *          *
    CCCTGGGTTG TGCTAAAAAT AAATGCAATG ATTGATGCAT GCAATTTTTT ATACAAATAA 3275       3285       3295       3305       3315
          *          *          *          *          *
    TTTATTTCTA ATAATAAAGG AATGTTTTGC AAATGTTAAA AAAAAAAAAA AAA
```

Fig. 2E

SEQUENCE ID No.3
SEQUENCE RANGE 1 TO 166

```
          10         20         30         40         50
           *          *          *          *          *
    CCCCCACATC TACATTGACT ATGGAGAGCA GCGGACACTA GATCCAGAGA 60         70         80         90        100
           *          *          *          *          *
    AGGCCAGGGG AGTGCTCAAG TGTGACATTT CTGATCTCTC ACTCATTTGT 110        120        130        140        150
           *          *          *          *          *
    TCACTTGGAT ACAGTATCCT CTTGATGGTC ACTTCTACTG TTTATGCCAT

160
           *
    TAAAACGAGA GGTGTC
```

Fig. 3

SEQUENCE ID No.4
SEQUENCE RANGE 1 TO 121

```
          10         20         30         40         50
           *          *          *          *          *
     CTACATTGAC TATGGAGAGC AGCGNACACT AGATCCAGAG AAGGCCAGGG 60         70         80         90        100
           *          *          *          *          *
     GAGTGCTCAA GTGTGACATT TCTGATCTCT CACTCATTTG TTCACTTGGA 110        120
           *          *
     TACAGTATCC TCTTGATGGT C
```

Fig. 4

SEQUENCE ID No.5
SEQUENCE RANGE 1 TO 2724

```
         10         20         30         40         50         60         70         80         90        100
          *          *          *          *          *          *          *          *          *          *
    ATGGTATGCG AGGGAAAGCG ATCAGCCTCT TGCCCTTGTT TCTTCCTCTT GACCGCCAAG TTCTACTGGA TCCTCACAAT GATGCAAAGA ACTCACAGCC 110        120        130        140        150        160        170        180        190        200
          *          *          *          *          *          *          *          *          *          *
    AGGAGTATGC CCATTCCATA CGGGTGGATG GGGACATTAT TTTGGGGGGT CTCTTCCCTG TCCACGCAAA GGGAGAGAGA GGGGTGCCTT GTGGGGAGCT 210        220        230        240        250        260        270        280        290        300
          *          *          *          *          *          *          *          *          *          *
    GAAGAAGGAA AAGGGGATTC ACAGACTGGA GGCCATGCTT TATGCAATTG ACCAGATTAA CAAGGACCCT GATCTCCTTT CCAACATCAC TCTGGGTGTC 310        320        330        340        350        360        370        380        390        400
          *          *          *          *          *          *          *          *          *          *
    CGCATCCTCG ACACGTGCTC TAGGGACACC TATGCTTTGG AGCAGTCTCT AACATTCGTG CAGGCATTAA TAGAGAAAGA TGCTTCGGAT GTGAAGTGTG 410        420        430        440        450        460        470        480        490        500
          *          *          *          *          *          *          *          *          *          *
    CTAATGGAGA TCCACCCATT TTCACCAAGC CCGACAAGAT TTCTGGCGTC ATAGGTGCTG CAGCAAGCTC CGTGTCCATC ATGGTTGCTA ACATTTTAAG 510        520        530        540        550        560        570        580        590        600
          *          *          *          *          *          *          *          *          *          *
    ACTTTTTAAG ATACCTCAAA TCAGCTATGC ATCCACAGCC CCAGAGCTAA GTGATAACAC CAGGTATGAC TTTTTCTCTC GAGTGGTTCC GCCTGACTCC 610        620        630        640        650        660        670        680        690        700
          *          *          *          *          *          *          *          *          *          *
    TACCAAGCCC AAGCCATGGT GGACATCGTG ACAGCACTGG GATGGAATTA TGTTTCGACA CTGGCTTCTG AGGGGAACTA TGGTGAGAGC GGTGTGGAGG 710        720        730        740        750        760        770        780        790        800
          *          *          *          *          *          *          *          *          *          *
    CCTTCACCCA GATCTCGAGG GAGATTGGTG GTGTTTGCAT TGCTCAGTCA CAGAAAATCC CACGTGAACC AAGACCTGGA GAATTTGAAA AAATTATCAA
```

Fig. 5A

SEQUENCE ID No.5
(CONTINUED)

```
          810        820        830        840        850        860        870        880        890        900
           *          *          *          *          *          *          *          *          *          *
ACGCCTGCTA GAAACACCTA ATGCTCGAGC AGTGATTATG TTTGCCAATG AGGATGACAT CAGGAGGATA TTGGAAGCAG CAAAAAAACT AAACCAAAGT 910        920        930        940        950        960        970        980        990       1000
           *          *          *          *          *          *          *          *          *          *
GGGCATTTTC TCTGGATTGG CTCAGATAGT TGGGGATCCA AAATAGCACC TGTCTATCAG CAAGAGGAGA TTGCAGAAGG GGCTGTGACA ATTTTGCCCA 1010       1020       1030       1040       1050       1060       1070       1080       1090       1100
           *          *          *          *          *          *          *          *          *          *
AACGAGCATC AATTGATGGA TTTGATCGAT ACTTTAGAAG CCGAACTCTT GCCAATAATC GAAGAAATGT GTGGTTTGCA GAATTCTGGG AGGAGAATTT 1110       1120       1130       1140       1150       1160       1170       1180       1190       1200
           *          *          *          *          *          *          *          *          *          *
TGGCTGCAAG TTAGGATACAC ATGGGAAAAG GAACAGTCAT ATAAAGAAAT GCACAGGGCT GGAGCGAATT GCTCGGGATT CATCTTATGA ACAGGAAGGA 1210       1220       1230       1240       1250       1260       1270       1280       1290       1300
           *          *          *          *          *          *          *          *          *          *
AAGGTCCAAT TTGTAATTGA TGCTGTATAT TCCATGGCTT ACGCCCTGCA CAATATGCAC AAAGATCTCT GCCCTGGATA CATTGGCCTT TGTCCACGAA 1310       1320       1330       1340       1350       1360       1370       1380       1390       1400
           *          *          *          *          *          *          *          *          *          *
TGAGTACCAT TGATGGGAAA GAGCTACTTG GTTATATTCG GGCTGTAAAT TTTAATGGCA GTGCTGGCAC TCCTGTCACT TTTAATGAAA ACGGAGATGC 1410       1420       1430       1440       1450       1460       1470       1480       1490       1500
           *          *          *          *          *          *          *          *          *          *
TCCTGGACGT TATGATATCT TCCAGTATCA AATAACCAAC AAAAGCACAG AGTACAAAGT CATCGGCCAC TGGACCAATC AGCTTCATCT AAAAGTGGAA 1510       1520       1530       1540       1550       1560       1570       1580       1590       1600
           *          *          *          *          *          *          *          *          *          *
GACATGCAGT GGGCTCATAG AGAACATACT CACCCGGGCGT CTGTCTGCAG CCTGCCGTGT AAGCCAGGGG AGAGGAAGAA AACGGTGAAA GGGGTCCCTT
```

Fig. 5B

SEQUENCE ID No.5
(CONTINUED)

```
          1610       1620       1630       1640       1650       1660       1670       1680       1690       1700
            *          *          *          *          *          *          *          *          *          *
         GCTGCTGGCA CTGTGAACGC TGTGAAGGTT ACAACTACCA GGTGGATGAG CTGTCCTGTG AACTTTGCCC TCTGGATCAG AGACCCAACA TGAACCGCAC 1710       1720       1730       1740       1750       1760       1770       1780       1790       1800
            *          *          *          *          *          *          *          *          *          *
         AGGCTGCCAG CTTATCCCCA TCATCAAATT GGAGTGGCAT TCTCCCTGGG CTGTGGTGCC TGTGTTTGTT GCAATATTGG GAATCATCGC CACCACCTTT 1810       1820       1830       1840       1850       1860       1870       1880       1890       1900
            *          *          *          *          *          *          *          *          *          *
         GTGATCGTGA CCTTTGTCCG CTATAATGAC ACACCCTATCG TGAGGGCTTC AGGACGCGAA CTTAGTTACG TGCTCCTAAC GGGGATTTTT CTCTGTTATT 1910       1920       1930       1940       1950       1960       1970       1980       1990       2000
            *          *          *          *          *          *          *          *          *          *
         CAATCACGTT TTTAATGATT GCAGCACCAG ATACAATCAT ATGCTCCTTC CGACGGGTCT TCCTAGGACT TGGCATGTGT TTCAGCTATG CAGCCCTTCT 2010       2020       2030       2040       2050       2060       2070       2080       2090       2100
            *          *          *          *          *          *          *          *          *          *
         GACCAAAACA AACCGTATCC ACCGAATATT TGAGCAGGGG AAGAAATCTG TCACAGGCC CAAGTTCATT AGTCCAGCAT CTCAGCTGGT GATCACCTTC 2110       2120       2130       2140       2150       2160       2170       2180       2190       2200
            *          *          *          *          *          *          *          *          *          *
         AGCCTCATCT CCGTCCAGCT CCTTGGAGTG TTTGTCTGGT TTGTTGTGGA TCCCCCCAC ATCATCATTG ACTATGGAGA GCAGCGGACA CTAGATCCAG 2210       2220       2230       2240       2250       2260       2270       2280       2290       2300
            *          *          *          *          *          *          *          *          *          *
         AGAAGGCCAG GGGAGTGCTC AAGTGTGACA TTTCTGATCT CTCACTCATT TGTTCACTTG GATACAGTAT CCTCTTGATG GTCACTTGTA CTGTTTATGC 2310       2320       2330       2340       2350       2360       2370       2380       2390       2400
            *          *          *          *          *          *          *          *          *          *
         CATTAAAACG AGAGGTGTCC CAGAGACTTT CAATGAAGCC AAACCTATTG GATTTACCAT GTATACCACC TGCATCATTT GGTTAGCTTT CATCCCCATC
```

Fig. 5C

SEQUENCE ID No.5
(CONTINUED)

```
         2410       2420       2430       2440       2450       2460       2470       2480       2490       2500
           *          *          *          *          *          *          *          *          *          *
TTTTTTGGTA CAGCCCAGTC AGCAGAAAAG ATGTACATCC AGACAACAAC ACTTACTGTC TCCATGAGTT TAAGTGCTTC AGTATCTCTG GGCATGCTCT
         2510       2520       2530       2540       2550       2560       2570       2580       2590       2600
           *          *          *          *          *          *          *          *          *          *
ATATGCCCAA GGTTTATATT ATAATTTTTC ATCCAGAACA GAATGTTCAA AAACGCAAGA GGAGCTTCAA GGCTGTGGTG ACAGCTGCCA CCATGCAAAG
         2610       2620       2630       2640       2650       2660       2670       2680       2690       2700
           *          *          *          *          *          *          *          *          *          *
CAAACTGATC CAAAAAGGAA ATGCAGACC AAATGGCGAG GTGAAAAGTG AACTCTGTGA GAGTCTTGAA ACCAACAGTA AGTCATCTGT AGAGTTTCCG
         2710       2720
           *          *
ATGGTCAAGA GCGGGAGCAC TTCC
```

Fig. 5D

FIG. 7.
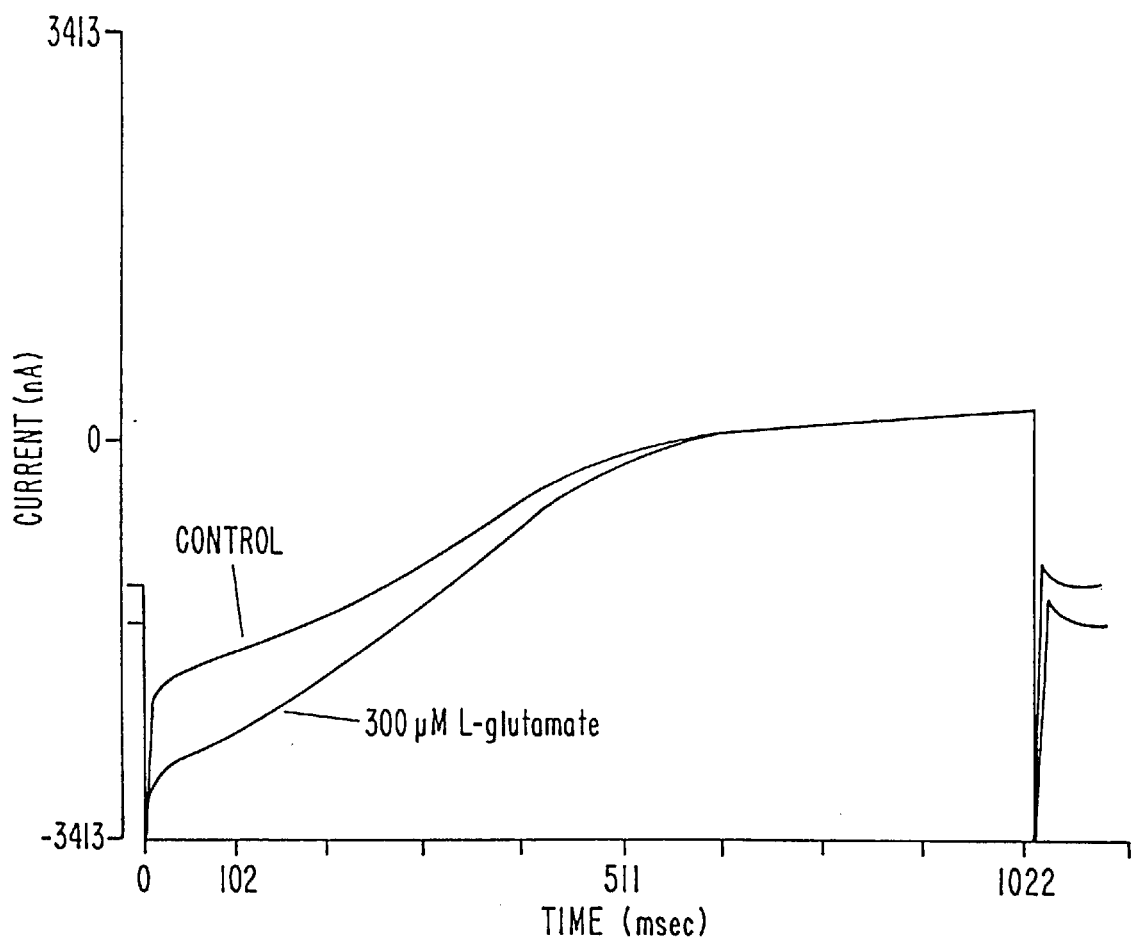
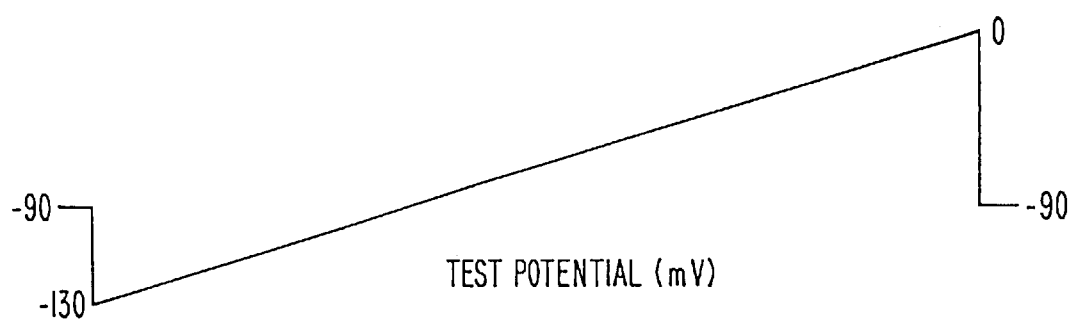

ISOLATED HUMAN METABOTROPIC GLUTAMATE RECEPTOR MGLUR-8

This is a division of application Ser. No. 08/604,298 filed Feb. 21, 1996.

FIELD OF THE INVENTION

The present invention relates to nucleic acid sequences coding for a novel human metabotropic glutamate receptor (mGluR). The novel human receptor may be expressed in host cells which may be used to screen for agonist, antagonist, and modulatory molecules that act on the novel human mGluR. These molecules acting on the novel human mGluR can be used to modulate the activity of the novel human receptor for the treatment of neurological disorders and diseases.

The invention also relates to nucleic acids encoding such receptors; genetically modified cells, tissues and animals containing such nucleic acids; antibodies to such receptors; and methods relating to all of the foregoing.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to that invention.

Glutamate is the major excitatory neurotransmitter in the mammalian central nervous system (CNS). Glutamate produces its effects on central neurons by binding to and thereby activating cell surface receptors. These receptors have been subdivided into two major classes, the ionotropic and metabotropic glutamate receptors, based on the structural features of the receptor proteins, the means by which the receptors transduce signals into the cell, and pharmacological profiles.

The ionotropic glutamate receptors (iGluRs) are ligand-gated ion channels that upon binding glutamate, open to allow the selective influx of certain monovalent and divalent cations, thereby depolarizing the cell membrane. In addition, certain iGluRs with relatively high calcium permeability can activate a variety of calcium-dependent intracellular processes. These receptors are multisubunit protein complexes that may be homomeric or heteromeric in nature. The various iGluR subunits all share common structural motifs, including a relatively large amino-terminal extracellular domain (ECD), followed by two transmembrane domains (TMD), a second smaller extracellular domain, and a third TMD, before terminating with an intracellular carboxy-terminal domain. Historically the iGluRs were first subdivided pharmacologically into three classes based on preferential activation by the agonists α-amino-3-hydroxy-5-methylisoxazole-4-propionic acid (AMPA), kainate (KA), and N-methyl-D-aspartate (NMDA). Later, molecular cloning studies coupled with additional pharmacological studies revealed a greater diversity of iGluRs, in that multiple subtypes of AMPA, KA and NMDA receptors are expressed in the mammalian CNS (Hollman and Heinemann, *Ann. Rev. Neurosci* 17:31, 1994).

The metabotropic glutamate receptors (mGluRs) are G protein-coupled receptors capable of activating a variety of intracellular second messenger systems following the binding of glutamate. Activation of mGluRs in intact mammalian neurons can elicit one or more of the following responses: activation of phospholipase C, increases in phosphoinositide (PI) hydrolysis, intracellular calcium release, activation of phospholipase D, activation or inhibition of adenylyl cyclase, increases or decreases in the formation of cyclic adenosine monophosphate (cAMP), activation of guanylyl cyclase, increases in the formation of cyclic guanosine monophosphate (cGMP), activation of phospholipase $A_2$, increases in arachidonic acid release, and increases or decreases in the activity of ion channels (e.g., voltage- and ligand-gated ion channels (Schoepp and Conn, *Trends Pharmacol. Sci.* 14:13, 1993; Schoepp, *Neurochem. Int.* 24:439, 1994; Pin and Duvoisin, *Neuropharmacology* 34:1, 1995).

Thus far, eight distinct mGluR subtypes have been isolated via molecular cloning, and named mGluR1 to mGluR8 according to the order in which they were discovered (Nakanishi, *Neuron* 13:1031, 1994; Pin and Duvoisin, *Neuropharmacology* 34:1, 1995; Knopfel et al., *J. Med. Chem.* 38:1417, 1995). Further diversity occurs through the expression of alternatively spliced forms of certain mGluR subtypes (Pin et al., *PNAS* 89:10331, 1992; Minakami et al., *BBRC* 199:1136, 1994; Joly et al., *J. Neurosci* 15:3970, 1995). All of the mGluRs are structurally similar, in that they are single subunit membrane proteins possessing a large amino-terminal ECD, followed by seven putative TMDs, and an intracellular carboxy-terminal domain of variable length.

The eight mGluRs have been subdivided into three groups based on amino acid sequence homologies, the second messenger systems they utilize, and pharmacological characteristics (Nakanishi, *Neuron* 13:1031, 1994; Pin and Duvoisin, *Neuropharmacology* 34:1, 1995; Knopfel et al., *J. Med Chem.* 38:1417, 1995). The amino acid homology between mGluRs within a given group is approximately 70%, but drops to about 40% between mGluRs in different groups. For mGluRs in the same group, this relatedness is roughly paralleled by similarities in signal transduction mechanisms, and pharmacological characteristics.

The Group I mGluRs comprise mGluR1, mGluR5 and their alternatively spliced variants. The binding of agonists to these receptors results in the activation of phospholipase C and the subsequent mobilization of intracellular calcium. For example, Xenopus oocytes expressing recombinant mGluR1 receptors have been utilized to demonstrate this effect indirectly by electrophysiological means (Masu et al., *Nature* 349:760,1991; Pin etal., *PNAS* 89:10331,1992). Similar results were achieved with oocytes expressing recombinant mGluR5 receptors (Abe et al., *J. Biol. Chem.* 267:13361, 1992; Minakami et al., *BBRC* 199:1136, 1994; Joly et al., *J. Neurosci.* 15:3970, 1995). Alternatively, agonist activation of recombinant mGluR1 receptors expressed in Chinese hamster ovary (CHO) cells stimulated PI hydrolysis, cAMP formation, and arachidonic acid release as measured by standard biochemical assays (Aramori and Nakanishi, *Neuron* 8:757, 1992). In comparison, activation of mGluR5 receptors expressed in CHO cells stimulated PI hydrolysis and subsequent intracellular calcium transients, but no stimulation of cAMP formation or arachidonic acid release was observed (Abe et al., *J. Biol. Chem.* 267:13361, 1992). However, activation of mGluR5 receptors expressed in LLC-PK1 cells does result in increased cAMP formation as well as PI hydrolysis (Joly et al., *J. Neurosci.* 15:3970, 1995). The agonist potency profile for Group I mGluRs is quisqualate>glutamate=ibotenate>(2S,1'S,2'S)-2-carboxycyclopropyl)glycine (L-CCG-I)>(1S,3R)-1-aminocyclopentane-1,3-dicarboxylic acid (ACPD). Quisqualate is relatively selective for Group I receptors, as compared to Group II and Group III mGluRs, but it also potently activates ionotropic AMPA receptors (Pin and Duvoisin, *Neuropharmacology* 34: 1, Knopfel et al., *J. Med. Chem.* 38:1417, 1995).

The Group II mGluRs include mGluR2 and mGluR3. Activation of these receptors as expressed in CHO cells inhibits adenylyl cyclase activity via the inhibitory G protein, $G_i$, in a pertussis toxin-sensitive fashion (Tanabe et al., *Neuron* 8:169, 1992; Tanabe et al., *J. Neurosci.* 13:1372, 1993). The agonist potency profile for Group II receptors is L-CCG-I>glutamate>ACPD>ibotenate>quisqualate. Preliminary studies suggest that L-CCG-I and (2S,1'R,2'R,3'R)-2-(2,3-dicarboxycyclopropyl)glycine (DCG-IV) are both relatively selective agonists for the Group II receptors versus other mGluRs (Knopfel et al., *J. Med Chem.* 38:1417, 1995), but DCG-IV does exhibit agonist activity at iGluRs as well (Ishida et al., *Br. J Pharmacol.* 109:1169, 1993).

The Group III mGluRs include mGluR4, mGluR6, mGluR7 and mGluR8. Like the Group II receptors these mGluRs are negatively coupled to adenylyl cyclase to inhibit intracellular cAMP accumulation in a pertussis toxin-sensitive fashion when expressed in CHO cells (Tanabe et al., *J. Neurosci.* 13:1372, 1993; Nakajima et al., *J. Biol. Chem.* 268:11868, 1993; Okamoto et al., *J. Biol. Chem.* 269: 1231, 1994; Duvoisin et al., *J. Neurosci.* 15:3075, 1995). As a group, their agonist potency profile is (S)-2-amino-4-phosphonobutyric acid (L-AP4) >glutamate>ACPD>quisqualate, but mGluR8 may differ slightly with glutamate being more potent than L-AP4 (Knopfel et al., *J. Med Chem.* 38:1417, 1995; Duvoisin et al., *J. Neurosci.* 15:3075, 1995). Both L-AP4 and (S)-serine-O-phosphate (L-SOP) are relatively selective agonists for the Group III receptors.

Finally, the eight mGluR subtypes have unique patterns of expression within the mammalian CNS that in many instances are overlapping (Masu et al., *Nature* 349:760, 1991; Martin et al., *Neuron* 9:259, 1992; Ohishi et al., *Neurosci.* 53:1009,1993; Tanabe et al., *J. Neurosci.* 13:1372; Ohishi et al., *Neuron* 13:55, 1994; Abe et al., *J. Biol. Chem.* 267:13361, 1992; Nakajima et al., *J. Biol. Chem.* 268:11868, 1993; Okamoto et al., *J. Biol. Chem.* 269: 1231, 1994; Duvoisin et al., *J. Neurosci.* 15:3075, 1995). As a result certain neurons may express only one particular mGluR subtype, while other neurons may express multiple subtypes that may be localized to similar and/or different locations on the cell (i.e. postsynaptic dendrites and/or cell bodies versus presynaptic axon terminals). Therefore, the functional consequences of mGluR activation on a given neuron will depend on the particular mGluRs being expressed, the receptors' affinities for glutamate and the concentrations of glutamate the cell is exposed to, the signal transduction pathways activated by the receptors, and the locations of the receptors on the cell. A further level of complexity may be introduced by multiple interactions between mGluR-expressing neurons in a given brain region. As a result of these complexities, and the lack of subtype-specific mGluR agonists and antagonists, the roles of particular mGluRs in physiological and pathophysiological processes affecting neuronal function are not well defined. Still, work with the available agonists and antagonists has yielded some general insights about the Group I mGluRs as compared to the Group II and Group III mGluRs.

Attempts at elucidating the physiological roles of Group I mGluRs suggest that activation of these receptors elicits neuronal excitation. Various studies have demonstrated that ACPD can produce postsynaptic excitation upon application to neurons in the hippocampus, cerebral cortex, cerebellum, and thalamus as well as other brain regions. Evidence indicates that this excitation is due to direct activation of postsynaptic mGluRs, but it has also been suggested to be mediated by activation of presynaptic mGluRs resulting in increased neurotransmitter release (Baskys, *Trends Pharmacol. Sci.* 15:92, 1992; Schoepp, *Neurochem. Int.* 24:439, 1994; Pin and Duvoisin, *Neuropharmacology* 34:1). Pharmacological experiments implicate Group I mGluRs as the mediators of this excitation. The effect of ACPD can be reproduced by low concentrations of quisqualate in the presence of iGluR antagonists (Hu and Storm, *Brain Res.* 568:339, 1991; Greene et al., *Eur. J. Pharmacol.* 226:279, 1992), and two phenylglycine compounds known to activate mGluR1, (S)-3-hydroxyphenylglycine ((S)-3HPG) and (S)-3,5-dihydroxyphenylglycine ((S)-DHPG), also produce the excitation (Watkins and Collingridge, *Trends Pharmacol. Sci.* 15:333, 1994). In addition, the excitation can be blocked by (S)-4-carboxyphenylglycine ((S)-4CPG), (S)4-carboxy-3-hydroxyphenylglycine ((S)-4C3HPG) and (+)-alpha-methyl-4-carboxyphenylglycine ((+)-MCPG), compounds known to be mGluR1 antagonists (Eaton et al., *Eur. J. Pharmacol.* 244:195, 1993; Watkins and Collingridge, *Trends Pharmacol. Sci.* 15:333, 1994).

Other studies examining the physiological roles of mGluRs indicate that activation of presynaptic mGluRs can block both excitatory and inhibitory synaptic transmission by inhibiting neurotransmitter release (Pin and Duvoisin, *Neuropharmacology* 34:1). Presynaptic blockade of excitatory synaptic transmission by ACPD has been observed on neurons in the visual cortex, cerebellum, hippocampus, striatum and amygdala (Pin et al., *Curr. Drugs: Neurodegenerative Disorders* 1: 111, 1993), while similar blockade of inhibitory synaptic transmission has been demonstrated in the striatum and olfactory bulb (Calabresi et al., *Neurosci. Lett.* 139:41, 1992; Hayashi et al., *Nature* 366:687, 1993). Multiple pieces of evidence suggest that Group II mGluRs mediate this presynaptic inhibition. Group II mGluRs are strongly coupled to inhibition of adenylyl cyclase, like $\alpha_2$-adrenergic and $5HT_{1A}$-serotonergic receptors which are known to mediate presynaptic inhibition of neurotransmitter release in other neurons. The inhibitory effects of ACPD can also be mimicked by L-CCG-I and DCG-IV, which are selective agonists at Group II mGluRs (Hayashi et al., *Nature* 366:687, 1993; Jane et al., *Br. J. Pharmacol.* 112:809, 1994). Moreover, it has been demonstrated that activation of mGluR2 can strongly inhibit presynaptic, N-type calcium channel activity when the receptor is expressed in sympathetic neurons (Ikeda et al., *Neuron,* 14:1029, 1995), and blockade of these channels is known to inhibit neurotransmitter release. Finally, it has been observed that L-CCG-I, at concentrations selective for Group II mGluRs, inhibits the depolarization-evoked release of $^3$H-aspartate from rat striatal slices (Lombardi et al., *Br. J. Pharmacol.* 110:1407, 1993). Evidence for physiological effects of Group II mGluR activation at the postsynaptic level is limited. However, one study suggests that postsynaptic actions of L-CCG-I can inhibit NMDA receptor activation in cultured mesencephalic neurons (Ambrosini et al., *Mol. Pharmacol.* 47:1057, 1995).

Physiological studies have demonstrated that L-AP4 can also inhibit excitatory synaptic transmission on a variety of CNS neurons. Included are neurons in the cortex, hippocampus, amygdala, olfactory bulb and spinal cord (Koerner and Johnson, *Excitatory Amino Acid Receptors; Design of Agonists and Antagonists* p. 308, 1992; Pin et al., *Curr. Drugs: Neurodegenerative Disorders* 1: 111, 1993). The accumulated evidence indicates that the inhibition is mediated by activation of presynaptic mGluRs. Since the effects of L-AP4 can be mimicked by L-SOP, and these two agonists are selective for Group III mGluRs, members of this mGluR group are implicated as the mediators of the presynaptic inhibition (Schoepp, Neurochem. Int. 24:439, 1994; Pin and Duvoisin, Neuropharmacology 34:1). In olfactory bulb neurons it has been demonstrated that L-AP4 activation of mGluRs inhibits presynaptic calcium currents (Trombley and Westbrook, J. Neurosci. 12:2043, 1992). It is therefore likely that the mechanism of presynaptic inhibition produced by activation of Group III mGluRs is similar to that for Group II mGluRs, i.e. blockade of voltage-dependent calcium channels and inhibition of neurotransmitter release. L-AP4 is also known to act postsynaptically to hyperpolarize ON bipolar cells in the retina. It has been suggested that this action may be due to activation of a mGluR, which is coupled to the cGMP phosphodiesterase in these cells (Schoepp, Neurochem. Int. 24:439, 1994; Pin and Duvoisin, Neuropharmacology 34:1).

Metabotropic glutamate receptors have been implicated as playing roles in a number of normal processes in the mammalian CNS. Activation of mGluRs has been demonstrated to be a requirement for the induction of hippocampal long-term potentiation and cerebellar long-term depression (Bashir et al., Nature 363:347, 1993; Bortolotto et al., Nature 368:740, 1994; Aiba et al., Cell 79:365, 1994; Aiba et al., Cell 79:377, 1994). A role for mGluR activation in nociception and analgesia has also been demonstrated (Meller et al., Neuroreport 4: 879, 1993). In addition, mGluR activation has been suggested to play a modulatory role in a variety of other normal processes including: synaptic transmission, neuronal development, neuronal death, synaptic plasticity, spatial learning, olfactory memory, central control of cardiac activity, waking, motor control, and control of the vestibulo-ocular reflex (for reviews, see Nakanishi, Neuron 13: 1031, 1994; Pin and Duvoisin, Neuropharmacology 34:1; Knopfel et al., J. Med Chem. 38:1417, 1995).

None of the references mentioned herein are admitted to be prior art to the claims.

SUMMARY OF THE INVENTION

The present invention concerns (1) nucleic acids encoding a newly identified metabotropic glutamate receptor protein and fragments thereof; (2) the metabotropic glutamate receptor protein and fragments thereof; (3) chimeric receptor molecules having one or more domains derived from the new metabotropic glutamate receptor and one or more domains derived from a different receptor; (4) cell lines expressing the metabotropic glutamate receptor protein and fragments thereof; (5) antibodies and fragments thereof, targeted to the metabotropic glutamate receptor protein, protein fragments and peptides; (6) uses of such molecules, nucleic acids, proteins, cell lines and antibodies; (7) methods of screening for a compound that binds to or modulates the activity of the metabotropic glutamate receptor; and (8) compounds and methods for modulating the metabotropic glutamate receptor activity and binding to the metabotropic glutamate receptor. Such compounds preferably act as agonists, antagonists, or allosteric modulators of one or more of the metabotropic glutamate receptor activities. By modulating the metabotropic glutamate receptor activities, different effects can be produced, such as anticonvulsant effects, neuroprotectant effects, analgesic effects and cognition-enhancement effects.

Metabotropic glutamate receptors have been suggested to play roles in a variety of pathophysiological processes and disease states affecting the CNS. These include stroke, head trauma, anoxic and ischemic injuries, hypoglycemia, epilepsy, and neurodegenerative diseases such as Alzheimer's disease (Schoepp and Conn, Trends Pharmacol. Sci. 14:13, 1993; Cunningham et al., Life Sci. 54:135, 1994; Hollman and Heinemann, Ann. Rev. Neurosci. 17:31, 1994; Pin and Duvoisin, Neuropharmacology 34:1; Knopfel et al., J. Med. Chem. 38:1417, 1995). Much of the pathology in these conditions is thought to be due to excessive glutamate-induced excitation of CNS neurons. Since Group I mGluRs appear to increase glutamate-mediated neuronal excitation via postsynaptic mechanisms and enhanced presynaptic glutamate release, their activation may contribute to the pathology. Therefore, selective antagonists of these receptors could be therapeutically beneficial, specifically as neuroprotective agents or anticonvulsants. In contrast, since activation of Group II and Group III mGluRs inhibits presynaptic glutamate release and the subsequent excitatory neurotransmission, selective agonists for these receptors might exhibit similar therapeutic utilities. Thus, the various mGluR subtypes may represent novel targets for CNS drug development.

Preliminary studies assessing therapeutic potentials with the available mGluR agonists and antagonists have yielded seemingly contradictory results. For example, it has been reported that application of ACPD onto hippocampal neurons leads to seizures and neuronal damage (Sacaan and Schoepp, Neurosci. Lett. 139:77, 1992; Lipparti et al., Life Sci. 52:85, 1993). But, other studies indicate that ACPD can inhibit epileptiform activity (Taschenberger et al., Neuroreport 3:629, 1992; Sheardown, Neuroreport 3:916, 1992), and can also exhibit neuroprotective properties (Koh et al., Proc. Natl. Acad. Sci. USA 88:9431, 1991; Chiamulera et al., Eur. J. Pharmacol. 216:335, 1992; Siliprandi et al., Eur. J. Pharmacol. 219:173, 1992; Pizzi et al., J. Neurochem. 61:683, 1993). It is likely that these opposing results are due to ACPD's lack of selectivity, and activation of different mGluR subtypes. A reasonable explanation for the results is that Group I mGluRs were activated in the former studies to enhance excitatory neurotransmission, while the latter effects were mediated by activation of Group II and/or Group III mGluRs to inhibit presynaptic glutamate release, and diminish excitatory neurotransmission. The observations that (S)-4C3HPG, a Group I mGluR antagonist and Group II mGluR agonist, protects against audiogenic seizures in DBA/2 mice (Thomsen et al., J. Neurochem. 62:2492, 1994); while the Group II mGluR selective agonists DCG-IV and L-CCG-I protect neurons from NMDA- and KA-induced toxicity (Bruno et al., Eur. J. Pharmacol. 256: 109, 1994; Pizzi et al., J. Neurochem. 61:683, 1993) are also consistent with this interpretation.

It is evident that the currently available mGluR agonists and antagonists may be of limited use, both as research tools and potential therapeutic agents, as a result of their lack of potency and selectivity. In addition, since these compounds are for the most part amino acids or amino acid derivatives, they have limited bioavailabilities which hampers in vivo studies assessing mGluR physiology, pharmacology and therapeutic potential. The identification of agonists and antagonists with a high degree of potency and selectivity for individual mGluR subtypes is therefore the most important requirement to increase the understanding of various mGluRs' roles in physiological and pathophysiological processes in the mammalian CNS. High-throughput screening of chemical libraries using cells stably transfected with individual, cloned mGluRs may offer a promising approach to identify new lead compounds which are active on the individual receptor subtypes (Knopfel et al., J. Med. Chem.

38:1417, 1995). These lead compounds could serve as templates for extensive chemical modification studies to further improve potency, mGluR subtype selectivity, and important therapeutic characteristics such as bioavailability.

With this information in mind, it is evident that the novel mGluR has a unique pattern of expression in the mammalian CNS compared to other mGluR subtypes. The novel mGluR is expected to exhibit a unique pharmacological profile for various agonists, antagonists and modulatory molecules compared to other mGluR subtypes. As a result of these factors, compounds acting potently and specifically on the novel mGluR that is the subject of the present invention will have actions on the mammalian CNS that are distinct from compounds acting on other mGluR subtypes. Therefore, it is likely that compounds selective for the novel mGluR of the present invention will have unique uses and advantages with regard to the treatment of various CNS pathophysiologies and disease states.

The preferred use of the receptor and methods of the present invention is to screen for compounds which modulate the activity of the novel metabotropic glutamate receptor, and to use such compounds to aid in the treatment of neurological diseases or disorders. However, other uses are also contemplated, including diagnosis and treatment. Such uses are based on the novel metabotropic glutamate receptor identified herein, the sequence of which is provided in SEQ ID NO. 1, and the DNA coding sequence is provided in SEQ ID NO. 5 (representing the open reading frame (ORF) in SEQ ID NO. 2, nucleotides 1-2724).

Thus, in a first aspect, the invention provides a purified or isolated nucleic acid molecule at least 15 nucleotides in length. This nucleic acid codes for at least five contiguous amino acid residues of a unique portion of a metabotropic glutamate receptor protein which has the amino acid sequence provided in SEQ ID NO: 1, a metabotropic glutamate receptor protein which is a contiguous portion of SEQ ID NO: 1 or a functionall equivalent of such amino acid sequences. Preferably, the metabotropic glutamate receptor protein is a human protein. In particular embodiments the nucleic acid molecule comprises a genomic DNA sequence, a cDNA sequence, or an RNA sequence. Since two novel metabotropic glutamate receptor proteins are demonstrated which differ only in the presence or absence of a terminal sequence, in preferred embodiments the glutamate receptor protein comprises SEQ ID NO: 1, or residues 1 to 893 of SEQ ID NO: 1, or a functional equivalent of those sequences. Of particular interest are nucleic acid molecules encoding essentially a full size novel metabotropic glutamate receptor protein. Therefore, in preferred embodiments the nucleic acid molecule encodes the amino acid sequence of SEQ ID NO: 1, or of amino acid residues of 1-893 of SEQ ID NO: 1, or of a functional equivalent of those sequences.

It is recognized that a large yet finite number of different nucleic acid sequences will code for the same amino acid sequence due to the redundancy of the genetic code. Such alternative coding sequences are within the scope of the above aspect of the invention.

In a preferred embodiment, the nucleic acid molecule encoding sequence ID NO: 1 has the nucleic acid sequence of SEQ ID NO: 5. Also in preferred embodiments, the nucleic acid molecule comprises at least 15 or 50 contiguous nucleotides of the nucleic acid sequence SEQ ID NO: 5 or of a sequence substantially complementary thereto. In particular embodiments, the nucleic acid molecule comprises at least 3 or at least 15 contiguous nucleotides of the nucleic acid sequence provided in nucleotides 2678 to 2724 of SEQ ID NO: 5. Likewise, in a preferred embodiment, the nucleic acid molecule encodes at least 5 contiguous amino acid residues, of which at least one is one of the residues 894 to 908 of SEQ ID NO: 1 and preferably all of the amino acid residues 894 to 908.

Since the use of a modified metabotropic glutamate receptor protein is advantageous in certain applications, in a preferred embodiment, the invention also provides an isolated or purified nucleic acid molecule encoding an amino acid sequence which comprises an extracellular domain which is part of the amino acid sequence of SEQ ID NO: 1. In this embodiment the encoded amino acid sequence is substantially free of membrane spanning domain and intracellular domain portions contained in the amino acid sequence of SEQ ID NO: 1. Likewise, in other particular embodiments, the invention provides other isolated or purified nucleic acid molecules encoding one or more domains which are part of the amino acid sequence of SEQ ID NO. 1, but which do not include at least one such domain. Thus, the invention provides nucleic acid molecules which encode an intracellular domain that is free of transmembrane and extracellular domains, or a transmembrane domain that is free of intracellular and extracellular domains, or an extracellular domain of a metabotropic glutamate receptor that is substantially free of the membrane spanning domains of said metabotropic glutamate receptor, or extracellular and membrane spanning domains which are substantially free of the intracellular domain. Similarly, in particular embodiments, the nucleic acid encodes a metabotropic glutamate receptor that is substantially free of at least one membrane spanning domain portion or a metabotropic glutamate receptor that is substantially free of the extracellular domain of said metabotropic glutamate receptor, or a contiguous multiple-transmembrane domain including intervening intracellular and extracellular domains but substantially free of N-terminal extracellular and C-terminal intracellular domains of SEQ ID NO: 1 (e.g., a seven-transmembrane domain).

In further preferred embodiments the nucleic acid molecule encodes an extracellular domain of SEQ ID NO. 1, transcriptionally coupled to a second nucleic acid molecule which encodes transmembrane and intracellular domains of a protein which is not a metabotropic glutamate receptor protein (i.e., a non-metabotropic glutamate receptor); the purified nucleic acid encodes a fusion protein composed of an N-terminal extracellular domain contiguous with a seven-transmembrane domain of SEQ ID NO: 1 and is transcriptionally coupled to nucleic acid encoding a C-terminal intracellular domain of a non-metabotropic glutamate receptor; the purified nucleic acid encodes a fusion protein composed of an N-terminal extracellular domain contiguous with a seven-transmembrane domain of SEQ ID NO: 1 and is transcriptionally coupled to nucleic acids encoding multiple intracellular domains of a non-metabotropic glutamate receptor.

Since it is advantageous in certain applications to utilize the complementary or anticoding DNA strand, the invention also provides an isolated or purified nucleic acid molecule which has a sequence substantially complementary to the sequence of a nucleic acid molecule of the above aspect.

In the context of this invention, the term "purified" means that the specified nucleic acid molecule or polypeptide has been separated from other nucleic acid molecules or polypeptides, respectively, with which it is found in such a manner that it forms a substantial fraction of the total nucleic acids or polypeptides present in a preparation. Preferably, the specified molecule constitutes at least 1, 5, 10, 50, 75, 85, or 95 percent or more of the molecules of that type (nucleic acid or polypeptide) present in a preparation.

By "isolated" in reference to nucleic acid, polypeptides, or other biomolecules of this invention is meant the molecule is present in a form (i.e., its association with other molecules) other than found in nature. For example, isolated receptor nucleic acid is separated from one or more nucleic acids which are present on the same chromosome, and an isolated polypeptide is separated from a substantial fraction of the other polypeptides with which it is normally found in nature. Preferably, the isolated nucleic acid or polypeptide is separated from at least 90% of the other nucleic acids present on the same chromosome or polypeptides normally found in the same cell. An example of isolated nucleic acid is recombinant nucleic acid. In this application, the term isolated nucleic acid is distinct from clones existant in a library of clones. It refers to a particular clone having the designated material encoded therein, isolated from other such clones. It can be created by standard recombinant methods to exist within a test-tube or within a desired cell or organism. It is preferably the only nucleic acid cloned within a standard vector, and may or may not contain the naturally occurring control sequences associated with it. Thus, it contains nucleic acid isolated from its natural environment and known to have the sequence claimed to be present. It is preferably a homogenous preparation of nucleic acid separate from other cellular components and from other nucleic acids.

In referring to the nucleic acids and polypeptides of the present invention, the term "unique" refers to a difference in sequence between a nucleic acid molecule of the present invention and the corresponding sequence of other receptor proteins, including other metabotropic glutamate receptor proteins. Thus, the sequences differ by at least one, but preferably a plurality of nucleotides or amino acid residues.

By "substantially complementary" is meant that the purified nucleic acid can hybridize to the complementary sequence region in a specific nucleic acid under stringent hybridization conditions. Such nucleic acid sequences are particularly useful as hybridization detection probes to detect the presence of nucleic acid encoding a particular receptor. Under stringent hybridization conditions, only highly complementary nucleic acid sequences hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides. Preferably, the nucleic acid is substantially complementary to at least 15, 20, 27, or 45, contiguous nucleotides of the specific sequence (e.g., in SEQ ID NO: 2).

In the context of the novel receptor and fragments, the term "functional equivalent" refers to a polypeptide that has an activity that can be substituted for one or more activities of a particular receptor or receptor fragment. This is explained in greater detail in the Detailed Description below.

In reference to the different domains of a metabotropic glutamate receptor, the term "substantially free" refers to the absence of at least most of the particular domain, preferably such that essentially none of an activity of interest specific to that domain remains. Thus, a short portion(s) of the particular domain sequence may remain, but does not provide a substantial particular activity normally provided by the intact domain.

By "comprising" it is meant including, but not limited to, whatever follows the word "comprising". Thus use of the term indicates that the listed elements are required, but that other elements are optional and may or may not be present. By "consisting essentially of" is meant that the listed elements are required, but that other elements are optional and may or may not be present depending upon whether or not they affect the activity or action of the listed elements.

Isolated or purified polypeptides corresponding to the nucleic acid molecules of the above aspects are also provided by the present invention. Therefore, in another aspect the invention features a purified polypeptide having at least 6 contiguous amino acids of an amino acid sequence provided in SEQ ID NO: 1. In preferred embodiments, the purified polypeptide has at least 12, 18, or 54 contiguous amino acids of SEQ ID NO: 1. In further preferred embodiments, the purified polypeptide comprises at least one amino acid, contiguous to the other contiguous amino acids, of the sequence provided in residues 894 to 908 of SEQ ID NO: 1. In other preferred embodiments, the purified polypeptide comprises at least three, six, nine, 12, or 15 contiguous amino acids of the sequence provided in residues 894 to 908 of SEQ ID NO: 1. In another aspect, the purified polypeptide comprises the amino acid sequence provided in residues 1 to 893 of SEQ ID NO: 1. In a preferred embodiment, the polypeptide further comprises a fifteen amino acid sequence that is homologous to the fifteen amino acid sequence at the carboxyl tail of mouse mGluR8. Other preferred receptor fragments include those having only an extracellular portion, a transmembrane portion, an intracellular portion, and/or a multiple transmembrane portion (e.g., seven transmembrane portion). In a particularly preferred embodiment, the polypeptide comprises the amino acid sequence of SEQ ID NO. 1.

Expression of a recombinant nucleic acid encoding a metabotropic glutamate receptor or receptor fragment is a useful method of producing polypeptides such as those described above. Therefore, in another aspect, the invention provides recombinant nucleic acid encoding a metabotropic glutamate receptor or receptor fragment as described in the first aspect above (i. e., coding for a metabotropic glutamate receptor protein having the amino acid sequence SEQ ID NO: 1 or functional equivalents thereof (i.e., these having one or more of the activities associated with that protein but having a few (1–10) amino acid alterations at non-critical areas which do not affect such activities)), cloned in an expression vector. An expression vector contains the necessary elements for expressing a cloned nucleic acid sequence to produce a polypeptide. An "expression vector" contains a promoter region (which directs the initiation of RNA transcription) as well as the DNA sequences which, when transcribed into RNA, will signal synthesis initiation. "Expression vector" includes vectors which are capable of expressing DNA sequences contained therein, i.e., the coding sequences are operably linked to other sequences capable of effecting their expression. It is implied, although not always explicitly stated, that these expression vectors must be replicable in the host organisms, either as episomes or as an integral part of the chromosomal DNA. Clearly a lack of replicability would render them effectively inoperable. A useful, but not a necessary, element of an effective expression vector is a marker encoding sequence—i.e., a sequence encoding a protein which results in a phenotypic property (e.g. tetracycline resistance) of the cells containing the protein which permits those cells to be readily identified. In sum, "expression vector" is given a functional definition, and any DNA sequence which is capable of effecting expression of a specified contained DNA code is included in this term, as it is applied to the specified sequence. As, at present, such vectors are frequently in the form of plasmids, the terms "plasmid" and "expression vector" are often used interchangeably. However, the invention is intended to include such other forms of expression vectors, including viral vectors, which serve equivalent functions and which may, from time to time become known in the art.

In reference to receptor proteins, "biologically functional" and "functional receptor" indicate that the receptor molecule or portion has a normal biological activity characteristic of the normal receptor in its usual cellular environment, which is relevant in the process of interest. Such a process can be, for example, a binding assay, or a complex cellular response. Preferably, a functional receptor is capable of participating in the normal cellular response reactions. In reference to an expression vector, "biologically finctional" means that the expression vector can be transcribed and the transcription product translated in the cell or expression system of interest.

The terms "transformed" and "transfected" refer to the insertion of a foreign genetic material into a prokaroytic or eukaryotic cell. Such insertion is commonly performed using vectors, such as plasmid or viral vectors, but can also include other techniques known to those skilled in the art.

Recombinant nucleic acid may contain nucleic acid encoding for a metabotropic glutamate receptor, receptor fragment, or metabotropic glutamate receptor derivative, under the control of its genomic regulatory elements, or under the control of exogenous regulatory elements including an exogenous promoter. By "exogenous" is meant a promoter that is not normally coupled in vivo transcriptionally to the coding sequence for the metabotropic glutamate receptor.

The expression vector may be used in another aspect of the invention to transform or transfect a prokaryotic or a eukaryotic host cell. Thus, another aspect of the present invention features a recombinant cell or tissue. The recombinant cell or tissue is made up of a recombinant nucleic acid sequence of the first aspect above, and a cell able to express the nucleic acid. Recombinant cells have various uses including acting as biological factories to produce polypeptides encoded for by the recombinant nucleic acid, and for producing cells containing a functioning metabotropic glutamate receptor. Cells containing a functioning metabotropic glutamate receptor can be used, for example, to screen for mGluR agonists, antagonists, or allosteric modulators. In preferred embodiments, the cell or tissue containing the recombinant nucleic acid encoding a functioning metabotropic glutamate receptor is selected from the group consisting of: central nervous system cell, peripheral nervous system cell, pituitary cell, and hypothalamic cell; and the recombinant nucleic acid encodes at least 12, 18 or 54 contiguous amino acids of SEQ ID NO: 1. In a particular embodiment of the invention the host cell is an oocyte, for example a Xenopus oocyte. In other preferred embodiments, the cell is one of NIH-3T3, HeLa, NG115, CHO, HEK 293 and COS7.

Another aspect of the invention describes a process for the production of a polypeptide product involving growing prokaryotic or eukaryotic host cells transformed or transfected with an expression vector having a nucleic acid molecule which codes for a metabotropic glutamate receptor protein having the amino acid sequence SEQ ID NO: 1, or a portion of that sequence, or a functional equivalent, under suitable nutrient conditions. The host cells are grown in a manner allowing expression of the polypeptide product. In a preferred aspect of the invention the process further involves isolation of the polypeptide product. "Suitable nutrient conditions" are those which will allow a cell to carry on normal metabolic functions and/or grow. The conditions suitable for a particular cell line or strain will generally differ, but appropriate conditions for each such cell type are known to, or can be determined by methods known to those skilled in the art.

Another aspect of the present invention describes a method of creating a transgenic non-human mammal by introducing a nucleic acid consisting essentially of the sequence SEQ ID NO: 2 or a fragment of that sequence into the cell(s) of a nonhuman mammal.

In related aspects, the invention provides transgenic, nonhuman mammals containing a transgene encoding the novel metabotropic glutamate receptor or a gene affecting the expression of that receptor, and methods of creating a transgenic nonhuman mammal containing a transgene encoding the novel metabotropic glutamate receptor. Preferably, embodiments use a human metabotropic glutamate receptor. In preferred embodiments, the transgene encodes a metabotropic glutamate receptor; alters the expression of a metabotropic glutamate receptor; inactivates the expression of the metabotropic glutamate receptor; and up-regulates or down-regulates the expression of the metabotropic glutamate receptor.

The term "transgenic" refers to an animal (also applicable to plants) having a foreign gene incorporated into the chromosomes of the animal's cells. In many cases, the foreign gene is derived from a different species, but the gene may also be a derivative of a gene normally found in that animal, inserted into the chromosome. Since the transgene is incorporated into the chromosome, it will be replicated along with the rest of the chromosome.

Another aspect of the invention features a method of screening for a compound that binds to or modulates the activity of a metabotropic glutamate receptor having the sequence SEQ ID NO: 1. The method involves introducing the metabotropic glutamate receptor and a test compound into an acceptable medium and monitoring the binding or modulation by physically detectable means thereby identifying the compounds which interact with or modulate the activity of the metabotropic glutamate receptor. Such a compound is useful as a therapeutic molecule to modulate metabotropic glutamate receptor activity or as a diagnostic agent to diagnose patients suffering from a disease characterized by an abnormal metabotropic glutamate activity. In a preferred embodiment, the mGluR is a chimeric receptor having an extracellular domain contained in the amino acid sequence of SEQ ID NO: 1 and an intracellular domain of a different receptor. Such a chimeric receptor allows activation of a cellular pathway not normally activated by the novel mGluR described herein. Also, in a preferred embodiment the metabotropic glutamate receptor is expressed by a cell and the compound is screened by monitoring the effect of the compound on the cell, more preferably the cell is a eukaryotic cell. For example, the method can involve contacting a cell containing a recombinant nucleic acid encoding a metabotropic glutamate receptor with the agent and detecting a change in metabotropic glutamate receptor activity. In another preferred embodiment, the method involves a competition binding assay with a labeled known binding agent. Preferably, the method is used to identify a metabotropic glutamate receptor-modulating agent.

The term "physically detectable means" refers herein to the means for detecting the interaction between a modulator or binding compound and the novel metabotropic glutamate receptor molecule. Such means can include, for example, spectroscopic methods (e.g., fluorometric measurement of $Ca^{2+}$) electrophysiological assays, and biochemical assays (e.g., specific enzyme activity). In addition to a variety of other assays, such biochemical assay can include detection of the activation by a chimeric receptor of a cellular pathway not normally activated by the novel mGluR. Each technique detects a physical property or parameter.

A "chimeric receptor" is one which has an amino acid sequence which is a fusion or association of sequences from two or more different proteins, at least one of which is a receptor protein. Typically in this invention, a chimeric receptor has amino acid sequences constituting domains (such as extracellular, membrane spanning, and intracellular) from two or more different receptor proteins, one of which is the novel mGluR8 of this invention.

Identification of metabotropic glutamate receptor-modulating agents is facilitated by using a high-throughput screening system. High-throughput screening allows a large number of molecules to be tested. For example, a large number of molecules can be tested individually using rapid automated techniques or in combination with using a combinatorial library of molecules. Individual compounds able to modulate metabotropic glutamate receptor activity present in a combinatorial library can be obtained by purifying and retesting fractions of the combinatorial library. Thus, thousands to millions of molecules can be screened in a short period of time. Active molecules can be used as models to design additional molecules having equivalent or increased activity. Such molecules will generally have a molecular weight of 10,000, preferably less than 1,000. They may be chosen from three active at calcium receptors, as described by Nemeth, et al., PCT/US94/12117 (WO 75/11221) hereby incorporated by reference herein.

A further aspect of the present invention describes a method of modulating the activity of a metabotropic glutamate receptor having the amino acid sequence of SEQ ID NO. 1, or a portion, or a functional equivalent, and includes the step of contacting the receptor with a compound that modulates one or more activities of the metabotropic glutamate receptor, in general either activating or inhibiting activation of the receptor.

The metabotropic glutamate receptor is contacted with a sufficient amount of a compound to modulate a metabotropic glutamate receptor activity. Modulating metabotropic glutamate receptor activity causes an increase or decrease in a cellular response which occurs upon metabotropic glutamate receptor activation, as described in the Detailed Description below. Typically, the compound either mimics one or more effects of glutamate at the metabotropic glutamate receptor, or blocks one or more effects of glutamate at the metabotropic glutamate receptor (or potentially both). The method can be carried out in vitro or in vivo.

The term "mimics" means that the compound causes a similar effect to be exhibited as is exhibited in response to contacting the receptor with glutamate. "Blocks" means that the presence of the compound prevents one or more of the normal effects of contacting the receptor with glutamate.

In the contect of this invention, "in vitro" means that a process is not carried out within or by a living cell(s). However, the process may use cell membranes and other cell parts, or even complete but non-living cells. "In vivo" means that the process is carried out within or by a living cell(s), and thus includes processes carried out within or by complex organisms such as mammals.

Further aspects of the present invention feature methods of treating a patient suffering from a disease or condition which is related to or which can be affected by the novel mGluR of this invention and/or by modulation of the activity of this mGluR. In general, these methods involve altering or modulating one or more activities of the mGluR by administering a compound or composition to the patient. The methods involve administering to a patient suffering from the disease, condition, or disorder a therapeutically effective amount of a compound which modulates metabotropic glutamate receptor activity, inhibits expression of the receptor, or provides functional receptors. Such compounds can, for example, include small molecules as well as polymers such as nucleic acids. A variety of diseases or conditions may be treated, including a neurological disease or disorder such as one preferably selected from the group consisting of neurodegenerative diseases, glutamate excitotoxicity, global and focal ischemic and hemorrhagic stroke, head trauma, spinal cord injury, hypoxia-induced nerve cell damage, and epilepsy. In preferred embodiments the neurodegenerative disease is Alzheimer's disease, Parkinson's disease or Huntington's disease.

Thus, in one aspect, the method of treating involves administering to the patient a therapeutically effective amount of a compound which modulates the activity of a metabotropic glutamate receptor (i.e., a metabotropic glutamate receptor-modulating agent) having the sequence SEQ ID NO: 1. (Therefore the agent may also modulate the activity of functional equivalents). As indicated, in a preferred embodiment, the patient has a neurological disease or a disorder. Also in a preferred embodiment, the compound has an effect on a physiological or pathophysiological activity. By way of illustration and not limitation, these can include convulsions, neuroprotection, neuronal death, neuronal development, central control of cardiac activity, waking, control of movements and control of vestibo ocular reflex.

In a related aspect, the method of treating involves administering to the patient a therapeutically effective amount of a nucleic acid encoding a functioning metabotropic glutamate receptor of the sequence SEQ ID NO: 1 or a functional equivalent. The nucleic acid can be administered using standard techniques such as through the use of retroviral vectors and liposomes.

In another related aspect, the method of treating involves administering to a patient a therapeutically effective amount of a nucleic acid which inhibits expression of a metabotropic glutamate receptor, preferably a receptor consisting essentially of the sequence SEQ ID NO: 1. Nucleic acids able to inhibit expression of a metabotropic glutamate receptor include anti-sense oligonucleotides, ribozymes and nucleic acid able to combine through homologous recombination with an endogenous gene encoding the receptor. Target sites of inhibitory nucleic acid include promoters, other regulatory agents acting on promoters, mRNA, pre-processed mRNA, and genomic DNA. Administration can be carried out by providing a transgene encoding the agent or by any other suitable method depending upon the use to which the particular method is directed. Preferably, the disease or disorder to be treated by administration of a nucleic acid of the preceding aspects is characterized by one or more of the following: (1) an abnormal level of a messenger whose production or secretion is affected by metabotropic glutamate receptor activity; and (2) an abnormal level or activity of a messenger whose function is affected by metabotropic glutamate receptor activity.

A "patient" refers to a mammal in which modulation of an metabotropic glutamate receptor will have a beneficial effect. Patients in need of treatment involving modulation of metabotropic glutamate receptors can be identified using standard techniques known to those in the medical profession. Preferably, a patient is a human having a disease or disorder characterized by one or more of the following: (1) abnormal metabotropic glutamate receptor activity; (2) an abnormal level of a messenger whose production or secretion is affected by metabotropic glutamate receptor activity; and (3) an abnormal level or activity of a messenger whose function is affected by metabotropic glutamate receptor activity.

By "therapeutically effective amount" is meant an amount of an agent which relieves to some extent one or more symptoms of the disease or disorder in the patient; or returns to normal either partially or completely one or more physiological or biochemical parameters associated with or causative of the disease.

With respect to a metabotropic glutamate receptor, "functioning" or "functional" indicates that the receptor has at least some of the relevant biological activities which such a receptor has under normal biological conditions (normal receptor under normal cellular conditions), and preferably substantially all of such activities. These can include, for example, specific binding characteristics and specific enzymatic activity (among others).

Related aspects of the present invention describes agents (e.g., compounds and pharmaceutical compositions) able to bind to the metabotropic glutamate receptor having the amino acid sequence SEQ ID NO. 1, or a portion or functional equivalent thereof. Preferably, the agent can modulate metabotropic glutamate receptor activity.

One aspect of the present invention features a pharmaceutical composition made up of a metabotropic glutamate receptor-modulating agent and a physiologically acceptable carrier. Such agents can be used to treat patients by modulating metabotropic glutamate receptor activity.

A pharmaceutical agent or composition refers to an agent or composition in a form suitable for administration into a mammal, preferably a human. Considerations concerning forms suitable for administration are known in the art and include toxic effects, solubility, route of administration, and maintaining activity. For example, pharmacological agents or compositions injected into the blood stream should be soluble. Pharmaceutical compositions can also be formulated as pharmaceutically acceptable salts (e.g., acid addition salts) and complexes thereof. The preparation of such salts can facilitate the pharmacological use of an agent by altering its physical characteristics without preventing it from exerting a physiological effect.

Another aspect of the invention provides a metabotropic glutamate receptor binding agent able to bind to a polypeptide having the amino acid sequence of SEQ ID NO: 1. In a preferred embodiment, the binding agent binds preferentially to the specified polypeptide. This means that under conditions of limited agent and equal numbers of accessible polypeptides, a greater number (fraction) of the specified polypeptide will bind the agent than will other polypeptides. In a preferred embodiment the binding agent is a purified antibody which recognizes an epitope present on a polypeptide having an amino acid sequence of SEQ ID NO: 1. In a further preferred embodiment, the binding agent is an antibody that is coupled to a toxin. Binding agents coupled to a toxin can be used to deliver the toxin to a cell containing a particular receptor. For example, an antibody coupled to a toxin directed to a cancer cell characterized by an abnormal receptor can selectively kill the cancer cell.

Antibodies able to bind metabotropic glutamate receptors have various uses such as being used as therapeutic agents to modulate metabotropic glutamate receptor activity; as diagnostic tools for determining metabotropic glutamate receptor number and/or location and/or functional integrity to diagnose a glutamate-related disease; and as research tools for studying receptor synthesis, structure, and function. For example, antibodies targeted to the metabotropic glutamate receptor are useful to elucidate which portion of the receptor a particular molecule such as the natural ligand binds.

In another aspect, the invention features a method for diagnosing a disease or disorder in a patient characterized by an abnormal number of the novel metabotropic glutamate receptors, or an alteration of the novel metabotropic glutamate receptor. Such alterations can, for example, include sequence alterations, altered activity, and altered location. The method involves identifying the number and/or location and/or functional integrity of one or more metabotropic glutamate receptors, such as the receptor having the amino acid sequence SEQ ID NO. 1 or a portion of functional equivalent thereof. The number and/or location and/or functional integrity is compared with that observed in patients characterized as normal or diseased as an indication of the presence of the disease or disorder.

Diagnoses can be carried out using metabotropic glutamate receptor-binding agents. For example, metabotropic glutamate receptor-modulating agents binding to metabotropic glutamate receptors, and antibodies which bind to metabotropic glutamate receptors, can be used for diagnoses. Preferably, binding agents are labeled with a detectable moiety, such as a radioisotope, an enzyme (e.g., alkaline phosphatase), a fluorescent label, a heavy atom, or other such label known in the art, or with a tag which binds another molecule having a detectable moiety (e.g., biotin/avidin).

An altered receptor has a different structure than the receptor has in normal individuals and is associated with a disease or disorder involving a metabotropic glutamate receptor. Such alterations may affect receptor function, and can be detected by assaying for a structural difference between the altered and normal receptor. Binding agents which bind to an altered receptor, but not to a normal receptor, can be used to determine the presence of an altered receptor. Additionally, a binding agent which can bind to a normal receptor, but not to a particular altered receptor, can be used to determine the presence of the particular altered receptor.

Similarly, the number of receptors can be determined by using agents binding to the tested-for receptor. Such assays generally involve using a labeled binding agent and can be carried out using standard formats such as competitive, non-competitive, homogenous, and heterogenous assays.

In other preferred embodiments, the method is an immunoassay in which an antibody to a metabotropic glutamate receptor is used to identify the number and/or location and/or functional integrity of the metabotropic glutamate receptors; the presence of a cancer, e.g., an ectopic tumor of the central nervous system or peripheral nervous system, is tested for by measuring metabotropic glutamate receptor number or alteration.

Other features and advantages of the invention will be apparent from the following description of the preferred embodiments thereof, and from the claims.

BRIEF DESCRIPTION OF THE DRAWINGS

FIG. 1 (SEQ ID NO: 1) shows the complete amino acid sequence of the novel human mGluR8 protein using the standard one letter abbreviations for amino acids.

FIG. 2A–2E (SEQ ID NO: 2) shows the 5' to 3' nucleotide sequence of the coding strand of the CCX-1 cDNA which contains an open reading frame encoding the novel human mGluR8 protein (nucleotides 1 to 2724). The standard one letter abbreviations of G, A, T and C are used for the four deoxynucleotidetriphosphates.

FIG. 3 (SEQ ID NO: 3) shows the partial 5' to 3' nucleotide sequence of the coding strand of the PCR fragment FF6.175. This nucleotide sequence corresponds to nucleotides 2154 to 2319 in the CCX-1 nucleotide sequence.

FIG. 4 (SEQ ID NO: 4) shows the 5' to 3' nucleotide sequence of the coding strand of the PCR fragment X120.15. This nucleotide sequence corresponds to nucleotides 2163 to 2283 in the CCX-1 nucleotide sequence; and nucleotides 10 to 130 in the FF6.175 nucleotide sequence.

FIGS. 5A–5D (SEQ ID NO: 5) shows the 5' to 3' nucleotide sequence of the open reading frame in CCX-1 cDNA (SEQ ID NO: 2), nucleotides 1 to 2724. This sequence codes for the amino acid sequence (SEQ ID NO: 1).

FIG. 7 shows the results of the functional activation experiment described in Example 4.

DETAILED DESCRIPTION

Figure 6A:
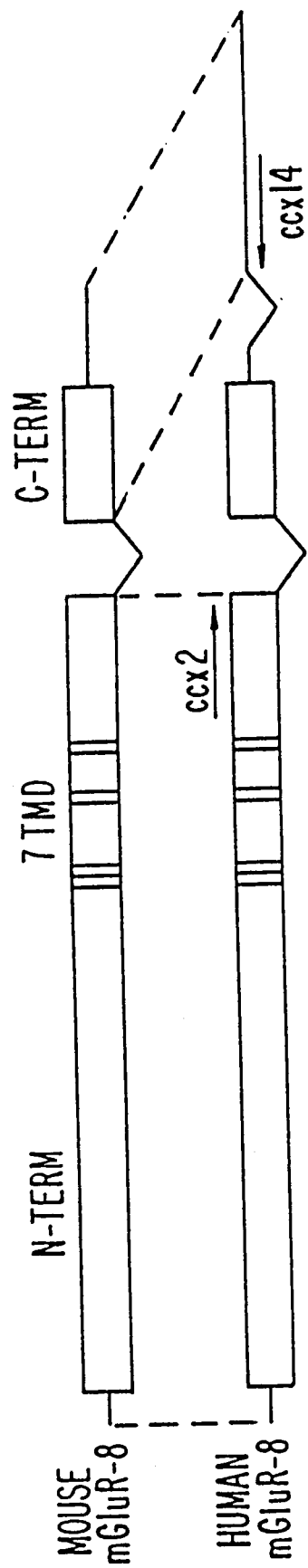
FIG. 6A depicts the PCR-primer design strategy for the splice-variant experiment described in Example 2. Graphical representations of the mouse mGluR-8 and human mGluR-8 sequences are compared for the design of primers that flank the putative splice variant region.

The cloning of eight metabotropic glutamate receptor subtypes from rat or mouse has been reported in the scientific literature. These include: rat mGluR1 (Masu et al., *Nature* 349:760, 1991; Houamed et al., *Science* 252:1318, 1991, Pin et al., *Proc. Natl. Acad. Sci.* 89:10331, 1992), rat mGluR2 (Tanabe et al., *Neuron* 8:169, 1992), rat mGluR3 (Tanabe et al., *Neuron* 8:169, 1992), rat mGluR4 (Tanabe et al., *Neuron* 8:169, 1992), rat mGluR5 (Abe et al., *J. Biol. Chem.* 267:13361, 1992), rat mGluR6 (Nakajima et al., *J. Biol. Chem.* 268:11868, 1993), rat mGluR7 (Okamoto et al., *J. Biol. Chem.* 269:1231, 1994; Saugstad et al., *Mol. Pharmacol.* 45:367, 1994) and mouse mGluR8 (Duvoisin et al., *J. Neuroscience* 15: 3075, 1995). The cloning of the human metabotropic glutamate receptor subtypes mGluR1 (Lin et al., *Soc. Neurosci. Abstr.* 20:468, 1994), mGluR2 (Flor et al., *Eur. J. Neurosci.*, in press, Knopfel et al., *J. Med. Chem.* 38:1417, 1995), mGluR4 (Flor et al., *Neuropharmacol.* 34:149, 1994), mGluR5 (Minakami et al., *Biochem. Biophys. Res. Commun.* 199:1136, 1994) and mGluR7 (Flor et al., *Soc. Neurosci. Abstr.* 20:468, 1994) have also been reported.

International Patent Application No. PCT/US91/09422, filed Dec. 12, 1991, provides G protein-coupled glutamate receptors isolated and cloned from rats. European Patent Application No. 93303520.6, filed May 6, 1993, provides a human metabotropic glutamate receptor and related DNA compounds described by the applicants as a human mGluR1. The subject of the present invention is a novel human metabotropic glutamate receptor. The novel receptor of the present invention is a human metabotropic glutamate receptor that is related to the Group III metabotropic glutamate receptors, which include mGluR4, mGluR6, mGluR7 and mGluR8.

Applicant is the first to demonstrate the novel human metabotropic glutamate receptor of the present invention, as well as the first to determine the nucleic acid sequence.

The following is a list of some of the terms used in the present disclosure. These terms are to be understood in light of the entire disclosure provided herein.

By "analgesic" is meant a compound capable of relieving pain by altering perception of nociceptive stimuli without producing anesthesia resulting in the loss of consciousness.

By "analgesic activity" is meant the ability to reduce pain in response to a stimulus that would normally be painful.

By "anticonvulsant activity" is meant efficacy in reducing convulsions such as those produced by simple partial seizures, complex partial seizures, status epilepticus, and trauma-induced seizures such as occur following head injury, including head surgery.

By "binding agent" is meant a molecule such as a small molecule, ligand, antibody, or toxin which binds to a receptor and may or may not modulate the activity of said receptor.

By "cognition-enhancement activity" is meant the ability to improve the acquisition of memory or the performance of a learned task. Also by "cognition-enhancement activity" is meant the ability to improve normal rational thought processes and reasoning.

By "cognition enhancer" is meant a compound capable of improving learning and memory.

By "efficacy" is meant that a statistically significant level of the desired activity is detectable with a chosen compound; by "significant" is meant a statistical significance at the $p<0.05$ level.

By "hyperalgesia" is meant an increased response to a stimulus that is normally painful.

By "minimal side effect" is meant that any side effect of the drug is tolerated by an average individual, and thus that the drug can be used for therapy of the target disease or disorders. Such side effects are well known in the art. Preferably, minimal side effects are those which would be regarded by the FDA as tolerable for drug approval for a target disease or disorder.

By "modulate" is meant to cause an increase or decrease in the activity of a cellular receptor.

By "muscle relaxant" is meant a compound that reduces muscular tension.

By "neuralgia" is meant pain in the distribution of a nerve or nerves.

By "neurological disorder or disease" is meant a disorder or disease of the nervous system. Examples of neurological disorders and diseases include global and focal ischemic and hemorrhagic stroke, head trauma, spinal cord injury, hypoxia-induced nerve cell damage as in cardiac arrest or neonatal distress, epilepsy, and neurodegenerative diseases.

By "neurodegenerative disease" is meant a neurological disease affecting cells of the central nervous system resulting in the progressive decrease in the ability of cells of the nervous system to function properly. Examples of neurodegenerative diseases include Alzheimer's disease, Huntington's disease, and Parkinson's disease.

By "neuroprotectant activity" is meant efficacy in prevention of neuronal cell death, such as that caused by neurological disorders or diseases.

By "potent" is meant that the compound has an $EC_{50}$ value (concentration which produces a half-maximal activation), or $IC_{50}$ (concentration which produces half-maximal inhibition), or $K_d$ (concentration which produces half-maximal binding) at a metabotropic glutamate receptor, with regard to one or more receptor activities, of less than 10

μM, more preferably less than 100 nM, and even more preferably less than 1 nM.

By "selective" is meant that the compound activates, inhibits activation and/or binds to a given metabotropic glutamate receptor subtype at a lower concentration than that at which the compound activates, inhibits activation and/or binds to an ionotropic glutamate receptor, or more preferably another metabotropic glutamate receptor subtype of a different classification group, or even more preferably another metabotropic glutamate receptor subtype of the same classification group. Preferably, the concentration difference is 10-fold, more preferably 50-fold, and even more preferably 100-fold.

By "therapeutically effective amount" is meant an amount of a compound which produces the desired therapeutic effect in a patient. For example, in reference to a disease or disorder, it is the amount which reduces to some extent one or more symptoms of the disease or disorder, and returns to normal, either partially or completely, physiological or biochemical parameters associated or causative of the disease or disorder. When used to therapeutically treat a patient it is an amount expected to be between 0.1 mg/kg to 100 mg/kg, preferably less than 50 mg/kg, more preferably less than 10 mg/kg, more preferably less than 1 mg/kg. Preferably, the amount provides an effective concentration at a metabotropic glutamate receptor of about 1 nM to 1 μM of the compound. The amount of compound depends on its $EC_{50}$ ($IC_{50}$ in the case of an antagonist) and on the age, size, and disease associated with the patient.

I. TECHNIQUES

A. Novel mGluR Nucleic Acid Sequence

The invention features nucleic acid sequences encoding metabotropic glutamate receptors and receptor fragments. The nucleic acid sequences may be engineered so as to allow for expression of the receptor sequences in prokaryotic or eukaryotic cells. For example, the entire coding sequence or a fragment thereof, may be combined with one or more of the following in an appropriate expression vector to allow for such expression: (1) an exogenous promoter sequence (2) a ribosome binding site (3) a polyadenylation signal (4) a secretion signal. Modification can be made in the 5'-untranslated sequences to improve expression in a prokaryotic or eukaryotic cell; or codons may be modified such that while they encode an identical amino acid, that codon may be a preferred codon in the chosen expression system. The use of such preferred codons is described in, for example, Grantham et al., *Nuc. Acids Res.*, 9:43–74 (1981), and Lathe, *J. Mol. Biol.*, 183:1–12 (1985) hereby incorporated by reference herein in their entirety. In a preferred embodiment of the current invention, the nucleic acid sequence is that of SEQ ID NO: 2, encoding a novel human metabotropic glutamate receptor. In a further preferred embodiment, the nucleic acid sequence is that of SEQ ID NO: 5.

In addition, a nucleic acid sequence encoding a particular receptor provides for additional tools to obtain other related receptors, for example by providing for nucleic acid hybridization assay probes. Furthermore, the nucleic acid sequences encoding two or more different but related receptors can be analyzed to determine localized regions of sequence conservation. These conserved nucleic acid regions are useful as hybridization probes; or alternatively provide for the design and synthesis of hybridization probes; which can be used to obtain cloned nucleic acids encoding other members of a receptor superfamily. Conserved sequences may be deduced from an analysis of the entire nucleic acid sequence of SEQ ID NO: 2 and comparison of that sequence with the nucleotide sequences encoding other mGluRs.

"Conserved nucleic acid regions" refers to regions within two or more nucleic acids encoding metabotropic glutamate receptors, to which a particular complementary nucleic acid can hybridize under lower stringency conditions. Examples of lower stringency conditions suitable for screening for nucleic acids encoding metabotropic glutamate receptors are provided in the examples below and in Abe et al. *J. Biol. Chem.*, 19:13361 (1992) (hereby incorporated by reference herein). Preferably, conserved nucleic acid regions differ by no more than 7 out of 20 nucleotides.

Uses of nucleic acids encoding cloned receptors or receptor fragments include one or more of the following: (1) producing receptor proteins which can be used, for example, for structure determination, to assay a molecule's activity on a receptor, and to obtain antibodies binding to the receptor; (2) being sequenced to determine a receptor's nucleotide sequence which can be used, for example, as a basis for comparison with other receptors to determine conserved regions, determine unique nucleotide sequences for normal and altered receptors, and to determine nucleotide sequences to be used as target sites for antisense nucleic acids, ribozymes, hybridization detection probes, or polymerase chain reaction (PCR) amplification primers; (3) as hybridization detection probes to detect the presence of a native receptor and/or a related receptor in a sample; and (4) as PCR primers to generate particular nucleic acid sequence regions, for example to generate regions to be probed by hybridization detection probes.

In general, the nucleic acid molecules of this invention have nucleic acid sequences encoding full length metabotropic glutamate receptors, metabotropic glutamate receptor fragments, derivatives of full length metabotropic glutamate receptors, and derivatives of metabotropic glutamate receptor fragments useful in the present invention. These include nucleic acid sequences comprising the sequences provided in SEQ ID NO: 2, SEQ ID NO: 5, or nucleic acid sequences which encode the protein sequence provided in SEQ ID NO: 1, or their complementary strands; nucleic acid sequences which hybridize under stringent conditions to the nucleic acid sequences SEQ ID NO: 2 or SEQ ID NO: 5, or to fragments thereof; and nucleic acid sequences which, but for the degeneracy of the genetic code would hybridize to the nucleic acid sequences SEQ ID NO: 2 or SEQ ID NO: 5.

Preferably, the nucleic acid contains at least 15, 18, 27, and most preferably at least 45, contiguous nucleic acids of a sequence provided in SEQ ID NO: 2. Advantages of longer-length nucleic acid include producing longer-length protein fragments having the sequence of a metabotropic glutamate receptor which can be used, for example, to produce antibodies; increased nucleic acid probe specificity under higher stringency hybridization assay conditions; and more specificity for related metabotropic glutamate receptor nucleic acid under lower stringency hybridization assay conditions.

As described in the Summary above, the present invention also features a purified nucleic acid comprising a nucleic acid sequence region of at least 15, 25, 35 or preferably 55 contiguous nucleotides, substantially complementary to a sequence region in SEQ ID NO: 5. In preferred embodiments, included in the nucleic acid sequence region are at least three, nine, 15 or more preferably at least 25 contiguous nucleotides of the nucleic acid sequence provided in nucleotides 2678 to 2724 of SEQ ID NO: 5.

Similarly the present invention features nucleic acid encoding a metabotropic glutamate receptor or fragment thereof comprising a nucleic acid sequence encoding at least five contiguous amino acids provided in SEQ ID NO: 1. Preferably, the nucleic acid encodes at least 12, 18, 30, or 54 contiguous amino acids of SEQ ID NO: 1. In certain embodiments, the nucleic acid encodes at least one contiguous, more preferably at least three, six, nine, 12, or 15 contiguous amino acids provided in residues 894 to 908 of SEQ ID NO: 1. In other embodiments the nucleic acid encodes an amino acid sequence comprising residues 1 to 893 of SEQ ID NO: 1, or the nucleic acid further encodes an amino acid sequence homologous to the 15 amino acid sequence at the carboxy tail of mouse mGluR8.

Further, the nucleic acid may be complementary to the nucleic acid sequence coding for either the extracellular binding domain, the transmembrane domain or the intracellular domain portions. The nucleic acid coding for such domains may be transcriptionally coupled to a second nucleic acid sequence from a non-metabotropic glutamate receptor protein. For example, nucleic acid sequence derived from the novel receptor disclosed herein coding for the extracellular domain can be transcriptionally coupled to a second nucleic acid encoding the transmembrane and intracellular coding domain of a non-metabotropic glutamate receptor, or an extracellular binding domain can be transcriptionally coupled to a second nucleic acid encoding the transmembrane and intracellular coding domain of a metabotropic glutamate receptor that is a member of a different class or subclass of mGluR than the receptor having the sequence SEQ ID NO. 1. Such nucleic acids coding for receptor fragments and chimeric receptors are described in, for example, pending application U.S. Ser. No. 60/001,526, hereby incorporated by reference herein in its entirety. Due to the degeneracy of the genetic code, different combinations of nucleotides can code for the same polypeptide. Thus, numerous metabotropic glutamate receptors and receptor fragments having the same amino acid sequences can be encoded for by different nucleic acid sequences.

1. Cloning Using Hybridization Probes and Primers

The presently preferred method for isolating mGluR nucleic acid is based upon hybridization screening. Region-specific primers or probes derived from nucleic acid encoding a metabotropic glutamate receptor such as the nucleic acid sequence SEQ ID NO: 2, or a nucleic acid encoding the amino acid sequence SEQ ID NO: 1, can be used to prime DNA synthesis and PCR amplification, as well as to identify bacterial colonies or phage plaques containing cloned DNA encoding a member of the mGluR family using known methods (e.g., Innis et al., *PCR Protocols,* Academic Press, San Diego, Calif. (1990); Sambrook et al., *Molecular Cloning,* Cold Spring Harbor Laboratory Press (1989)).

a. PCR Cloning

Primer hybridization specificity to target nucleic acid encoding a mGluR can be adjusted by varying the hybridization conditions. When carrying out hybridization at higher stringency conditions of 50–60° C., sequences which are greater than about 76% homologous to the primer will be amplified. When employing lower stringency conditions, by carrying out hybridization at 35–37° C., sequences which are greater than about 40–50% homologous to the primer will be amplified.

Analysis of metabotropic glutamate receptors indicates that they are G protein-coupled receptors having seven conserved, putative transmembrane domains. One particularly useful approach is to employ degenerate primers homologous to the conserved, putative transmembrane domains and to amplify DNA regions encoding these sequences using polymerase chain reaction (PCR). Thus, such oligonucleotide primers are mixed with genomic DNA or cDNA prepared from RNA isolated from the tissue of choice and PCR carried out. Some experimentation may be required to specifically amplify novel G protein-coupled receptor sequences from the tissue of choice since these are not necessarily identical to already known G protein-coupled receptors, but this is well understood by those of ordinary skill in the art (see, for example, Buck, L. and Axel, R. (1991) *Cell,* 6:175–187).

b. Hybridization Assay Probes

Hybridization assay probes can be designed based on sequence information obtained from cloned mGluRs and amino acid sequences encoding such receptors such as the novel mGluR that is the subject of this invention. Hybridization assay probes can be designed to detect the presence of a particular nucleic acid target sequence perfectly complementary to the probe and target sequences of lesser complementarity by varying the hybridization conditions and probe design.

DNA probes targeted to metabotropic glutamate receptors can be designed and used under different hybridization conditions to control the degree of specificity needed for hybridization to a target sequence. Factors affecting probe design, such as length, G and C content, possible self-complementarity, and wash conditions, are known in the art. (see, for example, Sambrook et al., *Molecular Cloning,* Cold Spring Harbor Laboratory Press (1989), hereby incorporated by reference herein. Sambrook et al., *Molecular Cloning,* also discusses the design and use of degenerate probes based on sequence polypeptide information.

As a general guideline, high stringency conditions (hybridization at 50–65° C., 5X SSPC, 50% formamide, wash at 50–65° C., 0.5X SSPC) can be used to obtain hybridization between nucleic acid sequences having regions which are greater than about 90% complementary. Low stringency conditions (hybridization at 35–37° C., 5X SSPC, 40–45% formamide, wash at 42° C. 2X SSPC) can be used so that sequences having regions which are greater than 35–45% complementary will hybridize to the probe.

Many tissues or cells can be used as a source for genomic DNA, including for example placenta or peripheral blood leukocytes. However, with respect to RNA, the most preferred source is a tissue or cell type which expresses elevated levels of the desired metabotropic glutamate receptor family member.

B. Novel Metabotropic Glutamate Receptor Nucleic Acid Derivatives

The isolated nucleic acid sequences of the invention also provide for the creation of modified nucleic acids with practical utility. The nucleic acid sequence can be mutated in vitro or in vivo, to, for example, (1) create variations in coding regions thereby generating metabotropic glutamate receptor variants or derivatives; (2) form new restriction endonuclease sites or destroy preexisting ones, to facilitate further in vitro modification or (3) form new splice sites to create mGluR splice variants. Standard recombinant techniques for mutagenesis such as in vitro site-directed mutagenesis (Hutchinson et al., *J. Biol. Chem.* 253:6551, (1978), Sambrook et al., Chapter 15, supra), use of TAB® linkers (Pharmacia), and PCR-directed mutagenesis can be used to create such mutations. Additionally, nucleic acid sequences of the current invention can be engineered and recombined with nucleic acids encoding other receptors to form nucleic acids encoding chimeric receptors. Such nucleic acids encoding chimeric receptors are described in, for example, pending application U.S. Ser. No. 60/001,526, hereby incorporated by reference herein in its entirety.

Preferred receptor fragments include those having functional receptor activity, a binding site, epitope for antibody recognition (typically at least six amino acids), and/or a site which binds a metabotropic glutamate receptor agonist or antagonist. Other preferred receptor fragments include those having only an extracellular portion, a transmembrane portion, an intracellular portion, and/or a multiple transmembrane portion (e.g., seven transmembrane portion). Such receptor fragments have various uses such as being used to obtain antibodies to a particular region and being used to form chimeric receptors with fragments of other receptors to create a new receptor having unique properties. Such purified receptor fragments and chimeric receptors are described in, for example, pending application U.S. Ser. No. 60/001,526, hereby incorporated by reference herein in its entirety. Thus, as described in the Summary above, the invention features derivatives of full-length metabotropic glutamate receptors and fragments thereof having the same, or substantially the same, activity as the full-length parent metabotropic glutamate receptor or fragment. Such derivatives include amino acid addition(s), substitution(s), and deletion(s) to the receptor which do not prevent the derivative receptor from carrying out one or more of the activities of the parent receptor. Functional equivalents of a metabotropic glutamate receptor protein include but are not limited to, such derivatives.

C. Antisense Oligonucleotides and Ribozymes

Antisense oligonucleotides and ribozymes can be targeted to a nucleic acid encoding a metabotropic glutamate receptor, and inhibit protein expression from the targeted nucleic acid. Numerous mechanisms have been proposed to explain the effects of antisense nucleic acids. For example, see Helene, C. and Toulme, J. *Biochimica et Biophysica Acta* 1049:99 (1990), and Uhlmann, E. and Peyman, A. *Chemical Review's* 90:543 (1990). Proposed mechanisms include hybridization of an antisense oligonucleotide to nascent mRNA causing premature transcription termination and interfering with mRNA processing by hybridizing to a pre-mRNA intron/exon junction. These and several other proposed mechanisms for inhibiting nucleic acid activity by an antisense oligonucleotide are based upon the ability of an antisense nucleic acid to hybridize to a target nucleic acid sequence. Preferably, anti-sense nucleic acids are 15 to 30 bases in length.

Ribozymes are enzymatic RNA molecules capable of catalyzing the specific cleavage of RNA. Ribozyme action involves sequence specific interaction of the ribozyme to complementary target RNA, followed by an endonucleolytic cleavage. Different ribozyme cutting motifs such as hammerhead can be engineered to specifically and efficiently catalyze endonucleolytic cleavage of specific RNA sequences encoding metabotropic glutamate receptors.

Specific ribozyme cleavage sites include GUA, GUU and GUC. Once cleavage sites are identified, short RNA sequences of between 15 and 20 ribonucleotides targeted to the region of the targeted RNA containing the cleavage site may be evaluated for predicted structural features to determine ribozyme suitability. The suitability of candidate targets may also be evaluated by testing their accessibility to hybridization with complementary oligonucleotides, using ribonuclease protection assays. See, Draper PCT WO 93/23569, hereby incorporated herein by reference.

Anti-sense oligonucleotides and ribozymes may be prepared by methods known in the art for the synthesis of RNA and DNA molecules. Standard techniques for chemically synthesizing nucleic acids include solid phase phosphoramidite chemical synthesis. Specific nucleic acids can also be produced enzymatically using a host transformed with a plasmid encoding for the desired nucleic acid.

Various modifications to the nucleic acid may be introduced to increase intracellular stability and half-life. Possible modifications include modifications to the phosphodiester backbone such as the use of phosphorothioate or methylphosphonate linkages.

In a preferred embodiment of the current invention, the antisense oligonucleotides and ribozymes are targeted to a nucleic acid coding for an amino acid sequence SEQ ID NO: 1. More preferred are antisense oligonucleotides and ribozymes targeted to a nucleic acid fragment of SEQ ID NO: 2.

D. Gene and Oligonucleotide Therapy

Gene and oligonucleotide therapy include the use of nucleic acid encoding a functioning metabotropic glutamate receptor, and the use of inhibitory oligonucleotides. Inhibitory oligonucleotides include antisense nucleic acids and ribozymes. Gene and oligonucleotide therapy can be performed ex vivo on cells which are then transplanted into a patient, or can be performed by direct administration of the nucleic acid or nucleic acid-protein complex into the patient.

Antisense oligonucleotides and ribozymes can be administered to a patient using different techniques such as by naked nucleic acid, nucleic acid compositions (for example, encapsulated by a liposome) and by retroviral vectors. Miller, *Nature* 357; 455–460, hereby incorporated by reference herein. Antisense oligonucleotides and ribozymes can also be introduced into a cell using nucleic acid encoding the antisense nucleic acid or ribozyme.

Gene therapy can be achieved by transferring a gene encoding a receptor, preferably a metabotropic glutamate receptor, into a patient in a manner allowing expression of the receptor protein. Recombinant nucleic acid molecules encoding receptor protein sequences can be introduced into a cell in vivo or ex vivo. In vivo transfection techniques include the use of liposomes and retroviral vectors. Miller, *Nature* 357; 455–460, hereby incorporated by reference herein. Ex vivo transfection increases the number of available transfection techniques, but also adds additional complications due to removal and subsequent insertion of cells into a patient.

In preferred embodiments of the current invention, the nucleic acid utilized for gene therapy is one coding for SEQ ID NO: 1, more preferably SEQ ID NO: 2, or a portion thereof; and/or the oligonucleotides utilized for oligonucleotide therapy are targeted to a nucleic acid coding for SEQ ID NO: 1, more preferably, SEQ ID NO: 2.

E. Transfected Cell Lines

Nucleic acid expressing a functional metabotropic glutamate receptor can be used to create transfected cell lines which functionally express a specific metabotropic glutamate receptor. Such cell lines have a variety of uses such as being used for high-throughput screening for molecules able to modulate metabotropic glutamate receptor activity; and being used to assay binding to a metabotropic glutamate receptor, and for production of metabotropic glutamate receptor peptides.

A variety of cell lines are capable of coupling exogenously expressed receptors to endogenous functional responses. A number of these cell lines (e.g. NIH-3T3, HeLa, NG115, CHO, HEK 293 and COS7) can be tested to confirm that they lack an endogenous metabotropic glutamate receptor. Those lines lacking a response to external glutamate can be used to establish stably transfected cell lines expressing the cloned metabotropic glutamate receptor.

Production of these stable transfectants is accomplished by transfection of an appropriate cell line with an eukaryotic expression vector, such as pCEP4, in which the coding sequence for the metabotropic glutamate receptor cDNA has been cloned into the multiple cloning site. These expression vectors contain a promoter region, such as the human cytomegalovirus promoter (CMV), that drive high-level transcription of cDNAs in a variety of mammalian cells. In addition, these vectors contain genes for the selection of cells that stably express the cDNA of interest. The selectable marker in the pCEP4 vector encodes an enzyme that confers resistance to hygromycin, a metabolic inhibitor that is added to the culture to kill the nontransfected cells. A variety of expression vectors and selection schemes are usually assessed to determine the optimal conditions for the production of metabotropic glutamate receptor-expressing cell lines for use in high-throughput screening assays.

The most effective method for transfection of eukaryotic cell lines with plasmid DNA varies with the given cell type. The metabotropic glutamate receptor expression construct will be introduced into cultured cells by the appropriate technique, either calcium phosphate precipitation, DEAE-dextran transfection, lipofection or electroporation.

Cells that have stably incorporated the transfected DNA will be identified by their resistance to selection media, as described above, and clonal cell lines will be produced by expansion of resistant colonies. The expression of the metabotropic glutamate receptor cDNA by these cell lines will be assessed by solution hybridization and Northern blot analysis. Functional expression of the receptor protein will be determined by measuring the inhibition of adenylate cyclase activity and the subsequent reduction in cAMP accumulation in response to externally applied metabotropic glutamate receptor agonists; or by measuring the mobilization of intracellular calcium in response to externally applied metabotropic glutamate receptor agonists.

In a preferred embodiment of the current invention, the nucleic acid used to create a stably transfected eukaryotic cell line codes for SEQ ID NO: 1, more preferably, the nucleic acid is that represented by SEQ ID NO: 2, and/or various modified derivatives thereof including: (1) derivatives encoding receptor mutants, (2) derivatives encoding chimeric receptors, or (3) derivatives encoding receptor fragments.

F. Transgenic Animals

Transgenic animals and transformed cells can be used to study the effects on cell function of receptor excess or depletion. Experimental model systems may be used to study the effects in cell or tissue cultures, in whole animals, or in particular cells or tissues within whole animals or tissue culture systems. The effects can be studied over specified time intervals (including during embryogenesis). Transgenic nonhuman mammals are particularly useful as an in vivo test system for studying the effects of introducing a metabotropic glutamate receptor; regulating the expression of a metabotropic glutamate receptor, i.e., through the introduction of additional genes, antisense nucleic acids, or ribozymes; and studying the effect of molecules which mimic or block the effect of glutamate on a metabotropic glutamate receptor.

The present invention provides for experimental model systems for studying the physiological role of a metabotropic glutamate receptor. Model systems can be created having varying degrees of receptor expression. For example, the nucleic acid encoding a receptor may be inserted into cells which naturally express the receptors such that the gene is expressed at much higher levels. Alternatively, a recombinant gene may be used to inactivate the endogenous gene by homologous recombination, and thereby create a metabotropic glutamate receptor deficient cell, tissue, or animal.

Inactivation of a gene can be caused, for example, by using a recombinant gene engineered to contain an insertional mutation (e.g., the neo gene). The recombinant gene is inserted into the genome of a recipient cell, tissue or animal, and inactivates transcription of the receptor. Such a construct may be introduced into a cell, such as an embryonic stem cell, by techniques such as transfection, transduction, and injection. Stem cells lacking an intact receptor sequence may generate transgenic animals deficient in the receptor.

Preferred test models are transgenic animals. A transgenic animal has cells containing DNA which has been artificially inserted into a cell and inserted into the genome of the animal which develops from that cell. Preferred transgenic animals are primates, mice, rats, cows, pigs, horses, goats, sheep, dogs and cats.

A variety of methods are available for producing transgenic animals. For example, DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438–4442 (1985)). By way of another example, embryos can be infected with viruses, especially retroviruses, modified to carry metabotropic glutamate receptor nucleotide sequences.

Pluripotent stem cells derived from the inner cell mass of the embryo and stabilized in culture can be manipulated in culture to incorporate nucleotide sequences of the invention. A transgenic animal can be produced from such stem cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), and Harlan Sprague Dawley (Indianapolis, Ind.). Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

Procedures for embryo manipulations are well known in the art. The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47:897–905 (1991). Other procedures for introduction of DNA into tissues of animals are described in U.S. Pat. No. 4,945,050 (Sandford et al., Jul. 30, 1990).

Transfection and isolation of desired clones can be carried out using standard techniques (e.g., E. J. Robertson, supra). For example, random gene integration can be carried out by co-transfecting the nucleic acid with a gene encoding antibiotic resistance. Alternatively, for example, the gene encoding antibiotic resistance is physically linked to a nucleic acid sequence encoding a metabotropic glutamate receptor.

DNA molecules introduced into ES cells can also be integrated into the chromosome through the process of homologous recombination. Capecchi, *Science* 244: 1288–1292 (1989). Methods for positive selection of the recombination event (e.g., neomycin resistance) and dual positive-negative selection (e.g., neomycin resistance and gangcyclovir resistance) and the subsequent identification of the desired clones by PCR have been described by Capecchi, supra and Joyner et al., *Nature* 338:153–156 (1989), the teachings of which are incorporated herein.

The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

An example describing the preparation of a transgenic mouse is as follows. Female mice are induced to superovulate and placed with males. The mated females are sacrificed by $CO_2$ asphyxiation or cervical dislocation and embryos are recovered from excised oviducts. Surrounding cumulus cells are removed. Pronuclear embryos are then washed and stored until the time of injection.

Randomly cycling adult female mice paired with vasectomized males serve as recipients for implanted embryos. Recipient females are mated at the same time as donor females and embryos are transferred surgically to recipient females.

The procedure for generating transgenic rats is similar to that of mice. See Hammer et al., *Cell* 63:1099–1112 (1990). Procedures for the production of transgenic non-rodent mammals and other animals are known in art. See, for example, Houdebine and Chourrout, supra; Pursel et al., *Science* 244:1281–1288 (1989); and Simms et al., *Bio/Technology* 6:179–183 (1988).

In a preferred embodiment of the current invention, the nucleic acid utilized for the production of transformed cells or non-human transgenic animals is that of SEQ ID NO: 2, or portions thereof.

G. Novel Metabotropic Glutamate Receptor Protein, Derivatives and Fragments

1. Metabotropic Glutamate Receptor Proteins

Recombinant metabotropic glutamate receptor proteins can be expressed in a variety of tissue and cell types including human tissue and cell types. These recombinant metabotropic glutamate receptor proteins can be utilized for a variety of purposes by those skilled in the art. The recombinant receptor proteins can be used as a source of antigen for the production of antibodies directed against metabotropic glutamate receptors, including polyclonal and monoclonal antibodies. In addition, recombinant metabotropic glutamate receptor proteins can be utilized for drug discovery purposes utilizing methods known to those skilled in the art. The recombinant receptor proteins can be utilized to screen (including high through-put screening) for molecules that bind to metabotropic glutamate receptors; as well as to screen for molecules that can modulate metabotropic glutamate receptor activity by acting as agonists, antagonists, or allosteric modulators. Finally, recombinant metabotropic glutamate receptor proteins can be used for structural studies of small molecule drug interactions with metabotropic glutamate receptors; antibody interactions with metabotropic glutamate receptors; or the interactions of other peptides and proteins with metabotropic glutamate receptors. These uses of metabotropic glutamate receptor proteins are not meant to be limiting.

In a preferred embodiment of the current invention the recombinant metabotropic receptor protein is an human metabotropic glutamate receptor protein, and more specifically it is a recombinant metabotropic glutamate receptor protein having the amino acid sequence represented in SEQ ID NO: 1 or a biologically active portion of that sequence, or a functional equivalent.

2. Metabotropic Glutamate Receptor Derivatives

Derivatives of a particular receptor are functional equivalents to that receptor, having similar amino acid sequence and retaining, to some extent, one or more activities of the related receptor. By "functional equivalent" is meant a protein that has an activity that can be substituted for one or more activities of a particular receptor or receptor fragment. Preferred functional equivalents retain all of the activities of a particular receptor or receptor fragment, however, the functional equivalent may have an activity that, when measured quantitatively, is stronger or weaker than the related receptor, as measured in standard receptor assays, for example, such as those disclosed herein. Preferred functional equivalents have activities that are within 1% to 10,000% of the activity of the related receptor, more preferably between 10% to 1000%, and more preferably within 50% to 500%. Functional equivalents may include, for example, derivatives which contain modifications or amino acid alterations in, for example, the region of a receptor which contains ligand binding activity. Such amino acid alterations may either increase or decrease the binding activity of the receptor with a particular binding agent. Functional equivalents may also include, for example, derivatives which contain modifications or amino acid alterations in the intracellular domain portion of the receptor which may, for example, increase or decrease the activity of the receptor by, for example, increasing or decreasing the cellular response to receptor activation. Derivatives have at least 15% sequence similarity, preferably 70%, more preferably 90%, even more preferably 95% sequence similarity to the related receptor. "Sequence similarity" refers to "homology" observed between amino acid sequences in two different polypeptides, irrespective of polypeptide origin.

The ability of the derivative to retain some activity can be measured using techniques described herein. Derivatives include modification occurring during or after translation, for example, by phosphorylation, glycosylation, crosslinking, acylation, proteolytic cleavage, linkage to an antibody molecule, membrane molecule or other ligand (see Ferguson et al., 1988, *Annu. Rev. Biochem.* 57:285–320).

Specific types of derivatives also include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Derivatives can contain different combinations of alterations including more than one alteration and different types of alterations.

While the effect of an amino acid change varies depending upon factors such as phosphorylation, glycosylation, intrachain linkages, tertiary structure, and the role of the amino acid in the active site or a possible allosteric site, it is generally preferred that the substituted amino acid is from the same group as the amino acid being replaced. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

While proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp).

Examples of modified amino acids include the following: altered neutral nonpolar amino acids such as amino acids of the formula $H_2N(CH_2)_nCOOH$ where n is 2–6, sarcosine (Sar), t-butylalanine (t-BuAla), t-butylglycine (t-BuGly), N-methyl isoleucine (N-MeIle), and norleucine (Nleu); altered neutral aromatic amino acids such as phenylglycine; altered polar, but neutral amino acids such as citrulline (Cit) and methionine sulfoxide (MSO); altered neutral and nonpolar amino acids such as cyclohexyl alanine (Cha); altered acidic amino acids such as cysteic acid (Cya); and altered basic amino acids such as ornithine (Om).

Preferred derivatives have one or more amino acid alteration(s) which do not significantly affect the receptor activity of the related receptor protein. In regions of the metabotropic glutamate receptor protein not necessary for receptor activity amino acids may be deleted, added or substituted with less risk of affecting activity. In regions required for receptor activity, amino acid alterations are less preferred as there is a greater risk of affecting receptor activity. Such alterations should be conservative alterations. For example, one or more amino acid residues within the sequence can be substituted by another amino acid of a similar polarity which acts as a functional equivalent.

Conserved regions tend to be more important for protein activity than non-conserved regions. Standard procedures can be used to determine the conserved and non-conserved regions important for receptor activity using in vitro mutagenesis techniques or deletion analyses and measuring receptor activity as described by the present disclosure.

Derivatives can be produced using standard chemical techniques and recombinant nucleic acid techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described in Section I.G.2. supra, and by Sambrook et al., *Molecular Cloning*, Cold Spring Harbor Laboratory Press (1989). For example, Chapter 15 of Sambrook describes procedures for site-directed mutagenesis of cloned DNA.

In a preferred embodiment of the current invention, the polypeptide subject to modification is that of a human metabotropic glutamate receptor, and more specifically, is a polypeptide having the amino acid sequence represented in SEQ ID NO: 1.

3. Metabotropic Glutamate Receptor Fragments

Receptor fragments are portions of metabotropic glutamate receptors. Receptor fragments preferably bind to one or more binding agents which bind to a full-length receptor. Binding agents include ligands, such as glutamate, quisqualate, agonists, antagonists, allosteric modulators, and antibodies which bind to the receptor. Fragments have different uses such as to select other molecules able to bind to a receptor.

Fragments can be generated using standard techniques such as expression of cloned partial sequences of receptor DNA and proteolytic cleavage of a receptor protein. Proteins are specifically cleaved by proteolytic enzymes, such as trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine.

Alternate sets of cleaved protein fragments are generated by preventing cleavage at a site which is susceptible to a proteolytic enzyme. For example, reaction of the E-amino group of lysine with ethyltrifluorothioacetate in mildly basic solution yields a blocked amino acid residue whose adjacent peptide bond is no longer susceptible to hydrolysis by trypsin. Goldberger et al., *Biochemistry* 1:401 (1962). Treatment of such a polypeptide with trypsin thus cleaves only at the arginyl residues.

Polypeptides also can be modified to create peptide linkages that are susceptible to proteolytic enzyme-catalyzed hydrolysis. For example, alkylation of cysteine residues with P-haloethylamines yields peptide linkages that are hydrolyzed by trypsin. Lindley, *Nature,* 178:647 (1956).

In addition, chemical reagents that cleave polypeptide chains at specific residues can be used. Witcop, *Adv. Protein Chem.* 16:221 (1961). For example, cyanogen bromide cleaves polypeptides at methionine residues. Gross & Witkip, *J. Am. Chem. Soc.* 83: 1510 (1961).

Thus, by treating a metabotropic glutamate receptor, or fragments thereof, with various combinations of modifiers, proteolytic enzymes and/or chemical reagents, numerous discrete overlapping peptides of varying sizes are generated. These peptide fragments can be isolated and purified from such digests by chromatographic methods. Alternatively, fragments can be synthesized using an appropriate solid-state synthetic procedure.

Fragments may be selected to have desirable biological activities. For example, a fragment may include just a ligand binding site. Such fragments are readily identified by those of ordinary skill in the art using routine methods to detect specific binding to the fragment. For example, in the case of a metabotropic glutamate receptor, nucleic acid encoding a receptor fragment can be expressed to produce the polypeptide fragment which is then contacted with a receptor ligand under appropriate association conditions to determine whether the ligand binds to the fragment. Such fragments are useful in screening assays for agonists and antagonists of glutamate.

Other useful fragments include those having only the external portion, membrane-spanning portion, or intracellular portion of the receptor. These portions are readily identified by comparison of the amino acid sequence of the receptor with those of known receptors, or by other standard methodology. These fragments are useful for forming chimeric receptors with fragments of other receptors to create a receptor with an intracellular portion which performs a desired function within that cell, and an extracellular portion which causes that cell to respond to the presence of glutamate, or those agonists or antagonists described herein. For example, chimeric receptors can be constructed such that the intracellular domain is coupled to a desired enzymatic process which can be readily detected by calorimetric, radiometric, luminometric, spectrophotometric or fluorimetric assays and is activated by interaction of the extracellular portion with its native ligand (e.g., glutamate) or agonist and/or antagonists of the invention. Cells expressing such chimeric receptors can be used to facilitate screening of metabotropic glutamate receptor agonists and antagonists.

In a preferred embodiment of the current invention, the polypeptide fragments are fragments of a human metabotropic glutamate receptor, and more specifically, are fragments of the polypeptide having the amino acid sequence represented in SEQ ID NO: 1.

H. Antibodies to Metabotropic Glutamate Receptors

Metabotropic glutamate receptors, derivatives, and fragments thereof retaining antigenic determinants can be used to generate antibodies recognizing a metabotropic glutamate receptor. Polyclonal antibodies recognizing a metabotropic glutamate receptor may be obtained by immunizing rabbits or other animals with isolated metabotropic glutamate receptor polypeptides. Polypeptides used for immunization can comprise the entire receptor polypeptide or fragments thereof.

Alternatively, monoclonal antibodies recognizing a metabotropic glutamate receptor may be obtained by immunizing appropriate mouse strains with isolated metabotropic glutamate receptor polypeptides. Again, polypeptides used for immunization can comprise the entire receptor polypeptide or fragments thereof, but whole cells expressing a metabotropic glutamate receptor polypeptide may also be used.

Metabotropic glutamate receptor polypeptides used for antibody production may be isolated from tissues or cells normally expressing the metabotropic glutamate receptor of choice, or from cells constructed for the purpose of recombinant expression of such polypeptides, or may be synthesized by conventional solid phase chemical methods. Polyclonal or monoclonal antibodies directed against these polypeptides can be produced using standard techniques known to those skilled in the art such as those described by Harlow and Lane in *Antibodies, a Laboratory Manual,* Cold Spring Harbor Laboratory, 1988. Polyclonal antibodies, for example, may be produced as described in Shigemoto et al., *Neuron* 12:1245–55 (1994), which describes polyclonal antibodies that recognize mGluR1, hereby incorporated by reference herein. Monoclonal antibodies that recognize mGluRs can be produced readily by one skilled in the art. The general methodology for making monoclonal antibodies by hybridomas is now well known to the art. See, e.g., M. Schreier et al., *Hybridoma Techniques* (Cold Spring Harbor Laboratory 1980); Hammerling et al., *Monoclonal Antibodies and T-Cell Hybridomas* (Elsevier Biomedical Press 1981); Kennett et al., *Monoclonal Antibodies* (Plenum Press 1980), hereby incorporated by reference herein. Immortal, antibody-secreting cell lines can also be produced by techniques other than fusion, such as direct transformation of B-lymphocytes with oncogenic DNA or EBV. Several antigen sources can be used, if desired, to challenge the normal B-lymphocyte population that is later converted to an immortal cell line.

In a preferred embodiment of the current invention, the polypeptides utilized for antibody production are from a human metabotropic glutamate receptor, and more specifically, are the polypeptide having the amino acid sequence represented in SEQ ID NO: 1, or fragments thereof.

I. mGluR Binding Agents Conjugated to Toxins

The invention further provides receptor-binding agents including antibodies and/or fragments thereof which can be conjugated to a toxin moiety, or expressed along with a toxin moiety as a recombinant fusion protein. The toxin moiety will bind to and enter a target cell using the interaction of the binding agent and the corresponding target cell surface receptor. The toxin moiety results in targeted cell death. Thus, cells having metabotropic glutamate receptors characteristic of a disease or disorder, such as cancers, can be targeted by the present invention.

Suitable toxin moieties bound to a binding agent include proteins such as pokeweed anti-viral protein, abrin, diphtheria exotoxin, or Pseudomonas exotoxin; ricin, and a high energy-emitting radio nuclide such as cobalt-60. Other examples of possible toxin moieties are known in the art. See, for example, "Conjugate Vaccines", *Contributions to Microbiology and Immunology,* J. M. Cruse and R. E. Lewis, Jr. (eds.), Carger Press, New York, (1989). The chosen toxin moiety should be pharmaceutically acceptable.

The conjugation of the binding agent to another moiety (e.g., bacterial toxin) can be accomplished by linking the two molecules using standard techniques so long as both molecules retain their respective activity. Possible linkages can be obtained by different chemical mechanisms, for example, covalent binding, affinity binding, intercalation, coordinate binding and complexation. Preferably, covalent binding is used. Covalent binding can be achieved either by direct condensation of existing side chains or by the incorporation of external bridging molecules.

Many bivalent or polyvalent linking agents are useful in coupling protein molecules, such as an antibody, to other molecules. Representative coupling agents include organic compounds such as thioesters, carbodiimides, succinimide esters, diisocyanates, glutaraldehydes, diazobenzenes and hexamethylene diamines. (See Killen and Lindstrom 1984, "Specific killing of lymphocytes that cause experimental autoimmune myasthenia gravis by toxin-acetylcholine receptor conjugates." *J. Immunol.* 133: 1335–2549; Jansen et al., 1982, "Immunotoxins: Hybrid molecules combining high specificity and potent cytotoxicity." *Immunological Rev.* 62: 185–216; and Vitetta et al., supra).

J. Compounds Targeted to the Novel Metabotropic Glutamate Receptor

The mGluR agonist and antagonist compounds described in the scientific literature are related to the endogenous agonist, glutamate (for reviews see: Cockcroft et al., *Neu-* rochem. Int. 23:583–594, 1993; Schoepp and Conn, Trends Pharmacol. Sci. 14:13–20, 1993; Hollmann and Heinemann, Annu. Rev. Neurosci. 17:31–108, 1994, Watkins and Collinridge, Trends Pharmacol. Sci. 15:333, 1994; Knopfel et al., J. Med. Chem. 38:1417, 1995). Such agonist and antagonist compounds have an acidic moiety, usually a carboxylic acid, but sometimes a phosphonic acid. Presumably then, such compounds bind mGluRs at the same site as the amino acid, glutamate. This has been confirmed for methylcarboxyphenylglycine, which was shown to be a competitive antagonist of glutamate (Eaton et al., Eur. J. Pharm.—Mol. Pharm. Sect. 244:195–197, 1993). Since these compounds are for the most part amino acids or amino acid derivatives, they have limited bioavailabilities which hampers in vivo studies assessing mGluR physiology, pharmacology and therapeutic potential. In addition, the currently available mGluR agonists and antagonists are of limited use, both as research tools and potential therapeutic agents, as a result of their lack of potency and selectivity. The identification of agonists and antagonists with a high degree of potency and selectivity for individual mGluR subtypes is therefore the most important requirement to increase the understanding of various mGluRs' roles in physiological and pathophysiological processes in the mammalian CNS.

The isolation of the nucleic acid encoding the novel mGluR of the present invention allows for the receptor's expression in transfected cell lines, and these cells can be utilized to screen for novel compounds capable of binding to and modulating the activity of the novel mGluR. These compounds could bind at the same site as glutamate, or alternatively at novel binding sites on the mGluR protein. Such screening can identify compounds with improved potency and selectivity for the novel mGluR. These compounds may also have other beneficial characteristics such as improved bioavailability. Such compounds would have utility as improved research tools for deducing the novel mGluR's physiological and pathophysiological roles, and as potential therapeutic agents.

Compounds targeted to the novel metabotropic glutamate receptor can have several uses including therapeutic uses and diagnostic uses. The syntheses of compounds that may bind to mGluRs and modulate their activity are described by Nemeth et al., entitled "Calcium Receptor Active Molecules" International Publication Number WO 93/04373, and in U.S. Ser. No. 08/485,038, filed Jun. 7, 1995, hereby incorporated by reference herein in their entirety, but potential mGluR active compounds are not limited to these compounds. Those compounds binding to a metabotropic glutamate receptor and those compounds efficacious in modulating metabotropic receptor glutamate activity can be identified using the procedures described herein. Those compounds which can selectively bind to the metabotropic glutamate receptor can be used therapeutically, or alternatively as diagnostics to determine the presence of the metabotropic glutamate receptor versus other glutamate receptors.

K. Modulation of Metabotropic Glutamate Receptor Activity

Modulation of metabotropic glutamate receptor activity can be used to produce different effects such as anticonvulsant effects, neuroprotectant effects, analgesic effects, cognition-enhancement effects, and muscle-relaxation effects. Each of these effects has therapeutic applications. Compounds used therapeutically should have minimal side effects at therapeutically effective doses.

Modulating metabotropic glutamate receptor activity causes an increase or decrease in a cellular response which occurs upon metabotropic glutamate receptor activation. Cellular responses to metabotropic glutamate receptor activation vary depending upon the type of metabotropic glutamate receptor activated. Generally, metabotropic glutamate receptor activation causes one or more of the following activities: (1) activation of phospholipase C, (2) increases in phosphoinositide (PI) hydrolysis, (3) intracellular calcium release, (4) activation of phospholipase D, (5) activation or inhibition of adenylyl cyclase, (6) increases or decreases in the formation of cyclic adenosine monophosphate (cAMP), (7) activation of guanylyl cyclase, (8) increases in the formation of cyclic guanosine monophosphate (cGMP), (9) activation of phospholipase $A_2$, (10) increases in arachidonic acid release, and (11) increases or decreases in the activity of ion channels, for example voltage- and ligand-gated ion channels. Inhibition of metabotropic glutamate receptor activation prevents one or more of these activities from occurring.

Activation of a particular metabotropic glutamate receptor refers to the production of one or more activities associated with the type of receptor activated, for example: (1) activation of phospholipase C, (2) increases in phosphoinositide (PI) hydrolysis, (3) intracellular calcium release, (4) activation of adenylyl cyclase, (5) increases in the formation of cyclic adenosine monophosphate (cAMP), (6) activation of phospholipase $A_2$, (7) increases in arachidonic acid release, (8) increases or decreases in ion channel activity.

The ability of a compound to modulate metabotropic glutamate activity can be monitored using electrophysiological and biochemical assays measuring one or more metabotropic glutamate activities. Examples of such assays include the electrophysiological assessment of metabotropic glutamate receptor function in Xenopus oocytes expressing cloned metabotropic glutamate receptors, the electrophysiological assessment of metabotropic glutamate receptor function in transfected cell lines (e.g., CHO cells, HEK 293 cells, etc.) expressing cloned metabotropic glutamate receptors, the biochemical assessment of PI hydrolysis and cAMP accumulation in transfected cell lines expressing cloned metabotropic glutamate receptors, the biochemical assessment of PI hydrolysis and cAMP accumulation in rat brain (e.g., hippocampal, cortical, striatal, etc.) slices, fluorimetric measurements of cytosolic $Ca^{2+}$ in cultured rat cerebellar granule cells, and fluorimetric measurements of cytosolic $Ca^{2+}$ in transfected cell lines expressing cloned metabotropic glutamate receptors.

Prior to therapeutic use in a human, the compounds are preferably tested in vivo using animal models. Animal studies to evaluate a compound's effectiveness to treat different diseases or disorders, or exert an effect such as an analgesic effect, a cognition-enhancement effect, or a muscle-relaxation effect, can be carried out using standard techniques.

L. Treatment of Neurological Diseases and Disorders and Other Conditions

Diseases or disorders which can be treated by modulating metabotropic glutamate receptor activity include one or more of the following types: (1) those characterized by abnormal metabotropic glutamate receptor activity; (2) those characterized by an abnormal amount of an extracellular or intracellular messenger whose production can be affected by metabotropic glutamate receptor activity; (3) those characterized by an abnormal effect (e.g., a different effect in kind or magnitude) of an intracellular or extracellular messenger which can itself be ameliorated by metabotropic glutamate receptor activity; and (4) other diseases or disorders in which modulation of metabotropic glutamate receptor activity will exert a beneficial effect, for example, in diseases or disorders where the production of an intracellular or extracellular messenger stimulated by receptor activity compensates for an abnormal amount of a different messenger. Examples of extracellular messengers whose secretion and/or effect can be affected by modulating metabotropic glutamate receptor activity include inorganic ions, hormones, neurotransmitters, growth factors, and chemokines. Examples of intracellular messengers include intracellular calcium, cAMP, cGMP, $IP_3$, and diacylglycerol.

The compounds and methods can also be used to produce other effects such as an analgesic effect, cognition-enhancement effect, and a muscle-relaxant effect.

A preferred use of the compounds and methods of the present invention is in the treatment of neurological diseases and disorders. Patients suffering from a neurological disease or disorder can be diagnosed by standard clinical methodology.

Neurological diseases or disorders include neurodegenerative diseases, glutamate excitotoxicity, global and focal ischemic and hemorrhagic stroke, head trauma, spinal cord injury, hypoxia-induced nerve cell damage, and epilepsy. These different diseases or disorders can be further medically characterized. For example, neurodegenerative diseases include Alzheimer's disease, Parkinson's disease and Huntington's disease.

Another preferred use of the present invention is in the production of other therapeutic effects, such as analgesic effects, cognition-enhancement effects, or muscle-relaxation effects. The present invention is preferably used to produce one or more of these effects in a patient in need of such treatment.

Patients in need of such treatment can be identified by standard medical techniques. For example, the production of analgesic activity can used to treat patients suffering from clinical conditions of acute and chronic pain including the following: preemptive preoperative analgesia; peripheral neuropathies such as occur with diabetes mellitus and multiple sclerosis; phantom limb pain; causalgia; neuralgias such as occur with herpes zoster; central pain such as that seen with spinal cord lesions; hyperalgesia; and allodynia.

M. In Vitro Diagnostics

The different molecules of the present invention can be used to facilitate diagnosis of metabotropic glutamate receptor-related diseases. Diagnosis can be carried out in vitro or in vivo. For example, the molecules of the present invention can be used to assay for defects in metabotropic glutamate receptors.

Nucleic acid probes can be used to identify defects in metabotropic glutamate receptors occurring at the genetic level. For example, hybridization probes complementary to nucleic acid encoding a receptor can be used to clone the receptor. The cloned receptor can be inserted into a cell, such as an oocyte, and its responsiveness to an mGluR ligand determined. Another example of using hybridization assay probes to detect defects involves using the probes to detect mRNA levels or the presence of nucleic acid sequences associated with a particular disease. A decreased MRNA level would be consistent with a decreased amount of expressed receptor.

Antibodies and fragments thereof able to recognize a metabotropic glutamate receptor antigen can be used to help determine receptor number, integrity, structure, and to localize cells expressing metabotropic glutamate receptors in the body. For example, antibodies targeted to metabotropic glutamate receptors can be used to determine the number of receptors on a cell; antibodies able to distinguish defective from normal receptors can be used to determine the presence of defective receptors; antibodies targeted to a metabotropic glutamate receptor can be used to determine if a disease or surgical procedure results in the spread of normal or abnormal cells expressing metabotropic glutamate receptors; and antibodies targeted to a metabotropic glutamate receptor can be used to localize cells having abnormal metabotropic glutamate receptor number or structure to direct subsequent treatment.

N. Formulation and Administration

The different molecules described by the present invention can be used to treat different diseases or disorders by modulating metabotropic glutamate receptor activity. The molecules of the invention can be formulated for a variety of modes of administration, including systemic and topical or localized administration. Techniques and formulations generally may be found in Remington's Pharmaceutical Sciences, Mack Publishing Co., Easton, Pa.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

Preferably, the therapeutically effective amount is provided as a pharmaceutical composition. A pharmacological agent or composition refers to an agent or composition in a form suitable for administration into a multicellular organism such as a human. Suitable forms, in part, depend upon the use or the route of entry, for example oral, transdermal, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms which prevent the agent or composition from exerting its effect.

The claimed compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. (See e.g., supra. PCT/US92/03736.) Pharmaceutically acceptable salts can be obtained from acids such as hydrochloric acid, sulfuric acid, phosphoric acid, sulfamic acid, acetic acid, citric acid, lactic acid tartaric acid, malonic acid, methanesulfonic acid, ethanesulfonic acid, benzene sulfonic acid, p-toluenesulfonic acid, cyclohexylsulfamic acid, and quinic acid.

Pharmaceutically acceptable salts can be prepared by standard techniques. For example, the free base form of a compound is dissolved in a suitable solvent, such as an aqueous or aqueous-alcohol solution, containing the appropriate acid and then isolated by evaporating the solution. In another example, a salt is prepared by reacting the free base and acid in an organic solvent.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and 15 intramuscular, orally, topically, or transmucosally.

The compounds of the invention can be formulated for a variety of modes of administration, including systemic and topical or localized administration. Techniques and formulations generally may be found in Remington's Pharmaceutical Sciences, 18th Edition, Mack Publishing Co., Easton, Pa., 1990.

For systemic administration, oral administration is preferred. For oral administration, the compounds are formulated into conventional oral dosage forms such as capsules, tablets and tonics.

Alternatively, injection may be used, e.g., intramuscular, intravenous, intraperitoneal, subcutaneous, intrathecal, or intracerebroventricular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. In addition, the compounds may be formulated in solid form and redissolved or suspended immediately prior to use. Lyophilized forms are also included.

Systemic administration can also be by transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be, for example, through nasal sprays or using suppositories. For oral administration, the molecules are formulated into conventional oral administration dosage forms such as capsules, tablets, and liquid preparations.

For topical administration, the compounds of the invention are formulated into ointments, salves, gels, or creams, as is generally known in the art.

As shown in the examples provided herein, the amounts of various compounds of this invention to be administered can be determined by standard procedures. Generally, a therapeutically effective amount is between about 1 nmole and 3 μmole of the molecule, preferably between about 0.1 nmole and 1 μmole depending on its $EC_{50}$ or $IC_{50}$ and on the age and size of the patient, and the disease or disorder associated with the patient. Generally, it is an amount between about 0.1 and 50 mg/kg, preferably 0.01 and 20 mg/kg of the animal to be treated.

The following examples illustrate the invention, but do not limit its scope.

II. EXAMPLES

Examples are provided below to illustrate different aspects and embodiments of the present invention. These examples are not intended in any way to limit the disclosed invention. Rather, they illustrate methodologies by which the novel mGluR of the present invention may be isolated, expressed in eukaryotic systems, and assessed for functional activity. They also illustrate methodologies by which compounds may be screened to identify those which bind to or modulate the activity of the novel mGluR.

Example 1

Cloning Inorganic Ion Receptors and Metabotropic Glutamate Receptors by Use of Degenerate Primer PCR Calcium receptors from bovine and human parathyroid gland; and from rat kidney and brain have been cloned (Brown et al., Nature 366:575, 1993; Garrett et al., J. Biol. Chem. 270:12919, 1995; Riccardi et al., Proc. Natl. Acad. Sci. USA 92:131, 1995, Ruat et al., Proc. Natl. Acad. Sci. USA 92: 3161, 1995). Analysis of the calcium receptor sequences (bovine, human and rat) by sequence database comparison indicated that while the calcium receptor sequences were unique, they exhibited weak, but significant homology (20–30% amino acid identity) with the metabotropic glutamate receptors (mGluRs). This result indicated that calcium receptors are structurally related to mGluRs and probably evolved from a common ancestral gene. Despite this structural relatedness, calcium receptors are pharmacologically distinct from mGluRs and in experiments with bovine parathyroid cells, or with Xenopus oocytes ectopically expressing calcium receptors, no responses to the mGluR agonists glutamate, trans-ACPD and quisqualate were observed.

The discovery of the calcium receptor sequences made it possible to determine regions of high sequence conservation between calcium receptors and mGluRs. Such regions were useful for guiding the preparation of hybridization and PCR probes which could be used to detect and isolate cDNA and genomic DNA sequences encoding additional members of this extended family of receptors.

Analysis of the amino acid sequences of calcium receptors and mGluRs indicated that sequence homology was highest in several limited regions including portions of the N-terminal putative extracellular domains, the putative seven-transmembrane domain regions, and the putative intracellular loops 1 and 3. Based on the homologies in transmembrane domains 2 and 5, and intracellular loop domains 1 and 3, four degenerate oligonucleotides were synthesized for use in PCR. These oligonucleotides contained XhoI or EcoRI restriction sites within their 5' ends to facilitate subcloning of the amplification products. These were:

TMb 2 SEQ I.D. NO. 6:
CCTGCTCGAGACIA(A,G)(C,T)CGGGA(A,G)CT(C,T)T(C,G)CTA(C,T) (C,A)T;
TM5 SEQ I.D. NO. 7:
CGGAATTCCGTTICGGG(A,T)(C,T)TTGAA(C,G)GC(A,G)(A,T)A(G,C);
CL1 SEQ I.D. NO. 8:
CCTGCTCGAGTCAAGGCTACG(A,G)(A,G)I(C,A)G(G,A,C,T)GA(G,A)(C,T)T; and

CL3 SEQ I.D. NO. 9:
CGGAATTCCATTTGGCTTCGTTGAAI(T,G)T(A,G,C,T)(G,T)C(G,A,T,C) GG.

Four different primer combinations were used in attempts to obtain novel ion receptor and metabotropic glutamate receptor clones: TM2+TM5, TM2+CL3, CL1 +TM5, and CL1 +CL3. PCR reactions were carried out using conditions previously described (Abe et al. *J. Biol. Chem.*, 19:13361, 1992) with annealing temperatures between 37° C. and 55° C. Each primer combination gave rise to products approximately 500 bp in size when used to amplify from cDNA or genomic DNA. Libraries of such PCR products were prepared by subcloning the products into a plasmid vector after amplification. Analysis of the products resulted in the detection of calcium receptor sequences, five mGluR sequences and additional sequences which are being characterized.

This example, like the other examples described herein, is not meant to be limiting. Various other highly conserved sequence regions can be identified and utilized in a similar fashion. Such advances are made possible by the discovery of calcium receptor sequences which allows for the identification of the most highly conserved sequences between calcium receptors and mGluRs, and the design of degenerate PCR primers based on these sequence homologies. Degenerate PCR can then be utilized to clone related DNA fragments. The cloned PCR products such as those described above can then be used as hybridization probes to isolate complete genomic clones and full-length cDNA clones. As additional members of this receptor family are discovered and their sequences determined, refinement of this approach will be possible. Thus, the invention herein enables the discovery of other members of this receptor family via an iterative process.

Example 2
Cloning of a Novel Human mGluR Sequence

PCR was carried out using human genomic DNA as template and the degenerate primers and reaction conditions indicated in the above example (Abe et al. *J. Biol. Chem.*, 19:13361, 1992). Amplification products were subjected to agarose gel electrophoresis and those corresponding to approximately 500 bp in size were subcloned following digestion with XhoI and EcoRI restriction endonucleases. DNA sequence analysis of the subclones via double-stranded DNA sequencing with Sequenase Version 2.0 (US Biochemical) identified sequences for the human calcium receptor and various human mGluR sequences. Most of the latter were readily identified as the human homologs of known rat mGluRs. However, one subclone was found among those generated from the CL1+CL3 amplification reaction which appeared to be unique. Partial sequence analysis of the clone FF6.175 (see SEQ ID NO: 3) indicated that it exhibited strong homologies to the rat mGluR4, mGluR6 and mGluR7 nucleotide sequences. Translation of the nucleotide sequence of FF6.175 revealed an amino acid sequence that was homologous to rat mGluRs 4, 6 and 7, but exhibiting unique amino acid differences. This suggested that FF6.175 did not encode the human homologue of mGluR4, mGluR6, or mGluR7; but instead, encoded a novel mGluR which is likely a member of this subfamily.

The subsequent publication of the mouse mGluR8 nucleic acid and amino acid sequences (Duvoisin et al., *J. Neuroscience* 15: 3075, 1995) confirmed this hypothesis. The partial nucleic acid sequence of FF6.175 (SEQ ID NO: 3) exhibited 92.2% sequence identity with the corresponding region of the mouse mGluR8 nucleic acid sequence. Furthermore, the amino acid sequence encoded by the FF6.175 partial nucleic acid sequence, exhibited 96.4% identity with the corresponding amino acid sequence of mouse mGluR8. These relationships implicated FF6.175 as a PCR fragment derived from the human genomic DNA which likely codes for a human mGluR8.

Specific PCR primers (FF6.175 RTS SEQ I.D. NO. 10: 5'-CTA CAT TGA CTA TGG AGA GCA GCG-3', FF6.175.RTS3SEQ. I.D. NO. 11: 5'-GAC CAT CAA GAG GAT ACT GTA TCC-3') based on the partial nucleic acid sequence of FF6.175 were synthesized commercially (Midland Certified Reagent Company). PCR was carried out using 100 ng of human genomic DNA (Clontech), 0.1 µM of each primer, 1X Perkin Elmer PCR Buffer, 0.2 mM dNTPs and 1.25 units of AmpliTaq enzyme in a reaction volume of 50 uls. A GeneAmp PCR System 9600 was employed to carry out 25 cycles of PCR: 94° C. for 15 seconds, 50° C. for 15 seconds, and 72° C. for 15 seconds, followed by a 10 minute extension at 72° C. The resulting 121 bp product was subcloned into pT7Blue (Novagen) and named pX120.15. The cloned PCR product was subjected to DNA sequence analysis via double-stranded DNA sequencing with Sequenase Version 2.0 (US Biochemical) and it was verified that X120.15 corresponded to a 121 bp subfragment (nucleotides 10 to 130) of the original FF6.175 PCR product. The sequence of this clone is given in SEQ ID NO: 4.

pX120.15 was linearized with EcoRI and used as template to synthesize an antisense $^{32}$P-labeled riboprobe with T7 RNA polymerase (Ambion). Human Multiple Tissue Northern blots (Clontech) were hybridized for 18 hours at 60° C. in 400 mM NaPO$_4$, pH 7.2, 1 mM EDTA, 5% SDS, 1 mg/ml BSA, 100 ug/ml sonicated salmon sperm DNA, 50% formamide and 1×10$^6$ cpm/ml riboprobe. Membranes were washed four times for 10 minutes each wash at room temperature with 2X SSC, 0.05% SDS, followed by two 30 minute washes at 65° C. with 0.1X SSC, 0.1% SDS. Membranes were then subjected to autoradiography.

The Northern blot analysis revealed that an approximate 3.8 Kb mRNA that hybridized to the X120.15 riboprobe under high stringency conditions was broadly expressed throughout the human brain (16 out of 16 regions examined), with the highest levels of expression in the subthalamic nucleus and cerebral cortex. In order to obtain a full length cDNA clone corresponding to this mRNA, a human cerebral cortex cDNA library in the phage vector lambdaDR2 (Cat.#HL1143X, Clontech) was screened using the X120.15 PCR product as probe. X120.15 was $^{32}$P-labeled by random priming using the Decaprime II kit according to the manufacturer's protocol (Ambion). Approximately 9×10$^5$ phage plaques were lifted in duplicate onto Hybond-N filters (Amersham). These filters were hybridized for 18 hours at 42° C. in 400 mM NaPO$_4$, pH 7.2, 1 mM EDTA, 5% SDS, 1 mg/ml BSA, 100 ug/ml sonicated salmon sperm DNA, 50% formamide and approximately 3×10$^5$ cpm/ml probe. Filters were washed twice at room temperature for 15 minutes each wash in 2X SSC, 1% SDS, then once for 30 minutes at 55° C. in 0.1X SSC, 1% SDS and autoradiographed. A single hybridizing clone (CCX-1) was isolated and rescued into the plasmid pDR2 by cre-loxP conversion. This clone was named pCCX-1 and subjected to DNA sequence analysis via double-stranded DNA sequencing with Sequenase Version 2.0 (US Biochemical).

The nucleotide sequence of the cDNA insert harbored in pCCX-1 is depicted in SEQ ID NO: 2. The CCX-1 CDNA is approximately 3850 bps long and contains 515 bps of 5'-untranslated sequence; an open reading frame of 2724 bps; and approximately 610 bps of 3'-untranslated sequence. The ambiguity concerning the length of the 3'-untranslated region is due to difficulty in establishing the exact number of nucleotides in the polyA tail. The 2724 bp open reading frame (nucleotides 1 to 2724, SEQ ID NO: 5) is 91.8% identical to the mouse mGluR8 nucleotide sequence (Duvoisin et al., *J. Neuroscience* 15: 3075, 1995) from nucleotides 1 to 2677. However, a 55 nucleotide insertion that is not present in the mouse mGluR8 cDNA begins at nucleotide 2678 of the CCX-1 cDNA and extends to nucleotide 2732. The nucleotide sequence from 2733 to 2779 of the CCX-1 cDNA then again exhibits strong homology (89.4% identity) with the 47 nucleotides preceding the TGA codon of the mouse mGluR8 cDNA.

The 2724 bp open reading frame of the CCX-1 cDNA encodes a 908 amino acid protein (SEQ ID NO: 1), of exactly the same size as the mouse mGluR8 protein. The amino acid sequence of the novel human mGluR is 97.5% identical to the mouse mGluR8 amino acid sequence (Duvoisin et al., *J. Neuroscience* 15: 3075, 1995) up to residue 893. Because of this sequence identity, the novel human mGluR is referred to herein as human mGluR8. However, as a result of the 55 nucleotide insertion which contains two in-frame stop codons (TAATAG) at nucleotides 2725 to 2730, the C-terminal 15 amino acids encoded by the CCX-1 cDNA diverge completely from the corresponding 15 amino acids at the C-terminus of the mouse mGluR8 protein.

The fact that nucleotides 2735 to 2779 in the 3'-untranslated region of the CCX-1 cDNA would encode 15 amino acids of which 14 are identical to the corresponding 15 amino acids at the C-terminus of the mouse mGluR8 protein strongly suggested that alternative splicing might produce a second human mGluR8 mRNA. This mRNA splice variant lacking the 55 nucleotide insertion would encode a human mGluR8 protein with a C-terminal amino acid sequence nearly identical to that of the mouse mGluR8 protein.

A PCR-based experiment was carried out to determine if the 55 nucleotide insertion in the CCX-1 cDNA might reflect alternative splicing to produce two human mGluR8 mRNAs encoding two different C-terminal amino acid sequences. Specific PCR primers (CCX.2 SEQ I.D. NO. 12: 5'-GAT GTA CAT CCA GAC AAC AAC AC-3', nucleotides 2430 to 2452 of CCX-1) and (CCX.14 SEQ I.D. NO. 13: 5'-CAG ATT GTG CCA TTT CCC TGT TTC-3', complementary to nucleotides 2781 to 2804 of CCX-1) were designed to flank the putative C-terminal splice junctions (synthesized commercially by Midland Certified Reagent company, Midland, Tex.) These primers were used to amplify from 10 ng each of human cerebral cortex, subthalamic nucleus and retina cDNA (Clontech, Palo Alto, Calif.) with the reaction conditions described above for X120.15 PCR product amplification. Amplification from approximately 20 ng of pCCX1 plasmid DNA was used as a positive control. The resulting PCR products were electrophoresed through a 2% agarose gel (Nusieve® GTG®, FMC, Rockland, Me.) and subsequently blotted onto a nylon membrane (Hybond-N, Amersham) by capillary transfer. The membrane was hybridized for 18 hours at 37° C. in 5 X SSC, 25 mM NaPO$_4$, pH 7.5, 5 X Denhardts, 5 mM EDTA, 0.1% pyrophosphate, 1% SDS, 30% formamide, 100 ug/ml salmon sperm DNA with a 24-mer oligonucleotide probe, (CCX.17 SEQ I.D. NO. 14: 5'-GGA AAT GAC AGA CCA AAT GGC GAG-3', nucleotides 2617 to 2640 of CCX-1). 100 ng of CCX.17 was $^{32}$P-labeled using T4 Polynucleotide Kinase (New England Biolabs, Beverly, Mass.), purified over a TE-10 column (Clontech) and the entire reaction used for hybridization. The membrane was washed four times at room temperature for 5 minutes each wash in 2 X SSC, 0.1% SDS and twice at 45° C. for 30 minutes each wash in 0.2 X SSC, 0.1% SDS. The membrane was subjected to autoradiography.

Figure 6B:
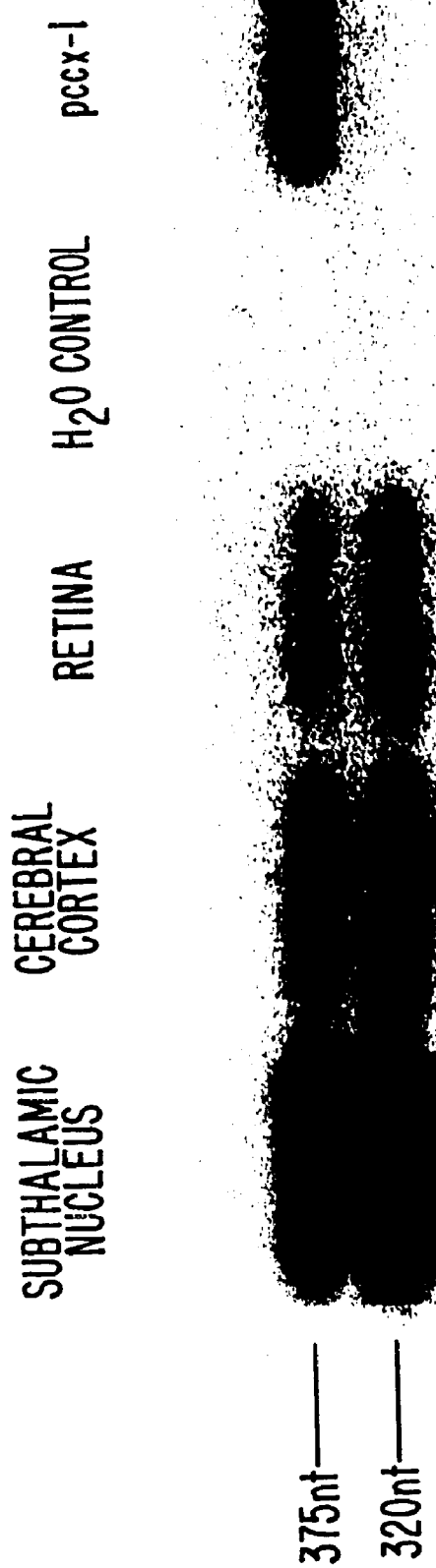
FIG. 6B shows the results of the splice-variant experiment described in Example 2.

The results of this experiment are shown in FIG. 6. A 375 nucleotide PCR product that hybridized with the labeled CCX.17 oligonucleotide was amplified from the subthalamic nucleus, cerebral cortex and retina cDNAs. This product was identical in size to that obtained when pCCX-1 plasmid DNA was used as template, indicating that a mRNA species that corresponds to the CCX-1 cDNA (hmGluR 375) is expressed in all three of these tissues. However, an additional PCR product of approximately 320 nucleotides that hybridized with the labeled CCX.17 oligonucleotide (hmGluR 320) was also amplified from the three tissues.

These results demonstrate that two different mGluR8 mRNA species arise from alternative splicing; and are both expressed in human retina and the two human brain regions that were examined. The results are consistent with the conclusion that the mRNA species that gives rise to the 320 nucleotide PCR product in FIG. 6, hmGluR 320, represents a human mGluR8 mRNA in which the 55 nucleotide segment has been eliminated during splicing. It is quite likely that elimination of this segment gives rise to an mRNA encoding a human mGluR8 protein in which 14 of 15 amino acids at the C-terminus are identical to the C-terminus of the mouse mGluR8 protein. In contrast, the second mRNA species that gives rise to the 375 nucleotide PCR product in FIG. 6, hmGluR 375 represents a human mGluR8 mRNA that corresponds to the CCX-1 cDNA. The 55 nucleotide segment is maintained in this mRNA during splicing and results in a second human mGluR8 receptor protein with a different 15 amino acid sequence at the C-terminus (SEQ ID NO: 1), which is completely divergent from the 15 amino acid sequence at the C-terminus of mouse mGluR8.

Example 3

Construction of pHmGR8b pCCX-1 DNA was digested with XhoI and XbaI to release a fragment extending from nucleotide 825 in the CCX-1 cDNA to the end of the poly A tail. This fragment (~2.5 Kb) was subcloned into the XhoI and XbaI sites of the mammalian expression vector, pcDNA I/Amp (Invitrogen) and the resulting clone named pHmGR8-3'. PCR primers (CCX.6b SEQ I.D. NO. 15: 5'-CAT GGG CCC TGA TGG AAG CTT CCA GAA GGT G-3', CCX.9 SEQ I.D. NO. 16: 5'-GAT GAA TCC CGA GCA ATT CGC TCC-3') were synthesized commercially (Midland Certified Reagent Company) and used to amplify a PCR product containing nucleotides –108 to 1184 of the novel human mGluR from approximately 20 ng of pCCX-1 under the PCR conditions described previously for X120.15 PCR product amplification. The resulting 1.3 Kb PCR product was digested with HindIII and EcoRI and subcloned into the corresponding sites of pHmGR8-3' to generate a full length novel human mGluR expression construct. The resulting expression plasmid (pHmGR8b) was subjected to DNA sequence analysis via double-stranded DNA sequencing with Sequenase Version 2.0 (US Biochemical) to verify that the subcloned HindIII-EcoRI fragment did not contain PCR-induced mutations.

Example 4

Functional Activation of the Novel Metabotropic Glutamate Receptor Expressed in Xenopus Oocvtes This example describes the activation of the novel mGluR using a Xenopus oocyte expression assay. pHmGR8b DNA was linearized by restriction enzyme digestion and capped sense-strand CRNA was synthesized by T7 RNA polymerase transcription. In vitro-transcribed RNA was concentrated by ethanol precipitation and the size and integrity of the RNA was assessed on denaturing agarose gels. cRNAs for the rat G-protein coupled inward rectifying potassium channel (GIRK) subunit (Kubo et al., Nature 364:802, 1993) and the rat cardiac inward rectifier (CIR) potassium channel subunit (Ashford et al., Nature 370:456, 1994; Krapvinsky et al., Nature 374: 135, 1995) were synthesized similarly.

Xenopus oocytes were isolated according to a standard protocol. Individual oocytes were injected with a mixture of cRNA containing 5 ng HmGR8b, 1.5 ng GIRK and 1.5 ng CIR; or a second control mixture containing 1.5 ng GIRK and 1.5 ng CIR alone. Following a 4 day incubation, oocytes were voltage clamped at a holding potential of −90 mV using standard two electrode voltage clamp techniques. Oocytes were perfused with a saline solution containing 25 mM KCl, 75 mM NaCl, 0.5 mM $CaCl_2$, 1 mM $MgCl_2$, 5 mM HEPES, pH 7.5. The presence of 25 mM KCl shifts the equilibrium potential of potassium ions ($E_K$) to a more positive potential (approximately −40 mV) and this allows detection of currents through GIRK/CIR at potentials negative to about −40 mV. Voltage ramps (1 sec duration) were used to determine the current amplitude at potentials ranging from −130 mV to +20 mV under control conditions and in the presence of L-glutamate.

In saline containing 25 mM KCl, a voltage ramp from −130 mV to +20 mV produced an inwardly rectifying current at potentials less than −40 mV (see FIG. 7, Control), for oocytes injected with the GIRK/CIR cRNA mixture or the HmGR8b/GIRK/CIR cRNA mixture. This inward current is typical in oocytes expressing GIRK/CIR and indicates the basal level of GIRK/CIR activation.

In oocytes injected with the HmGR8b/GIRK/CIR cRNA mixture, the inward current was further increased by application of 100–300 $\mu$M L-glutamate and net increases in current typically exceeded 1000 nA at a membrane potential of −130 mV (see FIG. 7, 300 $\mu$M L-glutamate). No changes in current amplitudes were observed above −40 mV. This effect of L-glutamate application was not observed with oocytes injected with only GIRK/CIR cRNA. These data indicate that coexpression of HmGR8b and GIRK/CIR cRNAs in Xenopus oocytes produces robust activation of the GIRK/CIR potassium channel complex via activation of a functional human mGluR8 receptor with L-glutamate.

Example 5
Construction of pCEP4-HmGR8b.

pHmGR8b plasmid DNA was digested with HindIII and the cleaved HindIII ends were blunt-ended with the Klenow fragment of DNA polymerase I (New England Biolabs) using standard conditions (Sambrook et al., *Molecular Cloning: A Laboratory Manual*, Cold Spring Harbor Laboratory Press, 1989). The DNA was then digested with XbaI and the 3.4 Kb fragment encoding human mGluR8 was isolated in low melting point agarose after electrophoretic separation from the pcDNA I Amp vector DNA. The 3.4 Kb fragment was then subcloned into the commercially available episomal mammalian expression vector pCEP4 (Invitrogen). To accomplish this, pCEP4 plasmid DNA was digested first with PvuII, and then subsequently with NheI. The 3.4 Kb blunt-end-XbaI fragment encoding human mGluR8 was then ligated into the PvuII and NheI sites of pCEP4. The resulting plasmid was named pCEP4-HmGR8b, and its integrity was validated by restriction enzyme mapping and double stranded DNA sequencing using Sequenase Version 2.0 (US Biochemical).

Example 6
Transfection and Stable Expression of the Novel mGluR in Mammalian

This example provides a method for the production of stably transfected mammalian cell lines expressing the novel human mGluR, but is not meant to be limiting. Human embryonic kidney cells (293, ATCC, CRL 1573) are grown in a routine manner. Cells are plated in 10 cm cell-culture plates in Dulbecco's modified Eagle's medium (D-MEM) containing 10% fetal bovine serum (FBS) and 1X penicillin-streptomycin (Life Technologies) so that they are approximately 70% confluent after an overnight incubation. To prepare DNA for transfection, the plasmid pCEP4-HmGR8b is precipitated with ethanol, rinsed and resuspended in sterile water at a concentration of 1 ug/ul. Fourteen micrograms of the plasmid DNA is incubated with the liposome formulation LipofectAMINE™ (Life Technologies) for 20 minutes in 1.7 mls of serum-free Opti-MEM (Life Technologies). After the room temperature incubation, 6.8 mls of Opti-MEM is added to the transfection mix. This solution is added to the cells which have been rinsed twice with 5 ml washes of Opti-MEM. The cells and transfection mix are incubated at 37° C. for 5 hours at which time 8.5 mls of Opti-MEM/20% FBS is added to bring the FBS concentration to 10%. After an overnight incubation the medium is changed back to D-MEM with 10% FBS, 1X penicillin-streptomycin, and 2 mM glutamine. After an additional 24 hour incubation, cells are detached with trypsin and replated in medium containing 200 ug/ml hygromycin (Boehringer Mannheim). Those cells which grow should contain pCEP4-HmGR8b which encodes the hygromycin resistance gene. Individual clonal cell lines are recovered and propagated using standard tissue culture techniques. Subcultures of both individual clonal cell lines and pools of many such cell lines can be prepared by dissociation into fresh tissue culture medium, and plating into fresh culture dishes with 1:10 splits of cells. Expression of the novel human mGluR mRNA of the present invention in clonal cell lines can be assessed by Northern blot analysis to identify cell lines exhibiting high levels of mRNA expression.

Example 7
Functional Activation of the Novel mGluR Expressed in Mammalian Cells

The novel human inGluR is likely a member of the Group III mGluR subfamily which includes rat and human mGluR4 (Tanabe et al., *Neuron* 8:169, 1992; Flor et al., *Neuropharmacol.* 34:149, 1994), rat mGluR6 (Nakajima et al., *J. Biol. Chem.* 268:11868, 1993), rat and human mGluR7 (Okamoto et al., *J. Biol. Chem.* 269:1231, 1994; Flor et al., *Soc. Neurosci. Abstr.* 20:468, 1994), and mouse mGluR8 (Duvoisin et al., *J. Neuroscience* 15: 3075, 1995). Like these other Group III mGluRs, the novel human mGluR is expected to encode a $G_i$-coupled receptor (inhibitorily coupled to adenylyl cyclase). Mammalian cell lines stably transfected with the pCEP4-HmGR8b expression construct can be utilized to examine glutamate-induced inhibition of adenylyl cyclase mediated by activation of human mGluR8. Adenylyl cyclase activity can be assessed by measuring cAMP accumulation after exposure of transfected cells to forskolin in the presence or absence of glutamate or other mGluR agonists as previously described (Tanabe et al., *Neuron* 8:169, 1992; Nakajima et al., *J. Biol. Chem.* 267:2437, 1992). In brief, clonal cells are seeded in 12-well plates at a density of 1.5×10$^5$ cells per well and grown for 3 days. After a 20 minute preincubation in phosphate-buffered saline (PBS) containing 1 mM 3-isobutyl-1-methylxanthine (IBMX) at 37° C., the cells are incubated with fresh PBS containing 10 μM forskolin, 1 mM IBMX, and test agents for 10 minutes. The medium is aspirated, and the reaction is stopped with ethanol. cAMP levels are measured by radioimmunoassay with a kit (Amersham). For pertussis toxin (PTX) treatment, cells are preincubated with varying concentrations of PTX for 11 hours at 37° C.

Example 8

Recombinant Receptor Binding Assays

The following is an example of a rapid screening assay to obtain compounds binding to the glutamate binding site of the novel human mGluR. The screening assay measures the binding of compounds to recombinant mGluRs expressed in stably transfected mammalian cells (O'Hara et al., *Neuron* 11:41, 1993). Cells stably transfected with the pCEP4-HmGR8b expression construct are grown to confluence, rinsed twice with PBS, and harvested by scraping in PBS. The harvested cells are pelleted by centrifugation at 1000 rpm for 5 minutes at 4° C., and frozen at −70° C. Cell membranes are prepared by homogenizing the pellet twice with 50 mM Tris-HCl (pH 7.4), 10 mM EDTA, 0.1 mM phenylmethylsulfonyl fluoride (PMSF), 0.1 mM D,L-benzylsuccinic acid, 10 ug/ml turkey egg white trypsin inhibitor; centrifugation at 30,000 x g for 10 minutes at 4° C.; then treatment with DNase and collection by centrifugation. Membrane suspensions are washed twice and resuspended in 50 mM Tris-HCl (pH 7.4), 2.5 mM CaCl$_2$ (Tris/Ca) and the total protein concentration is adjusted to 450–675 ug/ml. For binding assays 25 uls of 200 nM [$^3$H]glutamate (Dupont NEN) are added to 225 uls of membrane suspension in the presence or absence of cold competitor (10 mM glutamate) and incubated on ice for 1 hour. Assays are stopped by rapid addition of four mls of ice-cold Tris/Ca buffer and immediate collection of the membranes on Whatman GF/C filters by vacuum filtration. Ten mls of Optifluor (Packard) is added to filters in scintillation vials and the bound radioactivity is quantitated by scintillation counting.

The above example is not meant to be limiting. In a broader context, similar binding assays utilizing other radioligands binding to the glutamate binding site or other sites on the human mGluR can be developed by those skilled in the art. Such assays can be utilized to measure the binding of compounds to recombinantly expressed receptors, or receptor fragments. Compounds binding to the novel human mGluR may then be examined for their ability to modulate one or more functional activities of this mOluR.

Example 9

Molecule Screening Using Xenopus Oocytes

Oocytes injected with the HmGR8b/GIRK/CIR cRNA mixture described in Example 4 provide a system for assessing the actions of novel compounds on the novel human mGluR by measuring inward rectifying potassium channel activity. Compounds can be assessed for functional activation of human mGluR8 in the absence of glutamate or other known mGluR agonists (agonist activity); accentuation of human mGluR8 activation by glutamate or other known mGluR agonists (positive allosteric modulation); or blockade of human mGluR8 activation by glutamate or other known mGlUR agonists (antagonist activity).

Example 10

Molecule Screening Using Recombinant mGluRs Expressed in Stably Transfected Cell Lines Cell lines stably transfected with the novel human mGluR expression constructs as described in Example 6 can be utilized to assess the affinity of compounds on the novel human mGluR by utilizing binding assays as described in Example 8.

In addition, cell lines stably transfected with human mGluR8 expression constructs as described in Example 6 can be utilized to assess the actions of compounds on the novel human mGluR8 by measuring forskolin-stimulated cAMP production as described in Example 7. Functional activation of the human mGluR8 will inhibit forskolin-stimulated cAMP production in such cell lines.

Alternatively, cell lines co-expressing human mGluR8 in combination with rat GIRK and CIR potassium channel subunits can be utilized to assess the action of compounds on the novel mGluR8. As is the case in Xenopus oocytes (Example 4), functional activation of human mGluR8 should lead to activation of GIRK/CIR potassium channel activity in cell lines co-expressing human mGluR8, GIRK, and CIR.

Compounds can be assessed for functional activation of human mGluR8 in the absence of glutamate or other known mGluR agonists (agonist activity); accentuation of human mGluR8 activation by glutamate or other known mGluR agonists (positive allosteric modulation); or blockade of human mGluR8 activation by glutamate or other known mGluR agonists (antagonist activity).

Other embodiments are within the following claims.

We claim:

1. A purified polypeptide comprising at least 6 contiguous amino acids of the amino acid sequence from amino acid residues 893–908 of the amino acid sequence provided in SEQ ID NO: 1.

2. The purified polypeptide of claim 1, comprising at least 12 contiguous amino acids of said amino acid sequence.

3. The purified polypeptide of claim 1 further comprising at least two contiguous amino acid residues of the sequence provided in residues 1 to 892 of SEQ ID NO: 1.

4. The purified polypeptide of claim 3, comprising the amino acid sequence provided in residues 894 to 908 of SEQ ID NO: 1.

5. The purified polypeptide of claim 1, comprising an amino acid sequence comprising amino acid residues 893 to 908 of the amino acid sequence provided in SEQ ID NO: 1.

6. The purified polypeptide of claim 5 further comprising the amino acid residues of SEQ ID NO: 1 which comprise the intracellular domain of an mGluR8 receptor.

7. The purified polypeptide of claim 6 further comprising the amino acid residues of SEQ ID No: 1 which comprise at least one transmembrane domain of an mGluR8 receptor.

8. The purified polypeptide of claim 1 further comprising the amino acids of at least one intracellular domain of an mGluR8 receptor comprising the amino acid sequence of SEQ ID NO: 1.

9. The purified polypeptide of claim 8 further comprising the amino acids of at least one transmembrane domain of an mGluR8 receptor comprising the amino acid sequence of SEQ ID NO: 1.

10. A purified polypeptide comprising the amino acid sequence of SEQ ID NO: 1.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH:      908 amino acids
      (B) TYPE:        amino acid
      (C) STRANDEDNESS: single
      (D) TOPOLOGY:    linear (ii) MOLECULE TYPE:    Peptide (xi) SEQUENCE DESCRIPTION: SEQ ID NO: 1:

-continued

```
Met Val Cys Glu Gly Lys Arg Ser Ala Ser Cys Pro Cys Phe Phe Leu
 1               5                  10                  15

Leu Thr Ala Lys Phe Tyr Trp Ile Leu Thr Met Met Gln Arg Thr His
             20                  25                  30

Ser Gln Glu Tyr Ala His Ser Ile Arg Val Asp Gly Asp Ile Ile Leu
             35                  40                  45

Gly Gly Leu Phe Pro Val His Ala Lys Gly Glu Arg Gly Val Pro Cys
 50                      55                  60

Gly Glu Leu Lys Lys Glu Lys Gly Ile His Arg Leu Glu Ala Met Leu
 65                  70                  75                  80

Tyr Ala Ile Asp Gln Ile Asn Lys Asp Pro Asp Leu Leu Ser Asn Ile
             85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
            115                 120                 125

Ser Asp Val Lys Cys Ala Asn Gly Asp Pro Pro Ile Phe Thr Lys Pro
        130                 135                 140

Asp Lys Ile Ser Gly Val Ile Gly Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
        195                 200                 205

Ile Val Thr Ala Leu Gly Trp Asn Tyr Val Ser Thr Leu Ala Ser Glu
210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                245                 250                 255

Pro Arg Pro Gly Glu Phe Glu Lys Ile Ile Lys Arg Leu Leu Glu Thr
            260                 265                 270

Pro Asn Ala Arg Ala Val Ile Met Phe Ala Asn Glu Asp Asp Ile Arg
        275                 280                 285

Arg Ile Leu Glu Ala Ala Lys Lys Leu Asn Gln Ser Gly His Phe Leu
    290                 295                 300

Trp Ile Gly Ser Asp Ser Trp Gly Ser Lys Ile Ala Pro Val Tyr Gln
305                 310                 315                 320

Gln Glu Glu Ile Ala Glu Gly Ala Val Thr Ile Leu Pro Lys Arg Ala
                325                 330                 335

Ser Ile Asp Gly Phe Asp Arg Tyr Phe Arg Ser Arg Thr Leu Ala Asn
            340                 345                 350

Asn Arg Arg Asn Val Trp Phe Ala Glu Phe Trp Glu Glu Asn Phe Gly
        355                 360                 365

Cys Lys Leu Gly Ser His Gly Lys Arg Asn Ser His Ile Lys Lys Cys
    370                 375                 380

Thr Gly Leu Glu Arg Ile Ala Arg Asp Ser Ser Tyr Glu Gln Glu Gly
385                 390                 395                 400

Lys Val Gln Phe Val Ile Asp Ala Val Tyr Ser Met Ala Tyr Ala Leu
                405                 410                 415
```

-continued

```
His Asn Met His Lys Asp Leu Cys Pro Gly Tyr Ile Gly Leu Cys Pro
            420                 425                 430

Arg Met Ser Thr Ile Asp Gly Lys Glu Leu Leu Gly Tyr Ile Arg Ala
            435                 440                 445

Val Asn Phe Asn Gly Ser Ala Gly Thr Pro Val Thr Phe Asn Glu Asn
            450                 455                 460

Gly Asp Ala Pro Gly Arg Tyr Asp Ile Phe Gln Tyr Gln Ile Thr Asn
465                 470                 475                 480

Lys Ser Thr Glu Tyr Lys Val Ile Gly His Trp Thr Asn Gln Leu His
                    485                 490                 495

Leu Lys Val Glu Asp Met Gln Trp Ala His Arg Glu His Thr His Pro
            500                 505                 510

Ala Ser Val Cys Ser Leu Pro Cys Lys Pro Gly Glu Arg Lys Lys Thr
            515                 520                 525

Val Lys Gly Val Pro Cys Cys Trp His Cys Glu Arg Cys Glu Gly Tyr
            530                 535                 540

Asn Tyr Gln Val Asp Glu Leu Ser Cys Glu Leu Cys Pro Leu Asp Gln
545                 550                 555                 560

Arg Pro Asn Met Asn Arg Thr Gly Cys Gln Leu Ile Pro Ile Ile Lys
                565                 570                 575

Leu Glu Trp His Ser Pro Trp Ala Val Val Pro Val Phe Val Ala Ile
            580                 585                 590

Leu Gly Ile Ile Ala Thr Thr Phe Val Ile Val Thr Phe Val Arg Tyr
            595                 600                 605

Asn Asp Thr Pro Ile Val Arg Ala Ser Gly Arg Glu Leu Ser Tyr Val
610                 615                 620

Leu Leu Thr Gly Ile Phe Leu Cys Tyr Ser Ile Thr Phe Leu Met Ile
625                 630                 635                 640

Ala Ala Pro Asp Thr Ile Ile Cys Ser Phe Arg Arg Val Phe Leu Gly
                645                 650                 655

Leu Gly Met Cys Phe Ser Tyr Ala Ala Leu Leu Thr Lys Thr Asn Arg
            660                 665                 670

Ile His Arg Ile Phe Glu Gln Gly Lys Lys Ser Val Thr Ala Pro Lys
            675                 680                 685

Phe Ile Ser Pro Ala Ser Gln Leu Val Ile Thr Phe Ser Leu Ile Ser
            690                 695                 700

Val Gln Leu Leu Gly Val Phe Val Trp Phe Val Val Asp Pro Pro His
705                 710                 715                 720

Ile Ile Ile Asp Tyr Gly Glu Gln Arg Thr Leu Asp Pro Glu Lys Ala
                725                 730                 735

Arg Gly Val Leu Lys Cys Asp Ile Ser Asp Leu Ser Leu Ile Cys Ser
            740                 745                 750

Leu Gly Tyr Ser Ile Leu Leu Met Val Thr Cys Thr Val Tyr Ala Ile
            755                 760                 765

Lys Thr Arg Gly Val Pro Glu Thr Phe Asn Glu Ala Lys Pro Ile Gly
            770                 775                 780

Phe Thr Met Tyr Thr Thr Cys Ile Ile Trp Leu Ala Phe Ile Pro Ile
785                 790                 795                 800

Phe Phe Gly Thr Ala Gln Ser Ala Glu Lys Met Tyr Ile Gln Thr Thr
                805                 810                 815

Thr Leu Thr Val Ser Met Ser Leu Ser Ala Ser Val Ser Leu Gly Met
            820                 825                 830
```

```
Leu Tyr Met Pro Lys Val Tyr Ile Ile Phe His Pro Glu Gln Asn
        835                 840                 845

Val Gln Lys Arg Lys Arg Ser Phe Lys Ala Val Thr Ala Ala Thr
    850                 855                 860

Met Gln Ser Lys Leu Ile Gln Lys Gly Asn Asp Arg Pro Asn Gly Glu
865                 870                 875                 880

Val Lys Ser Glu Leu Cys Glu Ser Leu Glu Thr Asn Ser Lys Ser Ser
            885                 890                 895

Val Glu Phe Pro Met Val Lys Ser Gly Ser Thr Ser
            900                 905

(2) INFORMATION FOR SEQ ID NO: 2:

(i) SEQUENCE CHARACTERISTICS:
        (A) LENGTH:        3833 base pairs
        (B) TYPE:          nucleic acid
        (C) STRANDEDNESS:  single
        (D) TOPOLOGY:      linear (xi) SEQUENCE DESCRIPTION: SEQ ID NO: 2:
```

| | | | | | |
|---|---|---|---|---|---|
| GCGGCCGCCG | GTGGGAGTAT | TTGTTATTCA | CATGGAAGAG | ACTTGGCGCC | TGCTAGGCCA | 60 |
| GCTCAGCCCC | CTCAGCCCAG | AGATCAGCCA | CAAGTGCGGC | CGCTGTGCTC | GCCTCACGCG | 120 |
| GCGGCGGCGG | CGGCGGCGGC | GGCCGTGACA | TGGAGCTGCG | GGCCCCCGGC | GGGCTTCCTC | 180 |
| ACCGCGCCCT | CTGCGGGGAG | CAGGGAATAA | TTCTGCTACA | AGGCTGATTT | CAAGGACATG | 240 |
| AATTGTTGAC | CTCATCCCAA | CATCAGAACC | TCAGATGTTC | TAATTTTTGC | ACCATTCCAG | 300 |
| GCAAGTTGAT | CTTATAAGGA | AATAAAATTG | AACCTTAGGG | GTCTGATGGA | AATTCACTGT | 360 |
| GACATTCAAA | TCAAGAAAAC | TTGCTAATGC | CCACAGAGCC | TTTTCCCCAT | GGGCCCTGAT | 420 |
| GGTAGCCTCC | AGAAGGTGCA | GCCTCAGGTG | GTGCCCTTTC | TTCTGTGGCA | AGAATAAACT | 480 |
| TTGGGTCTTG | GATTGCAATA | CCACCTGTGG | AGAAAATGGT | ATGCGAGGGA | AAGCGATCAG | 540 |
| CCTCTTGCCC | TTGTTTCTTC | CTCTTGACCG | CCAAGTTCTA | CTGGATCCTC | ACAATGATGC | 600 |
| AAAGAACTCA | CAGCCAGGAG | TATGCCCATT | CCATACGGGT | GGATGGGGAC | ATTATTTTGG | 660 |
| GGGGTCTCTT | CCCTGTCCAC | GCAAAGGGAG | AGAGAGGGGT | GCCTTGTGGG | GAGCTGAAGA | 720 |
| AGGAAAAGGG | GATTCACAGA | CTGGAGGCCA | TGCTTTATGC | AATTGACCAG | ATTAACAAGG | 780 |
| ACCCTGATCT | CCTTTCCAAC | ATCACTCTGG | GTGTCCGCAT | CCTCGACACG | TGCTCTAGGG | 840 |
| ACACCTATGC | TTTGGAGCAG | TCTCTAACAT | TCGTGCAGGC | ATTAATAGAG | AAAGATGCTT | 900 |
| CGGATGTGAA | GTGTGCTAAT | GGAGATCCAC | CCATTTTCAC | CAAGCCCGAC | AAGATTTCTG | 960 |
| GCGTCATAGG | TGCTGCAGCA | AGCTCCGTGT | CCATCATGGT | TGCTAACATT | TTAAGACTTT | 1020 |
| TTAAGATACC | TCAAATCAGC | TATGCATCCA | CAGCCCCAGA | GCTAAGTGAT | AACACCAGGT | 1080 |
| ATGACTTTTT | CTCTCGAGTG | GTTCCGCCTG | ACTCCTACCA | AGCCCAAGCC | ATGGTGGACA | 1140 |
| TCGTGACAGC | ACTGGGATGG | AATTATGTTT | CGACACTGGC | TTCTGAGGGG | AACTATGGTG | 1200 |
| AGAGCGGTGT | GGAGGCCTTC | ACCCAGATCT | CGAGGGAGAT | TGGTGGTGTT | TGCATTGCTC | 1260 |
| AGTCACAGAA | AATCCCACGT | GAACCAAGAC | CTGGAGAATT | TGAAAAAATT | ATCAAACGCC | 1320 |
| TGCTAGAAAC | ACCTAATGCT | CGAGCAGTGA | TTATGTTTGC | CAATGAGGAT | GACATCAGGA | 1380 |
| GGATATTGGA | AGCAGCAAAA | AAACTAAACC | AAAGTGGGCA | TTTTCTCTGG | ATTGGCTCAG | 1440 |
| ATAGTTGGGG | ATCCAAAATA | GCACCTGTCT | ATCAGCAAGA | GGAGATTGCA | GAAGGGGCTG | 1500 |
| TGACAATTTT | GCCCAAACGA | GCATCAATTG | ATGGATTTGA | TCGATACTTT | AGAAGCCGAA | 1560 |
| CTCTTGCCAA | TAATCGAAGA | AATGTGTGGT | TTGCAGAATT | CTGGGAGGAG | AATTTTGGCT | 1620 |

-continued

```
GCAAGTTAGG ATCACATGGG AAAAGGAACA GTCATATAAA GAAATGCACA GGGCTGGAGC    1680

GAATTGCTCG GGATTCATCT TATGAACAGG AAGGAAAGGT CCAATTTGTA ATTGATGCTG    1740

TATATTCCAT GGCTTACGCC CTGCACAATA TGCACAAAGA TCTCTGCCCT GGATACATTG    1800

GCCTTTGTCC ACGAATGAGT ACCATTGATG GGAAAGAGCT ACTTGGTTAT ATTCGGCTG     1860

TAAATTTTAA TGGCAGTGCT GGCACTCCTG TCACTTTTAA TGAAAACGGA GATGCTCCTG    1920

GACGTTATGA TATCTTCCAG TATCAAATAA CCAACAAAAG CACAGAGTAC AAAGTCATCG    1980

GCCACTGGAC CAATCAGCTT CATCTAAAAG TGGAAGACAT GCAGTGGGCT CATAGAGAAC    2040

ATACTCACCC GGCGTCTGTC TGCAGCCTGC CGTGTAAGCC AGGGGAGAGG AAGAAAACGG    2100

TGAAAGGGGT CCCTTGCTGC TGGCACTGTG AACGCTGTGA AGGTTACAAC TACCAGGTGG    2160

ATGAGCTGTC CTGTGAACTT TGCCCTCTGG ATCAGAGACC CAACATGAAC CGCACAGGCT    2220

GCCAGCTTAT CCCCATCATC AAATTGGAGT GGCATTCTCC CTGGGCTGTG GTGCCTGTGT    2280

TTGTTGCAAT ATTGGGAATC ATCGCCACCA CCTTTGTGAT CGTGACCTTT GTCCGCTATA    2340

ATGCACACC TATCGTGAGG GCTTCAGGAC GCGAACTTAG TTACGTGCTC CTAACGGGA      2400

TTTTTCTCTG TTATTCAATC ACGTTTTTAA TGATTGCAGC ACCAGATACA ATCATATGCT    2460

CCTTCCGACG GGTCTTCCTA GGACTTGGCA TGTGTTTCAG CTATGCAGCC CTTCTGACCA    2520

AAACAAACCG TATCCACCGA ATATTTGAGC AGGGGAAGAA ATCTGTCACA GCGCCCAAGT    2580

TCATTAGTCC AGCATCTCAG CTGGTGATCA CCTTCAGCCT CATCTCCGTC CAGCTCCTTG    2640

GAGTGTTTGT CTGGTTTGTT GTGGATCCCC CCCACATCAT CATTGACTAT GGAGAGCAGC    2700

GGACACTAGA TCCAGAGAAG GCCAGGGGAG TGCTCAAGTG TGACATTTCT GATCTCTCAC    2760

TCATTTGTTC ACTTGGATAC AGTATCCTCT TGATGGTCAC TTGTACTGTT TATGCCATTA    2820

AAACGAGAGG TGTCCCAGAG ACTTTCAATG AAGCCAAACC TATTGGATTT ACCATGTATA    2880

CCACCTGCAT CATTTGGTTA GCTTTCATCC CCATCTTTTT TGGTACAGCC CAGTCAGCAG    2940

AAAAGATGTA CATCCAGACA ACAACACTTA CTGTCTCCAT GAGTTTAAGT GCTTCAGTAT    3000

CTCTGGGCAT GCTCTATATG CCCAAGGTTT ATATTATAAT TTTTCATCCA GAACAGAATG    3060

TTCAAAAACG CAAGAGGAGC TTCAAGGCTG TGGTGACAGC TGCCACCATG CAAAGCAAAC    3120

TGATCCAAAA AGGAAATGAC AGACCAAATG GCGAGGTGAA AAGTGAACTC TGTGAGAGTC    3180

TTGAAACCAA CAGTAAGTCA TCTGTAGAGT TTCCGATGGT CAAGAGCGGG AGCACTTCCT    3240

AATAGATCTT CCTCTACCAA GACAACATAT ATCAGTTACA GCAATCATTC AATCTGAAAC    3300

AGGGAAATGG CACAATCTGA AGAGACGTGG TATATGATCT TAAATGATGA ACATGAGACC    3360

GCAAAAATTC ACTCCTGGAG ATCTCCGTAG ACTACAATCA ATCAAATCAA TAGTCAGTCT    3420

TGTAAGGAAC AAAAATTAGC CATGAGCCAA AAGTATCAAT AAACGGGGAG TGAAGAAACC    3480

CGTTTTATAC AATAAAACCA ATGAGTGTCA AGCTAAAGTA TTGCTTATTC ATGAGCAGTT    3540

AAAACAAATC ACAAAAGGAA AACTAATGTT AGCTCGTGAA AAAAATGCTG TTGAAATAAA    3600

TAATGTCTGA TGTTATTCTT GTATTTTTCT GTGATTGTGA GAACTCCCGT TCCTGTCCCA    3660

CATTGTTTAA CTTGTATAAG ACAATGAGTC TGTTTCTTGT AATGGCTGAC CAGATTGAAG    3720

CCCTGGGTTG TGCTAAAAAT AAATGCAATG ATTGATGCAT GCAATTTTTT ATACAAATAA    3780

TTTATTTCTA ATAATAAAGG AATGTTTTGC AAATGTTAAA AAAAAAAAA AAA            3833
```

(2) INFORMATION FOR SEQ ID NO: 3:

(i) SEQUENCE CHARACTERISTICS:

-continued

```
          (A) LENGTH:            166 base pairs
          (B) TYPE:              nucleic acid
          (C) STRANDEDNESS:      single
          (D) TOPOLOGY:          linear (xi) SEQUENCE DESCRIPTION: SEQ ID NO: 3:

CCCCCACATC TACATTGACT ATGGAGAGCA GCGGACACTA GATCCAGAGA AGGCCAGGGG      60

AGTGCTCAAG TGTGACATTT CTGATCTCTC ACTCATTTGT TCACTTGGAT ACAGTATCCT     120

CTTGATGGTC ACTTCTACTG TTTATGCCAT TAAAACGAGA GGTGTC                    166

(2) INFORMATION FOR SEQ ID NO: 4:

(i) SEQUENCE CHARACTERISTICS:
          (A) LENGTH:            121 base pairs
          (B) TYPE:              nucleic acid
          (C) STRANDEDNESS:      single
          (D) TOPOLOGY:          linear (ix) FEATURE:
          (D) OTHER INFORMATION: The letter "N" stands for A, C, T or
              G.

(xi) SEQUENCE DESCRIPTION: SEQ ID NO: 4:

CTACATTGAC TATGGAGAGC AGCGNACACT AGATCCAGAG AAGGCCAGGG GAGTGCTCAA      60

GTGTGACATT TCTGATCTCT CACTCATTTG TTCACTTGGA TACAGTATCC TCTTGATGGT     120

C                                                                     121

(2) INFORMATION FOR SEQ ID NO: 5:

(i) SEQUENCE CHARACTERISTICS:
          (A) LENGTH:            2724 base pairs
          (B) TYPE:              nucleic acid
          (C) STRANDEDNESS:      single
          (D) TOPOLOGY:          linear (xi) SEQUENCE DESCRIPTION: SEQ ID NO: 5:

ATGGTATGCG AGGGAAAGCG ATCAGCCTCT TGCCCTTGTT TCTTCCTCTT GACCGCCAAG      60

TTCTACTGGA TCCTCACAAT GATGCAAAGA ACTCACAGCC AGGAGTATGC CCATTCCATA     120

CGGGTGGATG GGACATTAT TTTGGGGGGT CTCTTCCCTG TCCACGCAAA GGGAGAGAGA      180

GGGGTGCCTT GTGGGAGCT GAAGAAGGAA AAGGGGATTC ACAGACTGGA GGCCATGCTT      240

TATGCAATTG ACCAGATTAA CAAGGACCCT GATCTCCTTT CCAACATCAC TCTGGGTGTC     300

CGCATCCTCG ACACGTGCTC TAGGGACACC TATGCTTTGG AGCAGTCTCT AACATTCGTG     360

CAGGCATTAA TAGAGAAAGA TGCTTCGGAT GTGAAGTGTG CTAATGGAGA TCCACCCATT     420

TTCACCAAGC CCGACAAGAT TTCTGGCGTC ATAGGTGCTG CAGCAAGCTC CGTGTCCATC     480

ATGGTTGCTA ACATTTTAAG ACTTTTTAAG ATACCTCAAA TCAGCTATGC ATCCACAGCC     540

CCAGAGCTAA GTGATAACAC CAGGTATGAC TTTTTCTCTC GAGTGGTTCC GCCTGACTCC     600

TACCAAGCCC AAGCCATGGT GGACATCGTG ACAGCACTGG GATGGAATTA TGTTTCGACA     660

CTGGCTTCTG AGGGGAACTA TGGTGAGAGC GGTGTGGAGG CCTTCACCCA GATCTCGAGG     720

GAGATTGGTG GTGTTTGCAT TGCTCAGTCA CAGAAAATCC CACGTGAACC AAGACCTGGA     780

GAATTTGAAA AAATTATCAA ACGCCTGCTA GAAACACCTA ATGCTCGAGC AGTGATTATG     840

TTTGCCAATG AGGATGACAT CAGGAGGATA TTGGAAGCAG CAAAAAAACT AAACCAAAGT     900

GGGCATTTTC TCTGGATTGG CTCAGATAGT TGGGGATCCA AAATAGCACC TGTCTATCAG     960

CAAGAGGAGA TTGCAGAAGG GGCTGTGACA ATTTTGCCCA AACGAGCATC AATTGATGGA    1020
```

```
TTTGATCGAT ACTTTAGAAG CCGAACTCTT GCCAATAATC GAAGAAATGT GTGGTTTGCA    1080

GAATTCTGGG AGGAGAATTT TGGCTGCAAG TTAGGATCAC ATGGGAAAAG GAACAGTCAT    1140

ATAAAGAAAT GCACAGGGCT GGAGCGAATT GCTCGGGATT CATCTTATGA ACAGGAAGGA    1200

AAGGTCCAAT TTGTAATTGA TGCTGTATAT TCCATGGCTT ACGCCCTGCA CAATATGCAC    1260

AAAGATCTCT GCCCTGGATA CATTGGCCTT TGTCCACGAA TGAGTACCAT TGATGGGAAA    1320

GAGCTACTTG GTTATATTCG GGCTGTAAAT TTTAATGGCA GTGCTGGCAC TCCTGTCACT    1380

TTTAATGAAA ACGGAGATGC TCCTGGACGT TATGATATCT TCCAGTATCA AATAACCAAC    1440

AAAAGCACAG AGTACAAAGT CATCGGCCAC TGGACCAATC AGCTTCATCT AAAAGTGGAA    1500

GACATGCAGT GGGCTCATAG AGAACATACT CACCCGGCGT CTGTCTGCAG CCTGCCGTGT    1560

AAGCCAGGGG AGAGGAAGAA AACGGTGAAA GGGGTCCCTT GCTGCTGGCA CTGTGAACGC    1620

TGTGAAGGTT ACAACTACCA GGTGGATGAG CTGTCCTGTG AACTTTGCCC TCTGGATCAG    1680

AGACCCAACA TGAACCGCAC AGGCTGCCAG CTTATCCCCA TCATCAAATT GGAGTGGCAT    1740

TCTCCCTGGG CTGTGGTGCC TGTGTTTGTT GCAATATTGG GAATCATCGC CACCACCTTT    1800

GTGATCGTGA CCTTTGTCCG CTATAATGAC ACACCTATCG TGAGGGCTTC AGGACGCGAA    1860

CTTAGTTACG TGCTCCTAAC GGGGATTTTT CTCTGTTATT CAATCACGTT TTTAATGATT    1920

GCAGCACCAG ATACAATCAT ATGCTCCTTC CGACGGGTCT TCCTAGGACT TGGCATGTGT    1980

TTCAGCTATG CAGCCCTTCT GACCAAAACA AACCGTATCC ACCGAATATT TGAGCAGGGG    2040

AAGAAATCTG TCACAGCGCC CAAGTTCATT AGTCCAGCAT CTCAGCTGGT GATCACCTTC    2100

AGCCTCATCT CCGTCCAGCT CCTTGGAGTG TTTGTCTGGT TGTTGTGGA TCCCCCCCAC    2160

ATCATCATTG ACTATGGAGA GCAGCGGACA CTAGATCCAG AGAAGGCCAG GGGAGTGCTC    2220

AAGTGTGACA TTTCTGATCT CTCACTCATT TGTTCACTTG GATACAGTAT CCTCTTGATG    2280

GTCACTTGTA CTGTTTATGC CATTAAAACG AGAGGTGTCC CAGAGACTTT CAATGAAGCC    2340

AAACCTATTG GATTTACCAT GTATACCACC TGCATCATTT GGTTAGCTTT CATCCCCATC    2400

TTTTTTGGTA CAGCCCAGTC AGCAGAAAAG ATGTACATCC AGACAACAAC ACTTACTGTC    2460

TCCATGAGTT TAAGTGCTTC AGTATCTCTG GGCATGCTCT ATATGCCCAA GGTTTATATT    2520

ATAATTTTTC ATCCAGAACA GAATGTTCAA AAACGCAAGA GGAGCTTCAA GGCTGTGGTG    2580

ACAGCTGCCA CCATGCAAAG CAAACTGATC CAAAAAGGAA ATGACAGACC AAATGGCGAG    2640

GTGAAAAGTG AACTCTGTGA GAGTCTTGAA ACCAACAGTA AGTCATCTGT AGAGTTTCCG    2700

ATGGTCAAGA GCGGGAGCAC TTCC                                          2724
```

(2) INFORMATION FOR SEQ ID NO: 6:

(i) SEQUENCE CHARACTERISTICS:
        (A) LENGTH:        33 base pairs
        (B) TYPE:          nucleic acid
        (C) STRANDEDNESS:  single
        (D) TOPOLOGY:      linear (ix) FEATURE:
        (D) OTHER INFORMATION:   The letter "N" stands for Inosine.
            The letter "R" stands for A or G.
            The letter "Y" stands for C or T.
            The letter "S" stands for C or G.
            The letter "M" stands for C or A.

(xi) SEQUENCE DESCRIPTION: SEQ ID NO: 6:

```
CCTGCTCGAG ACNARYCGGG ARCTYTSCTA YMT                                   33
```

```
(2) INFORMATION FOR SEQ ID NO: 7:

(i) SEQUENCE CHARACTERISTICS:
          (A) LENGTH:         31 base pairs
          (B) TYPE:           nucleic acid
          (C) STRANDEDNESS:   single
          (D) TOPOLOGY:       linear (ix) FEATURE:
          (D) OTHER INFORMATION:   The letter "N" stands for Inosine.
              The letter "W" stands for A or T.
              The letter "Y" stands for C or T.
              The letter "S" stands for C or G.
              The letter "R" stands for A or G.

(xi) SEQUENCE DESCRIPTION: SEQ ID NO: 7:

CGGAATTCCG TTNCGGGWYT TGAASGCRWA S                              31

(2) INFORMATION FOR SEQ ID NO: 8:

(i) SEQUENCE CHARACTERISTICS:
          (A) LENGTH:         32 base pairs
          (B) TYPE:           nucleic acid
          (C) STRANDEDNESS:   single
          (D) TOPOLOGY:       linear (ix) FEATURE:
          (D) OTHER INFORMATION:   The letter "R" stands for A or G.
              The letter "N" in position 24
              stands for Inosine.
              The letter "M" stands for A or C.
              The letter "N" in position 27
              stands for A, C, T or G.
              The letter "Y" stands for C or T.

(xi) SEQUENCE DESCRIPTION: SEQ ID NO: 8:

CCTGCTCGAG TCAAGGCTAC GRRNMGNGAR YT                             32

(2) INFORMATION FOR SEQ ID NO: 9:

(i) SEQUENCE CHARACTERISTICS:
          (A) LENGTH:         34 base pairs
          (B) TYPE:           nucleic acid
          (C) STRANDEDNESS:   single
          (D) TOPOLOGY:       linear (ix) FEATURE:
          (D) OTHER INFORMATION:   The letter "N" in position 26
              stands for Inosine.
              The letter "K" stands for T or G.
              The letter "N" in position 29
              stands for A, C, T or G.

(xi) SEQUENCE DESCRIPTION: SEQ ID NO: 9:

CGGAATTCCA TTTGGCTTCG TTGAANKTNK CNGG                           34

(2) INFORMATION FOR SEQ ID NO: 10:

(i) SEQUENCE CHARACTERISTICS:
          (A) LENGTH:         24 base pairs
          (B) TYPE:           nucleic acid
          (C) STRANDEDNESS:   single
          (D) TOPOLOGY:       linear (xi) SEQUENCE DESCRIPTION: SEQ ID NO: 10:

CTACATTGAC TATGGAGAGC AGCG                                      24
```

```
(2) INFORMATION FOR SEQ ID NO: 11:

(i) SEQUENCE CHARACTERISTICS:
        (A) LENGTH:           24 base pairs
        (B) TYPE:             nucleic acid
        (C) STRANDEDNESS:     single
        (D) TOPOLOGY:         linear (xi) SEQUENCE DESCRIPTION: SEQ ID NO: 11:

GACCATCAAG AGGATACTGT ATCC                                              24

(2) INFORMATION FOR SEQ ID NO: 12:

(i) SEQUENCE CHARACTERISTICS:
        (A) LENGTH:           23 base pairs
        (B) TYPE:             nucleic acid
        (C) STRANDEDNESS:     single
        (D) TOPOLOGY:         linear (xi) SEQUENCE DESCRIPTION: SEQ ID NO: 12:

GATGTACATC CAGACAACAA CAC                                               23

(2) INFORMATION FOR SEQ ID NO: 13:

(i) SEQUENCE CHARACTERISTICS:
        (A) LENGTH:           24 base pairs
        (B) TYPE:             nucleic acid
        (C) STRANDEDNESS:     single
        (D) TOPOLOGY:         linear (xi) SEQUENCE DESCRIPTION: SEQ ID NO: 13:

CAGATTGTGC CATTTCCCTG TTTC                                              24

(2) INFORMATION FOR SEQ ID NO: 14:

(i) SEQUENCE CHARACTERISTICS:
        (A) LENGTH:           24 base pairs
        (B) TYPE:             nucleic acid
        (C) STRANDEDNESS:     single
        (D) TOPOLOGY:         linear (xi) SEQUENCE DESCRIPTION: SEQ ID NO: 14:

GGAAATGACA GACCAAATGG CGAG                                              24

(2) INFORMATION FOR SEQ ID NO: 15:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (xi) SEQUENCE DESCRIPTION: SEQ ID NO: 15:

CATGGGCCCT GATGGAAGCT TCCAGAAGGT G                                      31

(2) INFORMATION FOR SEQ ID NO: 16:

(i) SEQUENCE CHARACTERISTICS:
        (A) LENGTH:           24 base pairs
        (B) TYPE:             nucleic acid
        (C) STRANDEDNESS:     single
        (D) TOPOLOGY:         linear (xi) SEQUENCE DESCRIPTION: SEQ ID NO: 16:

GATGAATCCC GAGCAATTCG CTCC                                              24
```